US008865166B2

(12) United States Patent
Cochrane et al.

(10) Patent No.: US 8,865,166 B2
(45) Date of Patent: Oct. 21, 2014

(54) ANTIBODIES TO IL-17A AND USES THEREOF

(75) Inventors: Duncan Cochrane, Cambridge (GB);
Caroline Russell, Cambridge (GB);
Matthew Sleeman, Cambridge (GB);
Fraser Welsh, Cambridge (GB);
Caroline Langham, Macclesfield (GB);
Maurice Needham, Macclesfield (GB);
Patrick Dufner, Zurich (CH)

(73) Assignee: MedImmune Limited, Cambridge (GB)

( * ) Notice: Subject to any disclaimer, the term of this patent is extended or adjusted under 35 U.S.C. 154(b) by 1228 days.

(21) Appl. No.: 11/767,208

(22) Filed: Jun. 22, 2007

(65) Prior Publication Data

US 2008/0044423 A1  Feb. 21, 2008

Related U.S. Application Data

(60) Provisional application No. 60/815,828, filed on Jun. 23, 2006, provisional application No. 60/913,566, filed on Apr. 24, 2007.

(51) Int. Cl.
| | | |
|---|---|---|
| *A61K 39/395* | (2006.01) | |
| *C07K 16/24* | (2006.01) | |
| *C07K 14/54* | (2006.01) | |
| *A61K 39/00* | (2006.01) | |

(52) U.S. Cl.
CPC ........... *C07K 16/244* (2013.01); *C07K 2316/96* (2013.01); *C07K 2299/00* (2013.01); *C07K 2317/56* (2013.01); *C07K 2317/92* (2013.01); *C07K 2317/34* (2013.01); *C07K 2317/622* (2013.01); *C07K 2317/565* (2013.01); *C07K 2317/21* (2013.01); *C07K 2317/55* (2013.01); *C07K 14/54* (2013.01); *A61K 2039/505* (2013.01)
USPC .................. 424/133.1; 424/145.1; 424/130.1; 530/388.23; 530/387.3; 530/351

(58) Field of Classification Search
None
See application file for complete search history.

(56) References Cited

U.S. PATENT DOCUMENTS 6,274,711 B1 *  8/2001  Golstein et al. ............ 530/389.2

FOREIGN PATENT DOCUMENTS

| WO | WO 2006/013107 A1 | 2/2006 |
| WO | WO 2006/054059 A1 | 5/2006 |
| WO | WO 2007/070750 A1 | 6/2007 |

OTHER PUBLICATIONS

MacCallum et al. Antibody-antigen Interactions: Contact Analysis and Binding Site Topography. J. Mol. Biol., 1996, 262:732-745.*
Padlan et al. Structure of an antibody-antigen complex: crystal structure of the HyHEL-10 Fab-lysozyme complex. Proc. Natl. Acad. Sci. USA, 1989, 86: 5938-5942.*
Rudikoff et al. Single amino acid substitution altering antigen-binding specificity. Proc. Natl. Acad. Sci, USA, 1982, vol. 79:1979-1983.*
Supplementary European Search Report mailed Jun. 18, 2010 for EP Application No. 07748263.6.
Jan. 11, 2004, R&D Systems: "Monoclonal Anti-human IL-17 Antibody", Announcement R&D Systems, pp. 1-2.
Burchhill, Matthew A. et al., 2003, "Inhibition of Interleukin-17 Prevents the Development of Arthritis in Vaccinated Mice Challenged with *Borrelia burgdorferi*", Infection and Immunity, 71(6):3437-3442.
Hellings, Peter W. et al., 2003, "Interleukin-17 Orchestrates the Granulocyte Influx into Airways after Allergen Inhalation in a Mouse Model of Allergic Asthma", American Journal of Respiratory Cell and Molecular Biology, 28(1):42-50.
Malley, Richard et al., 2006, "Antibody-Independent, Interleukin-17A-Mediated, Cross-Serotype Immunity to Pneumococci in Mice Immunized Intranasally with the Cell Wall Polysaccharide", Infection and Immunity, 74(4):2187-2195.
Lubberts, Erik et al., 2004, "Treatment With a Neutralizing Anti-Murine Interleukin-17 Antibody After the Onset of Collagen-Induced Arthritis Reduces Joint Inflammation, Cartilage Destruction, and Bone Erosion" Arthritis and Rheumatism, 50(2):650-659.
Koenders, Marije I. et al., 2005, "Blocking of Interleukin-17 during Reactivation of Experimental Arthritis Prevents Joint Inflammation and Bone Erosion by Decreasing RANKL and Interleukin-1" The American Journal of Pathology, 167(1):141-149.
Chabaud, M., et al., 2000, "Contribution of Interleukin 17 to Synovium Matrix Destruction in Rheumatoid Arthritis" Cytokine, 12(7): 1092-1099.
International Search Report corresponding to PCT/SE2007/000600 dated Oct. 17, 2007.
Rudikoff, Stuart et al., 1982, "Single amino acid substitution altering antigen-binding specificity", Proc. Natl. Acad. Sci. USA, vol. 79, pp. 1979-1983.

* cited by examiner

*Primary Examiner* — Dong Jiang

(57) ABSTRACT

Binding members, especially antibody molecules, for interleukin 17 (IL-17). The binding members are useful for the treatment of disorders associated with interleukin 17 such as rheumatoid arthritis.

8 Claims, 2 Drawing Sheets

MGGLNDIFEAQKIEWHEIVKAGITIPRNPGCPNSEDKNFPRTVMVNLNIHNRNTNTNPKRSSDY
YNRSTSPWNLHRNEDPERYPSVIWEAK|CRHLGCINADGNVDYHM|NSVPIQQEILVLRREPPHCP
NSFRLEKILVSVGCTCVTPIVHHVA

Figure 1

MTPGKTSLVSLLLLLSLEAIVKAGITIPRNPGCPNSEDKNFPRTVMVNLNIHNRNTNTNPKRSS
DYYNRSTSPWNLHRNEDPERYPSVIWEAK|CRHQRCVNAEGKLDHHM|NSVPIQQEILVLRREPPH
CPNSFRLEKILVSVGCTCVTPIVHHVAHHHHH

Figure 2

SEQUENCE LISTING

```
<160> NUMBER OF SEQ ID NOS: 201

<210> SEQ ID NO 1
<211> LENGTH: 354
<212> TYPE: DNA
<213> ORGANISM: Homo sapiens
<220> FEATURE:
<223> OTHER INFORMATION: Antibody 01

<400> SEQUENCE: 1
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
```

```
ctgcaaatga acagcctgag agccgaggac acggccgtgt attactgtgc aagagatcta    300
atttggggag tggctgggag ctggggccag gggacaatgg tcaccgtctc ctca          354
```

<210> SEQ ID NO 2
<211> LENGTH: 118
<212> TYPE: PRT
<213> ORGANISM: Homo sapiens
<220> FEATURE:
<223> OTHER INFORMATION: Antibody 01

<400> SEQUENCE: 2

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile Trp Gly Val Ala Gly Ser Trp Gly Gln Gly Thr
            100                 105                 110

Met Val Thr Val Ser Ser
        115

<210> SEQ ID NO 3
<211> LENGTH: 5
<212> TYPE: PRT
<213> ORGANISM: Homo sapiens
<220> FEATURE:
<223> OTHER INFORMATION: Antibody 01

<400> SEQUENCE: 3

Ser Tyr Ala Met Ser
 1               5

<210> SEQ ID NO 4
<211> LENGTH: 17
<212> TYPE: PRT
<213> ORGANISM: Homo sapiens
<220> FEATURE:
<223> OTHER INFORMATION: Antibody 01

<400> SEQUENCE: 4

Ala Ile Ser Gly Ser Gly Gly Ser Thr Tyr Tyr Ala Asp Ser Val Lys
 1               5                  10                  15

Gly

<210> SEQ ID NO 5
<211> LENGTH: 9
<212> TYPE: PRT
<213> ORGANISM: Homo sapiens
<220> FEATURE:
<223> OTHER INFORMATION: Antibody 01

<400> SEQUENCE: 5

Asp Leu Ile Trp Gly Val Ala Gly Ser
 1               5

<210> SEQ ID NO 6
<211> LENGTH: 336
<212> TYPE: DNA
<213> ORGANISM: Homo sapiens
<220> FEATURE:
<223> OTHER INFORMATION: Antibody 01

<400> SEQUENCE: 6

```
aattttatgc tgactcagcc ccactctgtg tcggagtctc cggggaagac ggtaaccatc    60
tcctgcaccc gcagcagtgg cagccttgcc aactactatg tgcagtggta ccaacagcgc   120
ccgggcagtg cccccaccat tgtgatcttt gcgaataacc aaagaccctc tggggtccct   180
gatcgattct ctggctccat cgacagctcc tccaactctg cctccctcac catctctaga   240
ctgaagactg aggacgaggc tgactactac tgccagtctt atgatgacag cagcgtggtg   300
ttcggcggag ggaccaagct gaccgtccta ggtgag                             336
```

<210> SEQ ID NO 7
<211> LENGTH: 112
<212> TYPE: PRT
<213> ORGANISM: Homo sapiens
<220> FEATURE:
<223> OTHER INFORMATION: Antibody 01

<400> SEQUENCE: 7

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Asp Asp
                85                  90                  95

Ser Ser Val Val Phe Gly Gly Gly Thr Lys Leu Thr Val Leu Gly Glu
            100                 105                 110

<210> SEQ ID NO 8
<211> LENGTH: 13
<212> TYPE: PRT
<213> ORGANISM: Homo sapiens
<220> FEATURE:
<223> OTHER INFORMATION: Antibody 01

<400> SEQUENCE: 8

Thr Arg Ser Ser Gly Ser Leu Ala Asn Tyr Tyr Val Gln
1               5                   10

<210> SEQ ID NO 9
<211> LENGTH: 7
<212> TYPE: PRT
<213> ORGANISM: Homo sapiens
<220> FEATURE:
<223> OTHER INFORMATION: Antibody 01

<400> SEQUENCE: 9

Ala Asn Asn Gln Arg Pro Ser
1               5

<210> SEQ ID NO 10
<211> LENGTH: 9
<212> TYPE: PRT
<213> ORGANISM: Homo sapiens
<220> FEATURE:
<223> OTHER INFORMATION: Antibody 01

<400> SEQUENCE: 10

Gln Ser Tyr Asp Asp Ser Ser Val Val
                5

<210> SEQ ID NO 11
<211> LENGTH: 354
<212> TYPE: DNA
<213> ORGANISM: Homo sapiens
<220> FEATURE:
<223> OTHER INFORMATION: Antibody 02

<400> SEQUENCE: 11
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg gctggagtg gtctcagct attagtggta gtggtggtag cacatactac    180
gcagactccg tgaagggccg gttcaccatc tccagagaca attccaagaa cacgctgtat   240
ctgcaaatga acagcctgag agccgaggac acggccgtgt attactgtgc aagagatcta   300
atttggggag tggctgggag ctggggccag gggacactgg tcaccgtctc ctca         354

<210> SEQ ID NO 12
<211> LENGTH: 118
<212> TYPE: PRT
<213> ORGANISM: Homo sapiens
<220> FEATURE:
<223> OTHER INFORMATION: Antibody 02

<400> SEQUENCE: 12

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile Trp Gly Val Ala Gly Ser Trp Gly Gln Gly Thr
            100                 105                 110

Leu Val Thr Val Ser Ser
        115

<210> SEQ ID NO 13
<211> LENGTH: 5
<212> TYPE: PRT
<213> ORGANISM: Homo sapiens
<220> FEATURE:
<223> OTHER INFORMATION: Antibody 02

<400> SEQUENCE: 13

Ser Tyr Ala Met Ser
            5

<210> SEQ ID NO 14
<211> LENGTH: 17
<212> TYPE: PRT
<213> ORGANISM: Homo sapiens
<220> FEATURE:
<223> OTHER INFORMATION: Antibody 02

<400> SEQUENCE: 14

Ala Ile Ser Gly Ser Gly Gly Ser Thr Tyr Tyr Ala Asp Ser Val Lys
            5                   10                  15

Gly

<210> SEQ ID NO 15
<211> LENGTH: 9
<212> TYPE: PRT
<213> ORGANISM: Homo sapiens
<220> FEATURE:
<223> OTHER INFORMATION: Antibody 02

<400> SEQUENCE: 15

Asp Leu Ile Trp Gly Val Ala Gly Ser
            5

<210> SEQ ID NO 16
<211> LENGTH: 336
<212> TYPE: DNA
<213> ORGANISM: Homo sapiens
<220> FEATURE:
<223> OTHER INFORMATION: Antibody 02

<400> SEQUENCE: 16
aattttatgc tgactcagcc ccactctgtg tcggagtctc cggggaagac ggtaaccatc      60
tcctgcaccc gcagcagtgg cagccttgcc aactactatg tgcagtggta ccaacagcgc     120
ccgggcagtt cccccaccat tgtgatcttt gcgaataacc aaagaccctc tggggtccct     180
gatcgattct ctggctccat cgacagctcc tccaactctg cctccctcac catctctgga     240
ctgaagactg aggacgaggc tgactactac tgccagtcgt acgaccccca cagcgtggtg     300
ttcggcggag ggaccaagct gaccgtccta ggtgag                               336

<210> SEQ ID NO 17
<211> LENGTH: 112
<212> TYPE: PRT
<213> ORGANISM: Homo sapiens
<220> FEATURE:
<223> OTHER INFORMATION: Antibody 02

<400> SEQUENCE: 17

Asn Phe Met Leu Thr Gln Pro His Ser Val Ser Glu Ser Pro Gly Lys
            5                   10                  15

Thr Val Thr Ile Ser Cys Thr Arg Ser Ser Gly Ser Leu Ala Asn Tyr
        20                  25                  30

Tyr Val Gln Trp Tyr Gln Gln Arg Pro Gly Ser Ser Pro Thr Ile Val
    35                  40                  45

Ile Phe Ala Asn Asn Gln Arg Pro Ser Gly Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Pro
            85                  90                  95

His Ser Val Val Phe Gly Gly Gly Thr Lys Leu Thr Val Leu Gly Glu
            100                 105                 110

<210> SEQ ID NO 18
<211> LENGTH: 13
<212> TYPE: PRT
<213> ORGANISM: Homo sapiens
<220> FEATURE:
<223> OTHER INFORMATION: Antibody 02

<400> SEQUENCE: 18

Thr Arg Ser Ser Gly Ser Leu Ala Asn Tyr Tyr Val Gln
            5                   10

<210> SEQ ID NO 19
<211> LENGTH: 7
<212> TYPE: PRT
<213> ORGANISM: Homo sapiens
<220> FEATURE:
<223> OTHER INFORMATION: Antibody 02

<400> SEQUENCE: 19

Ala Asn Asn Gln Arg Pro Ser
            5

<210> SEQ ID NO 20
<211> LENGTH: 9
<212> TYPE: PRT
<213> ORGANISM: Homo sapiens
<220> FEATURE:
<223> OTHER INFORMATION: Antibody 02

<400> SEQUENCE: 20

Gln Ser Tyr Asp Pro His Ser Val Val
            5

<210> SEQ ID NO 21
<211> LENGTH: 354
<212> TYPE: DNA
<213> ORGANISM: Homo sapiens
<220> FEATURE:
<223> OTHER INFORMATION: Antibody 03

<400> SEQUENCE: 21
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc aagagatcta     300
attcacgggg tgacgcggaa ctggggccag gggacactgg tcaccgtctc ctca           354

<210> SEQ ID NO 22
<211> LENGTH: 118
<212> TYPE: PRT
<213> ORGANISM: Homo sapiens
<220> FEATURE:
<223> OTHER INFORMATION: Antibody 03

<400> SEQUENCE: 22

Glu Val Gln Leu Leu Glu Ser Gly Gly Gly Leu Val Gln Pro Gly Gly
            5                   10                  15

```
Ser Leu Arg Leu Ser Cys Ala Ala Ser Gly Phe Thr Phe Ser Ser Tyr
         20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Ile His Gly Val Thr Arg Asn Trp Gly Gln Gly Thr
            100                 105                 110

Leu Val Thr Val Ser Ser
            115

<210> SEQ ID NO 23
<211> LENGTH: 5
<212> TYPE: PRT
<213> ORGANISM: Homo sapiens
<220> FEATURE:
<223> OTHER INFORMATION: Antibody 03

<400> SEQUENCE: 23

Ser Tyr Ala Met Ser
              5

<210> SEQ ID NO 24
<211> LENGTH: 17
<212> TYPE: PRT
<213> ORGANISM: Homo sapiens
<220> FEATURE:
<223> OTHER INFORMATION: Antibody 03

<400> SEQUENCE: 24

Ala Ile Ser Gly Ser Gly Gly Ser Thr Tyr Tyr Ala Asp Ser Val Lys
                 5                  10                  15

Gly

<210> SEQ ID NO 25
<211> LENGTH: 9
<212> TYPE: PRT
<213> ORGANISM: Homo sapiens
<220> FEATURE:
<223> OTHER INFORMATION: Antibody 03

<400> SEQUENCE: 25

Asp Leu Ile His Gly Val Thr Arg Asn
              5

<210> SEQ ID NO 26
<211> LENGTH: 336
<212> TYPE: DNA
<213> ORGANISM: Homo sapiens
<220> FEATURE:
<223> OTHER INFORMATION: Antibody 03

<400> SEQUENCE: 26
aattttatgc tgactcagcc ccactctgtg tcggagtctc cggggaagac ggtaaccatc     60
tcctgcaccc gcagcagtgg cagccttgcc aactactatg tgcagtggta ccaacagcgc    120
ccgggcagtg cccccaccat tgtgatcttt gcgaataacc aaagaccctc tggggtccct    180
```

```
gatcgattct ctggctccat cgacagctcc tccaactctg cctccctcac catctctaga    240
ctgaagactg aggacgaggc tgactactac tgccagtcct actcccccca cagcgtggtg    300
ttcggcggag ggaccaagct gaccgtccta ggtgag                              336
```

<210> SEQ ID NO 27
<211> LENGTH: 112
<212> TYPE: PRT
<213> ORGANISM: Homo sapiens
<220> FEATURE:
<223> OTHER INFORMATION: Antibody 03

<400> SEQUENCE: 27

```
Asn Phe Met Leu Thr Gln Pro His Ser Val Ser Glu Ser Pro Gly Lys
              5                  10                  15

Thr Val Thr Ile Ser Cys Thr Arg Ser Ser Gly Ser Leu Ala Asn Tyr
         20                  25                  30

Tyr Val Gln Trp Tyr Gln Gln Arg Pro Gly Ser Ala Pro Thr Ile Val
     35                  40                  45

Ile Phe Ala Asn Asn Gln Arg Pro Ser Gly Val Pro Asp Arg Phe Ser
 50                  55                  60

Gly Ser Ile Asp Ser Ser Asn Ser Ala Ser Leu Thr Ile Ser Arg
 65                  70                  75              80

Leu Lys Thr Glu Asp Glu Ala Asp Tyr Tyr Cys Gln Ser Tyr Ser Pro
             85                  90                  95

His Ser Val Val Phe Gly Gly Gly Thr Lys Leu Thr Val Leu Gly Glu
        100                 105                 110
```

<210> SEQ ID NO 28
<211> LENGTH: 13
<212> TYPE: PRT
<213> ORGANISM: Homo sapiens
<220> FEATURE:
<223> OTHER INFORMATION: Antibody 03

<400> SEQUENCE: 28

```
Thr Arg Ser Ser Gly Ser Leu Ala Asn Tyr Tyr Val Gln
              5                  10
```

<210> SEQ ID NO 29
<211> LENGTH: 7
<212> TYPE: PRT
<213> ORGANISM: Homo sapiens
<220> FEATURE:
<223> OTHER INFORMATION: Antibody 03

<400> SEQUENCE: 29

```
Ala Asn Asn Gln Arg Pro Ser
              5
```

<210> SEQ ID NO 30
<211> LENGTH: 9
<212> TYPE: PRT
<213> ORGANISM: Homo sapiens
<220> FEATURE:
<223> OTHER INFORMATION: Antibody 03

<400> SEQUENCE: 30

```
Gln Ser Tyr Ser Pro His Ser Val Val
              5
```

<210> SEQ ID NO 31
<211> LENGTH: 354

```
<212> TYPE: DNA
<213> ORGANISM: Homo sapiens
<220> FEATURE:
<223> OTHER INFORMATION: Antibody 04

<400> SEQUENCE: 31
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggccgtgt attactgtgc aagagatcta     300
attcacgggg tgacgcggaa ctggggccag gggacactgg tcaccgtctc ctca           354

<210> SEQ ID NO 32
<211> LENGTH: 118
<212> TYPE: PRT
<213> ORGANISM: Homo sapiens
<220> FEATURE:
<223> OTHER INFORMATION: Antibody 04

<400> SEQUENCE: 32

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile His Gly Val Thr Arg Asn Trp Gly Gln Gly Thr
            100                 105                 110

Leu Val Thr Val Ser Ser
        115

<210> SEQ ID NO 33
<211> LENGTH: 5
<212> TYPE: PRT
<213> ORGANISM: Homo sapiens
<220> FEATURE:
<223> OTHER INFORMATION: Antibody 04

<400> SEQUENCE: 33

Ser Tyr Ala Met Ser
                 5

<210> SEQ ID NO 34
<211> LENGTH: 17
<212> TYPE: PRT
<213> ORGANISM: Homo sapiens
<220> FEATURE:
<223> OTHER INFORMATION: Antibody 04

<400> SEQUENCE: 34

Ala Ile Ser Gly Ser Gly Gly Ser Thr Tyr Tyr Ala Asp Ser Val Lys
                 5                  10                  15
```

Gly

<210> SEQ ID NO 35
<211> LENGTH: 9
<212> TYPE: PRT
<213> ORGANISM: Homo sapiens
<220> FEATURE:
<223> OTHER INFORMATION: Antibody 04

<400> SEQUENCE: 35

Asp Leu Ile His Gly Val Thr Arg Asn
                5

<210> SEQ ID NO 36
<211> LENGTH: 336
<212> TYPE: DNA
<213> ORGANISM: Homo sapiens
<220> FEATURE:
<223> OTHER INFORMATION: Antibody 04

<400> SEQUENCE: 36
aattttatgc tgactcagcc ccactctgtg tcggagtctc cggggaagac ggtaaccatc      60
tcctgcaccc gcagcagtgg cagccttgcc aactactatg tgcagtggta ccaacagcgc     120
ccgggcagtg cccccaccat tgtgatcttt gcgaataacc aaagaccctc tggggtccct     180
gatcgattct ctggctccat cgacagctcc tccaactctg cctccctcac catctctaga     240
ctgaagactg aggacgaggc tgactactac tgccagtcct actccccgac gagcgtggtg     300
ttcggcggag ggaccaagct gaccgtccta ggtgag                              336

<210> SEQ ID NO 37
<211> LENGTH: 112
<212> TYPE: PRT
<213> ORGANISM: Homo sapiens
<220> FEATURE:
<223> OTHER INFORMATION: Antibody 04

<400> SEQUENCE: 37

Asn Phe Met Leu Thr Gln Pro His Ser Val Ser Glu Ser Pro Gly Lys
                5                  10                   15

Thr Val Thr Ile Ser Cys Thr Arg Ser Ser Gly Ser Leu Ala Asn Tyr
             20                  25                  30

Tyr Val Gln Trp Tyr Gln Gln Arg Pro Gly Ser Ala Pro Thr Ile Val
         35                   40                  45

Ile Phe Ala Asn Asn Gln Arg Pro Ser Gly Val Pro Asp Arg Phe Ser
     50                  55                  60

Gly Ser Ile Asp Ser Ser Ser Asn Ser Ala Ser Leu Thr Ile Ser Arg
65                   70                  75                   80

Leu Lys Thr Glu Asp Glu Ala Asp Tyr Tyr Cys Gln Ser Tyr Ser Pro
                85                  90                  95

Thr Ser Val Val Phe Gly Gly Gly Thr Lys Leu Thr Val Leu Gly Glu
            100                 105                 110

<210> SEQ ID NO 38
<211> LENGTH: 13
<212> TYPE: PRT
<213> ORGANISM: Homo sapiens
<220> FEATURE:
<223> OTHER INFORMATION: Antibody 04

<400> SEQUENCE: 38

Thr Arg Ser Ser Gly Ser Leu Ala Asn Tyr Tyr Val Gln

```
                5                   10

<210> SEQ ID NO 39
<211> LENGTH: 7
<212> TYPE: PRT
<213> ORGANISM: Homo sapiens
<220> FEATURE:
<223> OTHER INFORMATION: Antibody 04

<400> SEQUENCE: 39

Ala Asn Asn Gln Arg Pro Ser
                5

<210> SEQ ID NO 40
<211> LENGTH: 9
<212> TYPE: PRT
<213> ORGANISM: Homo sapiens
<220> FEATURE:
<223> OTHER INFORMATION: Antibody 04

<400> SEQUENCE: 40

Gln Ser Tyr Ser Pro Thr Ser Val Val
                5

<210> SEQ ID NO 41
<211> LENGTH: 354
<212> TYPE: DNA
<213> ORGANISM: Homo sapiens
<220> FEATURE:
<223> OTHER INFORMATION: Antibody 05

<400> SEQUENCE: 41
gaggtgcagc tgttggagtc tggggggaggc ttggtacagc ctggggggtc cctgagactc        60
tcctgtgcag cctctggatt cacctttagc agctatgcca tgagctgggt ccgccaggct       120
ccagggaagg ggctggagtg ggtctcagct attagtggta gtggtggtag cacatactac       180
gcagactccg tgaagggccg gttcaccatc tccagagaca attccaagaa cacgctgtat       240
ctgcaaatga acagcctgag agccgaggac acggccgtgt attactgtgc aagagatcta       300
attcacgggg tgacgcggaa ctggggccag gggacactgg tcaccgtctc ctca              354

<210> SEQ ID NO 42
<211> LENGTH: 118
<212> TYPE: PRT
<213> ORGANISM: Homo sapiens
<220> FEATURE:
<223> OTHER INFORMATION: Antibody 05

<400> SEQUENCE: 42

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile His Gly Val Thr Arg Asn Trp Gly Gln Gly Thr
```

Leu Val Thr Val Ser Ser
            115

<210> SEQ ID NO 43
<211> LENGTH: 5
<212> TYPE: PRT
<213> ORGANISM: Homo sapiens
<220> FEATURE:
<223> OTHER INFORMATION: Antibody 05

<400> SEQUENCE: 43

Ser Tyr Ala Met Ser
            5

<210> SEQ ID NO 44
<211> LENGTH: 17
<212> TYPE: PRT
<213> ORGANISM: Homo sapiens
<220> FEATURE:
<223> OTHER INFORMATION: Antibody 05

<400> SEQUENCE: 44

Ala Ile Ser Gly Ser Gly Gly Ser Thr Tyr Tyr Ala Asp Ser Val Lys
            5                   10                  15

Gly

<210> SEQ ID NO 45
<211> LENGTH: 9
<212> TYPE: PRT
<213> ORGANISM: Homo sapiens
<220> FEATURE:
<223> OTHER INFORMATION: Antibody 05

<400> SEQUENCE: 45

Asp Leu Ile His Gly Val Thr Arg Asn
            5

<210> SEQ ID NO 46
<211> LENGTH: 336
<212> TYPE: DNA
<213> ORGANISM: Homo sapiens
<220> FEATURE:
<223> OTHER INFORMATION: Antibody 05

<400> SEQUENCE: 46
aattttatgc tgactcagcc ccactctgtg tcggagtctc cggggaagac ggtaaccatc    60
tcctgcaccc gcagcagtgg cagccttgcc aactactatg tgcagtggta ccaacagcgc   120
ccgggcagtg cccccaccat tgtgatcttt gcgaataacc aaagaccctc tggggtccct   180
gatcgattct ctggctccat cgacagctcc tccaactctg cctccctcac catctctaga   240
ctgaagactg aggacgaggc tgactactac tgccagtctt ataaccacaa ggacatcgtg   300
ttcggcggag ggaccaagct gaccgtccta ggtgag                             336

<210> SEQ ID NO 47
<211> LENGTH: 112
<212> TYPE: PRT
<213> ORGANISM: Homo sapiens
<220> FEATURE:
<223> OTHER INFORMATION: Antibody 05

<400> SEQUENCE: 47

Asn Phe Met Leu Thr Gln Pro His Ser Val Ser Glu Ser Pro Gly Lys

```
                  5                  10                 15
Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
            35                  40                  45

Ile Phe Ala Asn Asn Gln Arg Pro Ser Gly Val Pro Asp Arg Phe Ser
        50                  55                  60

Gly Ser Ile Asp Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Asn His
                85                  90                  95

Lys Asp Ile Val Phe Gly Gly Gly Thr Lys Leu Thr Val Leu Gly Glu
            100                 105                 110
```

<210> SEQ ID NO 48
<211> LENGTH: 13
<212> TYPE: PRT
<213> ORGANISM: Homo sapiens
<220> FEATURE:
<223> OTHER INFORMATION: Antibody 05

<400> SEQUENCE: 48

```
Thr Arg Ser Ser Gly Ser Leu Ala Asn Tyr Tyr Val Gln
              5                  10
```

<210> SEQ ID NO 49
<211> LENGTH: 7
<212> TYPE: PRT
<213> ORGANISM: Homo sapiens
<220> FEATURE:
<223> OTHER INFORMATION: Antibody 05

<400> SEQUENCE: 49

```
Ala Asn Asn Gln Arg Pro Ser
              5
```

<210> SEQ ID NO 50
<211> LENGTH: 9
<212> TYPE: PRT
<213> ORGANISM: Homo sapiens
<220> FEATURE:
<223> OTHER INFORMATION: Antibody 05

<400> SEQUENCE: 50

```
Gln Ser Tyr Asn His Lys Asp Ile Val
              5
```

<210> SEQ ID NO 51
<211> LENGTH: 354
<212> TYPE: DNA
<213> ORGANISM: Homo sapiens
<220> FEATURE:
<223> OTHER INFORMATION: Antibody 06

<400> SEQUENCE: 51

```
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc aagagatcta    300
```

```
atttggggag tggctgggag ctggggccag gggacactgg tcaccgtctc ctca          354
```

<210> SEQ ID NO 52
<211> LENGTH: 118
<212> TYPE: PRT
<213> ORGANISM: Homo sapiens
<220> FEATURE:
<223> OTHER INFORMATION: Antibody 06

<400> SEQUENCE: 52

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Asp Leu Ile Trp Gly Val Ala Gly Ser Trp Gly Gln Gly Thr
            100                 105                 110

Leu Val Thr Val Ser Ser
        115

<210> SEQ ID NO 53
<211> LENGTH: 5
<212> TYPE: PRT
<213> ORGANISM: Homo sapiens
<220> FEATURE:
<223> OTHER INFORMATION: Antibody 06

<400> SEQUENCE: 53

Ser Tyr Ala Met Ser
                 5

<210> SEQ ID NO 54
<211> LENGTH: 17
<212> TYPE: PRT
<213> ORGANISM: Homo sapiens
<220> FEATURE:
<223> OTHER INFORMATION: Antibody 06

<400> SEQUENCE: 54

Ala Ile Ser Gly Ser Gly Gly Ser Thr Tyr Tyr Ala Asp Ser Val Lys
                 5                  10                  15

Gly

<210> SEQ ID NO 55
<211> LENGTH: 9
<212> TYPE: PRT
<213> ORGANISM: Homo sapiens
<220> FEATURE:
<223> OTHER INFORMATION: Antibody 06

<400> SEQUENCE: 55

Asp Leu Ile Trp Gly Val Ala Gly Ser
                 5

<210> SEQ ID NO 56

<211> LENGTH: 336
<212> TYPE: DNA
<213> ORGANISM: Homo sapiens
<220> FEATURE:
<223> OTHER INFORMATION: Antibody 06

<400> SEQUENCE: 56

```
aattttatgc tgactcagcc ccactctgtg tcggagtctc cggggaagac ggtaaccatc    60
tcctgcaccc gcagcagtgg cagccttgcc aactactatg tgcagtggta ccaacagcgc   120
ccgggcagtg cccccaccat tgtgatcttt gcgaataacc aaagaccctc tggggtccct   180
gatcgattct ctggctccat cgacagctcc tccaactctg cctccctcac catctctaga   240
ctgaagactg aggacgaggc tgactactac tgccagtcgt acagcccgag cagcgtggtg   300
ttcggcggag ggaccaagct gaccgtccta ggtgag                             336
```

<210> SEQ ID NO 57
<211> LENGTH: 112
<212> TYPE: PRT
<213> ORGANISM: Homo sapiens
<220> FEATURE:
<223> OTHER INFORMATION: Antibody 06

<400> SEQUENCE: 57

Asn Phe Met Leu Thr Gln Pro His Ser Val Ser Glu Ser Pro Gly Lys
                5                  10                  15
Thr Val Thr Ile Ser Cys Thr Arg Ser Ser Gly Ser Leu Ala Asn Tyr
            20                  25                  30
Tyr Val Gln Trp Tyr Gln Gln Arg Pro Gly Ser Ala Pro Thr Ile Val
        35                  40                  45
Ile Phe Ala Asn Asn Gln Arg Pro Ser Gly Val Pro Asp Arg Phe Ser
    50                  55                  60
Gly Ser Ile Asp Ser Ser Ser Asn Ser Ala Ser Leu Thr Ile Ser Arg
65                  70                  75                  80
Leu Lys Thr Glu Asp Glu Ala Asp Tyr Tyr Cys Gln Ser Tyr Ser Pro
                85                  90                  95
Ser Ser Val Val Phe Gly Gly Gly Thr Lys Leu Thr Val Leu Gly Glu
            100                 105                 110

<210> SEQ ID NO 58
<211> LENGTH: 13
<212> TYPE: PRT
<213> ORGANISM: Homo sapiens
<220> FEATURE:
<223> OTHER INFORMATION: Antibody 06

<400> SEQUENCE: 58

Thr Arg Ser Ser Gly Ser Leu Ala Asn Tyr Tyr Val Gln
                5                  10

<210> SEQ ID NO 59
<211> LENGTH: 7
<212> TYPE: PRT
<213> ORGANISM: Homo sapiens
<220> FEATURE:
<223> OTHER INFORMATION: Antibody 06

<400> SEQUENCE: 59

Ala Asn Asn Gln Arg Pro Ser
                5

<210> SEQ ID NO 60

```
<211> LENGTH: 9
<212> TYPE: PRT
<213> ORGANISM: Homo sapiens
<220> FEATURE:
<223> OTHER INFORMATION: Antibody 06

<400> SEQUENCE: 60

Gln Ser Tyr Ser Pro Ser Ser Val Val
                5

<210> SEQ ID NO 61
<211> LENGTH: 354
<212> TYPE: DNA
<213> ORGANISM: Homo sapiens
<220> FEATURE:
<223> OTHER INFORMATION: Antibody 07

<400> SEQUENCE: 61
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggccgtgt attactgtgc aagagatcta    300
attcacgggg tgacgcggaa ctggggccag gggacactgg tcaccgtctc ctca          354

<210> SEQ ID NO 62
<211> LENGTH: 118
<212> TYPE: PRT
<213> ORGANISM: Homo sapiens
<220> FEATURE:
<223> OTHER INFORMATION: Antibody 07

<400> SEQUENCE: 62

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile His Gly Val Thr Arg Asn Trp Gly Gln Gly Thr
            100                 105                 110

Leu Val Thr Val Ser Ser
        115

<210> SEQ ID NO 63
<211> LENGTH: 5
<212> TYPE: PRT
<213> ORGANISM: Homo sapiens
<220> FEATURE:
<223> OTHER INFORMATION: Antibody 07

<400> SEQUENCE: 63

Ser Tyr Ala Met Ser
                5
```

<210> SEQ ID NO 64
<211> LENGTH: 17
<212> TYPE: PRT
<213> ORGANISM: Homo sapiens
<220> FEATURE:
<223> OTHER INFORMATION: Antibody 07

<400> SEQUENCE: 64

Ala Ile Ser Gly Ser Gly Gly Ser Thr Tyr Tyr Ala Asp Ser Val Lys
                5                   10                  15
Gly

<210> SEQ ID NO 65
<211> LENGTH: 9
<212> TYPE: PRT
<213> ORGANISM: Homo sapiens
<220> FEATURE:
<223> OTHER INFORMATION: Antibody 07

<400> SEQUENCE: 65

Asp Leu Ile His Gly Val Thr Arg Asn
                5

<210> SEQ ID NO 66
<211> LENGTH: 336
<212> TYPE: DNA
<213> ORGANISM: Homo sapiens
<220> FEATURE:
<223> OTHER INFORMATION: Antibody 07

<400> SEQUENCE: 66
aattttatgc tgactcagcc ccactctgtg tcggagtctc cggggaagac ggtaaccatc      60
tcctgcaccc gcagcagtgg cagccttgcc aactactatg tgcagtggta ccaacagcgc     120
ccgggcagtt cccccaccat tgtgatcttt gcgaataacc aaagaccctc tggggtccct     180
gatcgattct ctggctccat cgacagctcc tccaactctg cctccctcac catctctgga     240
ctgaagactg aggacgaggc tgactactac tgccagacgt acgaccccta cagcgtggtg     300
ttcggcggag ggaccaagct gaccgtccta ggtgag                              336

<210> SEQ ID NO 67
<211> LENGTH: 112
<212> TYPE: PRT
<213> ORGANISM: Homo sapiens
<220> FEATURE:
<223> OTHER INFORMATION: Antibody 07

<400> SEQUENCE: 67

Asn Phe Met Leu Thr Gln Pro His Ser Val Ser Glu Ser Pro Gly Lys
                5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ser Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Pro
                85                  90                  95

```
Tyr Ser Val Val Phe Gly Gly Gly Thr Lys Leu Thr Val Leu Gly Glu
            100                 105                 110
```

<210> SEQ ID NO 68
<211> LENGTH: 13
<212> TYPE: PRT
<213> ORGANISM: Homo sapiens
<220> FEATURE:
<223> OTHER INFORMATION: Antibody 07

<400> SEQUENCE: 68

```
Thr Arg Ser Ser Gly Ser Leu Ala Asn Tyr Tyr Val Gln
                  5                  10
```

<210> SEQ ID NO 69
<211> LENGTH: 7
<212> TYPE: PRT
<213> ORGANISM: Homo sapiens
<220> FEATURE:
<223> OTHER INFORMATION: Antibody 07

<400> SEQUENCE: 69

```
Ala Asn Asn Gln Arg Pro Ser
                  5
```

<210> SEQ ID NO 70
<211> LENGTH: 9
<212> TYPE: PRT
<213> ORGANISM: Homo sapiens
<220> FEATURE:
<223> OTHER INFORMATION: Antibody 07

<400> SEQUENCE: 70

```
Gln Thr Tyr Asp Pro Tyr Ser Val Val
                  5
```

<210> SEQ ID NO 71
<211> LENGTH: 354
<212> TYPE: DNA
<213> ORGANISM: Homo sapiens
<220> FEATURE:
<223> OTHER INFORMATION: Antibody 08

<400> SEQUENCE: 71

```
gaggtgcagc tgttggagtc tggggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc aagagatcta     300
atttggggag tggctgggag ctggggccag gggacaatgg tcaccgtctc ctca           354
```

<210> SEQ ID NO 72
<211> LENGTH: 118
<212> TYPE: PRT
<213> ORGANISM: Homo sapiens
<220> FEATURE:
<223> OTHER INFORMATION: Antibody 08

<400> SEQUENCE: 72

```
Glu Val Gln Leu Leu Glu Ser Gly Gly Gly Leu Val Gln Pro Gly Gly
                  5                  10                  15

Ser Leu Arg Leu Ser Cys Ala Ala Ser Gly Phe Thr Phe Ser Ser Tyr
             20                  25                  30
```

```
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile Trp Gly Val Ala Gly Ser Trp Gly Gln Gly Thr
            100                 105                 110

Met Val Thr Val Ser Ser
        115
```

<210> SEQ ID NO 73
<211> LENGTH: 5
<212> TYPE: PRT
<213> ORGANISM: Homo sapiens
<220> FEATURE:
<223> OTHER INFORMATION: Antibody 08

<400> SEQUENCE: 73

```
Ser Tyr Ala Met Ser
                5
```

<210> SEQ ID NO 74
<211> LENGTH: 17
<212> TYPE: PRT
<213> ORGANISM: Homo sapiens
<220> FEATURE:
<223> OTHER INFORMATION: Antibody 08

<400> SEQUENCE: 74

```
Ala Ile Ser Gly Ser Gly Gly Ser Thr Tyr Tyr Ala Asp Ser Val Lys
                5                   10                  15
Gly
```

<210> SEQ ID NO 75
<211> LENGTH: 9
<212> TYPE: PRT
<213> ORGANISM: Homo sapiens
<220> FEATURE:
<223> OTHER INFORMATION: Antibody 08

<400> SEQUENCE: 75

```
Asp Leu Ile Trp Gly Val Ala Gly Ser
                5
```

<210> SEQ ID NO 76
<211> LENGTH: 336
<212> TYPE: DNA
<213> ORGANISM: Homo sapiens
<220> FEATURE:
<223> OTHER INFORMATION: Antibody 08

<400> SEQUENCE: 76

```
aattttatgc tgactcagcc ccactctgtg tcggagtctc cggggaagac ggtaaccatc      60
tcctgcaccc gcagcagtgg cagccttgcc aactactatg tgcagtggta ccaacagcgc     120
ccgggcagtg cccccaccat tgtgatcttt gcgaataacc aaagaccctc tggggtccct     180
gatcgattct ctggctccat cgacagctcc tccaactctg cctccctcac catctctaga     240
ctgaagactg aggacgaggc tgactactac tgccagtctt ataaccacaa ggacatcgtg     300
```

```
ttcggcggag ggaccaagct gaccgtccta ggtgag                          336
```

<210> SEQ ID NO 77
<211> LENGTH: 112
<212> TYPE: PRT
<213> ORGANISM: Homo sapiens
<220> FEATURE:
<223> OTHER INFORMATION: Antibody 08

<400> SEQUENCE: 77

Asn Phe Met Leu Thr Gln Pro His Ser Val Ser Glu Ser Pro Gly Lys
                 5                  10                  15

Thr Val Thr Ile Ser Cys Thr Arg Ser Ser Gly Ser Leu Ala Asn Tyr
             20                  25                  30

Tyr Val Gln Trp Tyr Gln Gln Arg Pro Gly Ser Ala Pro Thr Ile Val
         35                  40                  45

Ile Phe Ala Asn Asn Gln Arg Pro Ser Gly Val Pro Asp Arg Phe Ser
     50                  55                  60

Gly Ser Ile Asp Ser Ser Ser Asn Ser Ala Ser Leu Thr Ile Ser Arg
 65                  70                  75                  80

Leu Lys Thr Glu Asp Glu Ala Asp Tyr Tyr Cys Gln Ser Tyr Asn His
                 85                  90                  95

Lys Asp Ile Val Phe Gly Gly Gly Thr Lys Leu Thr Val Leu Gly Glu
            100                 105                 110

<210> SEQ ID NO 78
<211> LENGTH: 13
<212> TYPE: PRT
<213> ORGANISM: Homo sapiens
<220> FEATURE:
<223> OTHER INFORMATION: Antibody 08

<400> SEQUENCE: 78

Thr Arg Ser Ser Gly Ser Leu Ala Asn Tyr Tyr Val Gln
                 5                  10

<210> SEQ ID NO 79
<211> LENGTH: 7
<212> TYPE: PRT
<213> ORGANISM: Homo sapiens
<220> FEATURE:
<223> OTHER INFORMATION: Antibody 08

<400> SEQUENCE: 79

Ala Asn Asn Gln Arg Pro Ser
                 5

<210> SEQ ID NO 80
<211> LENGTH: 9
<212> TYPE: PRT
<213> ORGANISM: Homo sapiens
<220> FEATURE:
<223> OTHER INFORMATION: Antibody 08

<400> SEQUENCE: 80

Gln Ser Tyr Asn His Lys Asp Ile Val
                 5

<210> SEQ ID NO 81
<211> LENGTH: 354
<212> TYPE: DNA
<213> ORGANISM: Homo sapiens
<220> FEATURE:

<223> OTHER INFORMATION: Antibody 09

<400> SEQUENCE: 81

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc aagagatcta   300
attttcgggg tggggggggg gtggggccag gggacaatgg tcaccgtctc ctca         354
```

<210> SEQ ID NO 82
<211> LENGTH: 118
<212> TYPE: PRT
<213> ORGANISM: Homo sapiens
<220> FEATURE:
<223> OTHER INFORMATION: Antibody 09

<400> SEQUENCE: 82

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Leu Ile Phe Gly Val Gly Gly Trp Gly Gln Gly Thr
            100                 105                 110
Met Val Thr Val Ser Ser
        115
```

<210> SEQ ID NO 83
<211> LENGTH: 5
<212> TYPE: PRT
<213> ORGANISM: Homo sapiens
<220> FEATURE:
<223> OTHER INFORMATION: Antibody 09

<400> SEQUENCE: 83

Ser Tyr Ala Met Ser
 1               5

<210> SEQ ID NO 84
<211> LENGTH: 17
<212> TYPE: PRT
<213> ORGANISM: Homo sapiens
<220> FEATURE:
<223> OTHER INFORMATION: Antibody 09

<400> SEQUENCE: 84

```
Ala Ile Ser Gly Ser Gly Gly Ser Thr Tyr Tyr Ala Asp Ser Val Lys
 1               5                  10                  15
Gly
```

```
<210> SEQ ID NO 85
<211> LENGTH: 9
<212> TYPE: PRT
<213> ORGANISM: Homo sapiens
<220> FEATURE:
<223> OTHER INFORMATION: Antibody 09

<400> SEQUENCE: 85

Asp Leu Ile Phe Gly Val Gly Gly Gly
                5

<210> SEQ ID NO 86
<211> LENGTH: 336
<212> TYPE: DNA
<213> ORGANISM: Homo sapiens
<220> FEATURE:
<223> OTHER INFORMATION: Antibody 09

<400> SEQUENCE: 86
aattttatgc tgactcagcc ccactctgtg tcggagtctc cggggaagac ggtaaccatc      60
tcctgcaccc gcagcagtgg cagccttgcc aactactatg tgcagtggta ccaacagcgc     120
ccgggcagtg cccccaccat tgtgatcttt gcgaataacc aaagaccctc tggggtccct     180
gatcgattct ctggctccat cgacagctcc tccaactctg cctccctcac catctctaga     240
ctgaagactg aggacgaggc tgactactac tgccagtcct actcccccca cagcgtggtg     300
ttcggcggag ggaccaagct gaccgtccta ggtgag                               336

<210> SEQ ID NO 87
<211> LENGTH: 112
<212> TYPE: PRT
<213> ORGANISM: Homo sapiens
<220> FEATURE:
<223> OTHER INFORMATION: Antibody 09

<400> SEQUENCE: 87

Asn Phe Met Leu Thr Gln Pro His Ser Val Ser Glu Ser Pro Gly Lys
                5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Ser Pro
                85                  90                  95

His Ser Val Val Phe Gly Gly Gly Thr Lys Leu Thr Val Leu Gly Glu
            100                 105                 110

<210> SEQ ID NO 88
<211> LENGTH: 13
<212> TYPE: PRT
<213> ORGANISM: Homo sapiens
<220> FEATURE:
<223> OTHER INFORMATION: Antibody 09

<400> SEQUENCE: 88

Thr Arg Ser Ser Gly Ser Leu Ala Asn Tyr Tyr Val Gln
                5                   10
```

-continued

```
<210> SEQ ID NO 89
<211> LENGTH: 7
<212> TYPE: PRT
<213> ORGANISM: Homo sapiens
<220> FEATURE:
<223> OTHER INFORMATION: Antibody 09

<400> SEQUENCE: 89

Ala Asn Asn Gln Arg Pro Ser
              5

<210> SEQ ID NO 90
<211> LENGTH: 9
<212> TYPE: PRT
<213> ORGANISM: Homo sapiens
<220> FEATURE:
<223> OTHER INFORMATION: Antibody 09

<400> SEQUENCE: 90

Gln Ser Tyr Ser Pro His Ser Val Val
              5

<210> SEQ ID NO 91
<211> LENGTH: 354
<212> TYPE: DNA
<213> ORGANISM: Homo sapiens
<220> FEATURE:
<223> OTHER INFORMATION: Antibody 10

<400> SEQUENCE: 91
gaggtgcagc tgttggagtc tgggggaggc ttggtacagc ctgggggtc cctgagactc       60 tcctgtgcag cctctggatt cacctttagc agctatgcca tgagctgggt ccgccaggct     120
ccagggaagg gctggagtg gtctcagct attagtggta gtggtggtag cacatactac       180
gcagactccg tgaagggccg gttcaccatc tccagagaca attccaagaa cacgctgtat    240
ctgcaaatga acagcctgag agccgaggac acggccgtgt attactgtgc aagagatcta    300
attttcgggg tggggggggg gtggggccag gggacaatgg tcaccgtctc ctca          354

<210> SEQ ID NO 92
<211> LENGTH: 118
<212> TYPE: PRT
<213> ORGANISM: Homo sapiens
<220> FEATURE:
<223> OTHER INFORMATION: Antibody 10

<400> SEQUENCE: 92

Glu Val Gln Leu Leu Glu Ser Gly Gly Gly Leu Val Gln Pro Gly Gly
                5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Asp Leu Ile Phe Gly Val Gly Gly Gly Trp Gly Gln Gly Thr
            100                 105                 110

Met Val Thr Val Ser Ser
```

<210> SEQ ID NO 93
<211> LENGTH: 5
<212> TYPE: PRT
<213> ORGANISM: Homo sapiens
<220> FEATURE:
<223> OTHER INFORMATION: Antibody 10

<400> SEQUENCE: 93

Ser Tyr Ala Met Ser
              5

<210> SEQ ID NO 94
<211> LENGTH: 17
<212> TYPE: PRT
<213> ORGANISM: Homo sapiens
<220> FEATURE:
<223> OTHER INFORMATION: Antibody 10

<400> SEQUENCE: 94

Ala Ile Ser Gly Ser Gly Gly Ser Thr Tyr Tyr Ala Asp Ser Val Lys
                 5                  10                  15

Gly

<210> SEQ ID NO 95
<211> LENGTH: 9
<212> TYPE: PRT
<213> ORGANISM: Homo sapiens
<220> FEATURE:
<223> OTHER INFORMATION: Antibody 10

<400> SEQUENCE: 95

Asp Leu Ile Phe Gly Val Gly Gly Gly
              5

<210> SEQ ID NO 96
<211> LENGTH: 336
<212> TYPE: DNA
<213> ORGANISM: Homo sapiens
<220> FEATURE:
<223> OTHER INFORMATION: Antibody 10

<400> SEQUENCE: 96
aattttatgc tgactcagcc ccactctgtg tcggagtctc cggggaagac ggtaaccatc      60
tcctgcaccc gcagcagtgg cagccttgcc aactactatg tgcagtggta ccaacagcgc     120
ccgggcagtg cccccaccat tgtgatcttt gcgaataacc aaagaccctc tggggtccct     180
gatcgattct ctggctccat cgacagctcc tccaactctg cctccctcac catctctaga     240
ctgaagactg aggacgaggc tgactactac tgccagtcgt acgaccccca cagcgtggtg     300
ttcggcggag ggaccaagct gaccgtccta ggtgag                              336

<210> SEQ ID NO 97
<211> LENGTH: 112
<212> TYPE: PRT
<213> ORGANISM: Homo sapiens
<220> FEATURE:
<223> OTHER INFORMATION: Antibody 10

<400> SEQUENCE: 97

Asn Phe Met Leu Thr Gln Pro His Ser Val Ser Glu Ser Pro Gly Lys
                 5                  10                  15

Thr Val Thr Ile Ser Cys Thr Arg Ser Ser Gly Ser Leu Ala Asn Tyr

```
                        20                  25                  30
Tyr Val Gln Trp Tyr Gln Gln Arg Pro Gly Ser Ala Pro Thr Ile Val
            35                  40                  45

Ile Phe Ala Asn Asn Gln Arg Pro Ser Gly Val Pro Asp Arg Phe Ser
        50                  55                  60

Gly Ser Ile Asp Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Asp Pro
                85                  90                  95

His Ser Val Val Phe Gly Gly Gly Thr Lys Leu Thr Val Leu Gly Glu
            100                 105                 110

<210> SEQ ID NO 98
<211> LENGTH: 13
<212> TYPE: PRT
<213> ORGANISM: Homo sapiens
<220> FEATURE:
<223> OTHER INFORMATION: Antibody 10

<400> SEQUENCE: 98

Thr Arg Ser Ser Gly Ser Leu Ala Asn Tyr Tyr Val Gln
                5                   10

<210> SEQ ID NO 99
<211> LENGTH: 7
<212> TYPE: PRT
<213> ORGANISM: Homo sapiens
<220> FEATURE:
<223> OTHER INFORMATION: Antibody 10

<400> SEQUENCE: 99

Ala Asn Asn Gln Arg Pro Ser
                5

<210> SEQ ID NO 100
<211> LENGTH: 9
<212> TYPE: PRT
<213> ORGANISM: Homo sapiens
<220> FEATURE:
<223> OTHER INFORMATION: Antibody 10

<400> SEQUENCE: 100

Gln Ser Tyr Asp Pro His Ser Val Val
                5

<210> SEQ ID NO 101
<211> LENGTH: 354
<212> TYPE: DNA
<213> ORGANISM: Homo sapiens
<220> FEATURE:
<223> OTHER INFORMATION: Antibody 11

<400> SEQUENCE: 101
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggccgtgt attactgtgc aagagatcta     300
atttggggag tggctgggag ctggggccag gggacaatgg tcaccgtctc ctca           354
```

```
<210> SEQ ID NO 102
<211> LENGTH: 118
<212> TYPE: PRT
<213> ORGANISM: Homo sapiens
<220> FEATURE:
<223> OTHER INFORMATION: Antibody 11

<400> SEQUENCE: 102

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Ile Trp Gly Val Ala Gly Ser Trp Gly Gln Gly Thr
            100                 105                 110

Met Val Thr Val Ser Ser
        115

<210> SEQ ID NO 103
<211> LENGTH: 5
<212> TYPE: PRT
<213> ORGANISM: Homo sapiens
<220> FEATURE:
<223> OTHER INFORMATION: Antibody 11

<400> SEQUENCE: 103

Ser Tyr Ala Met Ser
                 5

<210> SEQ ID NO 104
<211> LENGTH: 17
<212> TYPE: PRT
<213> ORGANISM: Homo sapiens
<220> FEATURE:
<223> OTHER INFORMATION: Antibody 11

<400> SEQUENCE: 104

Ala Ile Ser Gly Ser Gly Gly Ser Thr Tyr Tyr Ala Asp Ser Val Lys
                 5                  10                  15

Gly

<210> SEQ ID NO 105
<211> LENGTH: 9
<212> TYPE: PRT
<213> ORGANISM: Homo sapiens
<220> FEATURE:
<223> OTHER INFORMATION: Antibody 11

<400> SEQUENCE: 105

Asp Leu Ile Trp Gly Val Ala Gly Ser
                 5

<210> SEQ ID NO 106
<211> LENGTH: 336
<212> TYPE: DNA
<213> ORGANISM: Homo sapiens
```

<220> FEATURE:
<223> OTHER INFORMATION: Antibody 11

<400> SEQUENCE: 106

```
aattttatgc tgactcagcc ccactctgtg tcggagtctc cggggaagac ggtaaccatc    60
tcctgcaccc gcagcagtgg cagccttgcc aactactatg tgcagtggta ccaacagcgc   120
ccgggcagtg cccccaccat tgtgatcttt gcgaataacc aaagaccctc tggggtccct   180
gatcgattct ctggctccat cgacagctcc tccaactctg cctccctcac catctctaga   240
ctgaagactg aggacgaggc tgactactac tgccagtcct actcccccca cagcgtggtg   300
ttcggcggag ggaccaagct gaccgtccta ggtgag                             336
```

<210> SEQ ID NO 107
<211> LENGTH: 112
<212> TYPE: PRT
<213> ORGANISM: Homo sapiens
<220> FEATURE:
<223> OTHER INFORMATION: Antibody 11

<400> SEQUENCE: 107

```
Asn Phe Met Leu Thr Gln Pro His Ser Val Ser Glu Ser Pro Gly Lys
              5                  10                  15

Thr Val Thr Ile Ser Cys Thr Arg Ser Ser Gly Ser Leu Ala Asn Tyr
         20                  25                  30

Tyr Val Gln Trp Tyr Gln Gln Arg Pro Gly Ser Ala Pro Thr Ile Val
     35                  40                  45

Ile Phe Ala Asn Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Arg
 65                  70                  75                  80

Leu Lys Thr Glu Asp Glu Ala Asp Tyr Tyr Cys Gln Ser Tyr Ser Pro
             85                  90                  95

His Ser Val Val Phe Gly Gly Gly Thr Lys Leu Thr Val Leu Gly Glu
            100                 105                 110
```

<210> SEQ ID NO 108
<211> LENGTH: 13
<212> TYPE: PRT
<213> ORGANISM: Homo sapiens
<220> FEATURE:
<223> OTHER INFORMATION: Antibody 11

<400> SEQUENCE: 108

```
Thr Arg Ser Ser Gly Ser Leu Ala Asn Tyr Tyr Val Gln
              5                  10
```

<210> SEQ ID NO 109
<211> LENGTH: 7
<212> TYPE: PRT
<213> ORGANISM: Homo sapiens
<220> FEATURE:
<223> OTHER INFORMATION: Antibody 11

<400> SEQUENCE: 109

```
Ala Asn Asn Gln Arg Pro Ser
              5
```

<210> SEQ ID NO 110
<211> LENGTH: 9
<212> TYPE: PRT
<213> ORGANISM: Homo sapiens

```
<220> FEATURE:
<223> OTHER INFORMATION: Antibody 11

<400> SEQUENCE: 110

Gln Ser Tyr Ser Pro His Ser Val Val
                5

<210> SEQ ID NO 111
<211> LENGTH: 354
<212> TYPE: DNA
<213> ORGANISM: Homo sapiens
<220> FEATURE:
<223> OTHER INFORMATION: Antibody 12

<400> SEQUENCE: 111
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat   240
ctgcaaatga acagcctgag agccgaggac acggccgtgt attactgtgc aagagatcta   300
attttcgggg tggggggggg gtggggccag gggacaatgg tcaccgtctc ctca         354

<210> SEQ ID NO 112
<211> LENGTH: 118
<212> TYPE: PRT
<213> ORGANISM: Homo sapiens
<220> FEATURE:
<223> OTHER INFORMATION: Antibody 12

<400> SEQUENCE: 112

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Asp Leu Ile Phe Gly Val Gly Gly Gly Trp Gly Gln Gly Thr
            100                 105                 110

Met Val Thr Val Ser Ser
        115

<210> SEQ ID NO 113
<211> LENGTH: 5
<212> TYPE: PRT
<213> ORGANISM: Homo sapiens
<220> FEATURE:
<223> OTHER INFORMATION: Antibody 12

<400> SEQUENCE: 113

Ser Tyr Ala Met Ser
                5

<210> SEQ ID NO 114
```

<210> SEQ ID NO 114
<211> LENGTH: 17
<212> TYPE: PRT
<213> ORGANISM: Homo sapiens
<220> FEATURE:
<223> OTHER INFORMATION: Antibody 12

<400> SEQUENCE: 114

Ala Ile Ser Gly Ser Gly Gly Ser Thr Tyr Tyr Ala Asp Ser Val Lys
                5                   10                  15
Gly

<210> SEQ ID NO 115
<211> LENGTH: 9
<212> TYPE: PRT
<213> ORGANISM: Homo sapiens
<220> FEATURE:
<223> OTHER INFORMATION: Antibody 12

<400> SEQUENCE: 115

Asp Leu Ile Phe Gly Val Gly Gly Gly
                5

<210> SEQ ID NO 116
<211> LENGTH: 336
<212> TYPE: DNA
<213> ORGANISM: Homo sapiens
<220> FEATURE:
<223> OTHER INFORMATION: Antibody 12

<400> SEQUENCE: 116
aattttatgc tgactcagcc ccactctgtg tcggagtctc cggggaagac ggtaaccatc     60
tcctgcaccc gcagcagtgg cagccttgcc aactactatg tgcagtggta ccaacagcgc    120
ccgggcagtg cccccaccat tgtgatcttt gcgaataacc aaagaccctc tggggtccct    180
gatcgattct ctggctccat cgacagctcc tccaactctg cctccctcac catctctaga    240
ctgaagactg aggacgaggc tgactactac tgccagacgt acgaccccta cagcgtggtg    300
ttcggcggag ggaccaagct gaccgtccta ggtgag                              336

<210> SEQ ID NO 117
<211> LENGTH: 112
<212> TYPE: PRT
<213> ORGANISM: Homo sapiens
<220> FEATURE:
<223> OTHER INFORMATION: Antibody 12

<400> SEQUENCE: 117

Asn Phe Met Leu Thr Gln Pro His Ser Val Ser Glu Ser Pro Gly Lys
                5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Arg
65                  70                  75                  80

Leu Lys Thr Glu Asp Glu Ala Asp Tyr Tyr Cys Gln Thr Tyr Asp Pro
                85                  90                  95

Tyr Ser Val Val Phe Gly Gly Thr Lys Leu Thr Val Leu Gly Glu
            100                 105                 110

<210> SEQ ID NO 118
<211> LENGTH: 13
<212> TYPE: PRT
<213> ORGANISM: Homo sapiens
<220> FEATURE:
<223> OTHER INFORMATION: Antibody 12

<400> SEQUENCE: 118

Thr Arg Ser Ser Gly Ser Leu Ala Asn Tyr Tyr Val Gln
                5                   10

<210> SEQ ID NO 119
<211> LENGTH: 7
<212> TYPE: PRT
<213> ORGANISM: Homo sapiens
<220> FEATURE:
<223> OTHER INFORMATION: Antibody 12

<400> SEQUENCE: 119

Ala Asn Asn Gln Arg Pro Ser
                5

<210> SEQ ID NO 120
<211> LENGTH: 9
<212> TYPE: PRT
<213> ORGANISM: Homo sapiens
<220> FEATURE:
<223> OTHER INFORMATION: Antibody 12

<400> SEQUENCE: 120

Gln Thr Tyr Asp Pro Tyr Ser Val Val
                5

<210> SEQ ID NO 121
<211> LENGTH: 354
<212> TYPE: DNA
<213> ORGANISM: Homo sapiens
<220> FEATURE:
<223> OTHER INFORMATION: Antibody 13

<400> SEQUENCE: 121
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc aagagatcta     300
atttggggag tggctgggag ctggggccag gggacactgg tcaccgtctc ctca           354

<210> SEQ ID NO 122
<211> LENGTH: 118
<212> TYPE: PRT
<213> ORGANISM: Homo sapiens
<220> FEATURE:
<223> OTHER INFORMATION: Antibody 13

<400> SEQUENCE: 122

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

```
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Ile Trp Gly Val Ala Gly Ser Trp Gly Gln Gly Thr
            100                 105                 110

Leu Val Thr Val Ser Ser
        115

<210> SEQ ID NO 123
<211> LENGTH: 5
<212> TYPE: PRT
<213> ORGANISM: Homo sapiens
<220> FEATURE:
<223> OTHER INFORMATION: Antibody 13

<400> SEQUENCE: 123

Ser Tyr Ala Met Ser
                5

<210> SEQ ID NO 124
<211> LENGTH: 17
<212> TYPE: PRT
<213> ORGANISM: Homo sapiens
<220> FEATURE:
<223> OTHER INFORMATION: Antibody 13

<400> SEQUENCE: 124

Ala Ile Ser Gly Ser Gly Gly Ser Thr Tyr Tyr Ala Asp Ser Val Lys
                5                   10                  15

Gly

<210> SEQ ID NO 125
<211> LENGTH: 9
<212> TYPE: PRT
<213> ORGANISM: Homo sapiens
<220> FEATURE:
<223> OTHER INFORMATION: Antibody 13

<400> SEQUENCE: 125

Asp Leu Ile Trp Gly Val Ala Gly Ser
                5

<210> SEQ ID NO 126
<211> LENGTH: 336
<212> TYPE: DNA
<213> ORGANISM: Homo sapiens
<220> FEATURE:
<223> OTHER INFORMATION: Antibody 13

<400> SEQUENCE: 126
aattttatgc tgactcagcc ccactctgtg tcggagtctc cggggaagac ggtaaccatc    60
tcctgcaccc gcagcagtgg cagccttgcc aactactatg tgcagtggta ccaacagcgc   120
ccgggcagtg cccccaccat tgtgatcttt gcgaataacc aaagaccctc tggggtccct   180
gatcgattct ctggctccat cgacagctcc tccaactctg cctccctcac catctctaga   240
ctgaagactg aggacgaggc tgactactac tgccagtctt atgacccgcg ggtggtcgtg   300
ttcggcggag ggaccaagct gaccgtccta ggtgag                             336
```

<210> SEQ ID NO 127
<211> LENGTH: 112
<212> TYPE: PRT
<213> ORGANISM: Homo sapiens
<220> FEATURE:
<223> OTHER INFORMATION: Antibody 13

<400> SEQUENCE: 127

Asn Phe Met Leu Thr Gln Pro His Ser Val Ser Glu Ser Pro Gly Lys
                 5                  10                  15

Thr Val Thr Ile Ser Cys Thr Arg Ser Ser Gly Ser Leu Ala Asn Tyr
             20                  25                  30

Tyr Val Gln Trp Tyr Gln Arg Pro Gly Ser Ala Pro Thr Ile Val
         35                  40                  45

Ile Phe Ala Asn Asn Gln Arg Pro Ser Gly Val Pro Asp Arg Phe Ser
     50                  55                  60

Gly Ser Ile Asp Ser Ser Asn Ser Ala Ser Leu Thr Ile Ser Arg
 65                  70                  75                  80

Leu Lys Thr Glu Asp Glu Ala Asp Tyr Tyr Cys Gln Ser Tyr Asp Pro
                 85                  90                  95

Arg Val Val Val Phe Gly Gly Gly Thr Lys Leu Thr Val Leu Gly Glu
            100                 105                 110

<210> SEQ ID NO 128
<211> LENGTH: 13
<212> TYPE: PRT
<213> ORGANISM: Homo sapiens
<220> FEATURE:
<223> OTHER INFORMATION: Antibody 13

<400> SEQUENCE: 128

Thr Arg Ser Ser Gly Ser Leu Ala Asn Tyr Tyr Val Gln
                 5                  10

<210> SEQ ID NO 129
<211> LENGTH: 7
<212> TYPE: PRT
<213> ORGANISM: Homo sapiens
<220> FEATURE:
<223> OTHER INFORMATION: Antibody 13

<400> SEQUENCE: 129

Ala Asn Asn Gln Arg Pro Ser
                 5

<210> SEQ ID NO 130
<211> LENGTH: 9
<212> TYPE: PRT
<213> ORGANISM: Homo sapiens
<220> FEATURE:
<223> OTHER INFORMATION: Antibody 13

<400> SEQUENCE: 130

Gln Ser Tyr Asp Pro Arg Val Val Val
                 5

<210> SEQ ID NO 131
<211> LENGTH: 354
<212> TYPE: DNA
<213> ORGANISM: Homo sapiens
<220> FEATURE:
<223> OTHER INFORMATION: Antibody 14

<400> SEQUENCE: 131

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc aagagatcta   300
atttggggag tggctgggag ctggggccag gggacactgg tcaccgtctc ctca         354
```

<210> SEQ ID NO 132
<211> LENGTH: 118
<212> TYPE: PRT
<213> ORGANISM: Homo sapiens
<220> FEATURE:
<223> OTHER INFORMATION: Antibody 14

<400> SEQUENCE: 132

Glu Val Gln Leu Leu Glu Ser Gly Gly Gly Leu Val Gln Pro Gly Gly
              5                   10                  15

Ser Leu Arg Leu Ser Cys Ala Ala Ser Gly Phe Thr Phe Ser Ser Tyr
         20                   25                  30

Ala Met Ser Trp Val Arg Gln Ala Pro Gly Lys Gly Leu Glu Trp Val
     35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Asp Leu Ile Trp Gly Val Ala Gly Ser Trp Gly Gln Gly Thr
            100                 105                 110

Leu Val Thr Val Ser Ser
        115

<210> SEQ ID NO 133
<211> LENGTH: 5
<212> TYPE: PRT
<213> ORGANISM: Homo sapiens
<220> FEATURE:
<223> OTHER INFORMATION: Antibody 14

<400> SEQUENCE: 133

Ser Tyr Ala Met Ser
              5

<210> SEQ ID NO 134
<211> LENGTH: 17
<212> TYPE: PRT
<213> ORGANISM: Homo sapiens
<220> FEATURE:
<223> OTHER INFORMATION: Antibody 14

<400> SEQUENCE: 134

Ala Ile Ser Gly Ser Gly Gly Ser Thr Tyr Tyr Ala Asp Ser Val Lys
              5                   10                  15

Gly

<210> SEQ ID NO 135
<211> LENGTH: 9
<212> TYPE: PRT

<213> ORGANISM: Homo sapiens
<220> FEATURE:
<223> OTHER INFORMATION: Antibody 14

<400> SEQUENCE: 135

Asp Leu Ile Trp Gly Val Ala Gly Ser
              5

<210> SEQ ID NO 136
<211> LENGTH: 336
<212> TYPE: DNA
<213> ORGANISM: Homo sapiens
<220> FEATURE:
<223> OTHER INFORMATION: Antibody 14

<400> SEQUENCE: 136

```
aattttatgc tgactcagcc ccactctgtg tcggagtctc cggggaagac ggtaaccatc      60
tcctgcaccc gcagcagtgg cagccttgcc aactactatg tgcagtggta ccaacagcgc     120
ccgggcagtg cccccaccat tgtgatcttt gcgaataacc aaagaccctc tggggtccct     180
gatcgattct ctggctccat cgacagctcc tccaactctg cctccctcac catctctaga     240
ctgaagactg aggacgaggc tgactactac tgccagtctt atgacccgac gaaccaggtg     300
ttcggcggag ggaccaagct gaccgtccta ggtgag                              336
```

<210> SEQ ID NO 137
<211> LENGTH: 112
<212> TYPE: PRT
<213> ORGANISM: Homo sapiens
<220> FEATURE:
<223> OTHER INFORMATION: Antibody 14

<400> SEQUENCE: 137

Asn Phe Met Leu Thr Gln Pro His Ser Val Ser Glu Ser Pro Gly Lys
              5                  10                  15

Thr Val Thr Ile Ser Cys Thr Arg Ser Ser Gly Ser Leu Ala Asn Tyr
         20                  25                  30

Tyr Val Gln Trp Tyr Gln Gln Arg Pro Gly Ser Ala Pro Thr Ile Val
     35                  40                  45

Ile Phe Ala Asn Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Asp Pro
             85                  90                  95

Thr Asn Gln Val Phe Gly Gly Gly Thr Lys Leu Thr Val Leu Gly Glu
            100                 105                 110

<210> SEQ ID NO 138
<211> LENGTH: 13
<212> TYPE: PRT
<213> ORGANISM: Homo sapiens
<220> FEATURE:
<223> OTHER INFORMATION: Antibody 14

<400> SEQUENCE: 138

Thr Arg Ser Ser Gly Ser Leu Ala Asn Tyr Tyr Val Gln
              5                  10

<210> SEQ ID NO 139
<211> LENGTH: 7
<212> TYPE: PRT

```
<213> ORGANISM: Homo sapiens
<220> FEATURE:
<223> OTHER INFORMATION: Antibody 14

<400> SEQUENCE: 139

Ala Asn Asn Gln Arg Pro Ser
                5

<210> SEQ ID NO 140
<211> LENGTH: 9
<212> TYPE: PRT
<213> ORGANISM: Homo sapiens
<220> FEATURE:
<223> OTHER INFORMATION: Antibody 14

<400> SEQUENCE: 140

Gln Ser Tyr Asp Pro Thr Asn Gln Val
                5

<210> SEQ ID NO 141
<211> LENGTH: 354
<212> TYPE: DNA
<213> ORGANISM: Homo sapiens
<220> FEATURE:
<223> OTHER INFORMATION: Antibody 15

<400> SEQUENCE: 141
gaggtgcagc tgttggagtc tgggggaggc ttggtacagc ctggggggtc cctgagactc      60
tcctgtgcag cctctggatt caccttcagc agctatgcca tgagctgggt ccgccaggct     120
ccagggaagg gcctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc aagagatcta     300
atttggggag tggctgggag ctggggccag gggacactgg tcaccgtctc ctca           354

<210> SEQ ID NO 142
<211> LENGTH: 118
<212> TYPE: PRT
<213> ORGANISM: Homo sapiens
<220> FEATURE:
<223> OTHER INFORMATION: Antibody 15

<400> SEQUENCE: 142

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Ile Trp Gly Val Ala Gly Ser Trp Gly Gln Gly Thr
            100                 105                 110

Leu Val Thr Val Ser Ser
        115
```

-continued

<210> SEQ ID NO 143
<211> LENGTH: 5
<212> TYPE: PRT
<213> ORGANISM: Homo sapiens
<220> FEATURE:
<223> OTHER INFORMATION: Antibody 15

<400> SEQUENCE: 143

Ser Tyr Ala Met Ser
            5

<210> SEQ ID NO 144
<211> LENGTH: 17
<212> TYPE: PRT
<213> ORGANISM: Homo sapiens
<220> FEATURE:
<223> OTHER INFORMATION: Antibody 15

<400> SEQUENCE: 144

Ala Ile Ser Gly Ser Gly Gly Ser Thr Tyr Tyr Ala Asp Ser Val Lys
            5                   10                  15

Gly

<210> SEQ ID NO 145
<211> LENGTH: 9
<212> TYPE: PRT
<213> ORGANISM: Homo sapiens
<220> FEATURE:
<223> OTHER INFORMATION: Antibody 15

<400> SEQUENCE: 145

Asp Leu Ile Trp Gly Val Ala Gly Ser
            5

<210> SEQ ID NO 146
<211> LENGTH: 336
<212> TYPE: DNA
<213> ORGANISM: Homo sapiens
<220> FEATURE:
<223> OTHER INFORMATION: Antibody 15

<400> SEQUENCE: 146
aattttatgc tgactcagcc ccactctgtg tcggagtctc cggggaagac ggtaaccatc      60
tcctgcaccc gcagcagtgg cagccttgcc aactactatg tgcagtgta ccaacagcgc     120 ccgggcagtg cccccaccat tgtgatcttt gcgaataacc aaagaccctc tggggtccct     180
gatcgattct ctggctccat cgacagctcc tccaactctg cctccctcac catctctaga     240
ctgaagactg aggacgaggc tgactactac tgccagtcct actccccgac gagcgtggtg     300
ttcggcggag ggaccaagct gaccgtccta ggtgag                              336

<210> SEQ ID NO 147
<211> LENGTH: 112
<212> TYPE: PRT
<213> ORGANISM: Homo sapiens
<220> FEATURE:
<223> OTHER INFORMATION: Antibody 15

<400> SEQUENCE: 147

Asn Phe Met Leu Thr Gln Pro His Ser Val Ser Glu Ser Pro Gly Lys
            5                   10                  15

Thr Val Thr Ile Ser Cys Thr Arg Ser Ser Gly Ser Leu Ala Asn Tyr
        20                  25                  30

Tyr Val Gln Trp Tyr Gln Gln Arg Pro Gly Ser Ala Pro Thr Ile Val

```
            35                  40                  45
Ile Phe Ala Asn Asn Gln Arg Pro Ser Gly Val Pro Asp Arg Phe Ser
        50                  55                  60
Gly Ser Ile Asp Ser Ser Asn Ser Ala Ser Leu Thr Ile Ser Arg
65                  70                  75                  80
Leu Lys Thr Glu Asp Glu Ala Asp Tyr Tyr Cys Gln Ser Tyr Ser Pro
                85                  90                  95
Thr Ser Val Val Phe Gly Gly Gly Thr Lys Leu Thr Val Leu Gly Glu
            100                 105                 110
```

<210> SEQ ID NO 148
<211> LENGTH: 13
<212> TYPE: PRT
<213> ORGANISM: Homo sapiens
<220> FEATURE:
<223> OTHER INFORMATION: Antibody 15

<400> SEQUENCE: 148

```
Thr Arg Ser Ser Gly Ser Leu Ala Asn Tyr Tyr Val Gln
                5                   10
```

<210> SEQ ID NO 149
<211> LENGTH: 7
<212> TYPE: PRT
<213> ORGANISM: Homo sapiens
<220> FEATURE:
<223> OTHER INFORMATION: Antibody 15

<400> SEQUENCE: 149

```
Ala Asn Asn Gln Arg Pro Ser
                5
```

<210> SEQ ID NO 150
<211> LENGTH: 9
<212> TYPE: PRT
<213> ORGANISM: Homo sapiens
<220> FEATURE:
<223> OTHER INFORMATION: Antibody 15

<400> SEQUENCE: 150

```
Gln Ser Tyr Ser Pro Thr Ser Val Val
                5
```

<210> SEQ ID NO 151
<211> LENGTH: 354
<212> TYPE: DNA
<213> ORGANISM: Homo sapiens
<220> FEATURE:
<223> OTHER INFORMATION: Antibody 16

<400> SEQUENCE: 151

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc aagagatcta     300
atttggggag tggctgggag ctggggccag gggacaatgg tcaccgtctc ctca           354
```

<210> SEQ ID NO 152
<211> LENGTH: 118
<212> TYPE: PRT

```
<213> ORGANISM: Homo sapiens
<220> FEATURE:
<223> OTHER INFORMATION: Antibody 16

<400> SEQUENCE: 152
```

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asp Leu Ile Trp Gly Val Ala Gly Ser Trp Gly Gln Gly Thr
            100                 105                 110

Met Val Thr Val Ser Ser
        115

```
<210> SEQ ID NO 153
<211> LENGTH: 5
<212> TYPE: PRT
<213> ORGANISM: Homo sapiens
<220> FEATURE:
<223> OTHER INFORMATION: Antibody 16

<400> SEQUENCE: 153
```

Ser Tyr Ala Met Ser
                 5

```
<210> SEQ ID NO 154
<211> LENGTH: 17
<212> TYPE: PRT
<213> ORGANISM: Homo sapiens
<220> FEATURE:
<223> OTHER INFORMATION: Antibody 16

<400> SEQUENCE: 154
```

Ala Ile Ser Gly Ser Gly Gly Ser Thr Tyr Tyr Ala Asp Ser Val Lys
                 5                  10                  15

Gly

```
<210> SEQ ID NO 155
<211> LENGTH: 9
<212> TYPE: PRT
<213> ORGANISM: Homo sapiens
<220> FEATURE:
<223> OTHER INFORMATION: Antibody 16

<400> SEQUENCE: 155
```

Asp Leu Ile Trp Gly Val Ala Gly Ser
                 5

```
<210> SEQ ID NO 156
<211> LENGTH: 336
<212> TYPE: DNA
<213> ORGANISM: Homo sapiens
<220> FEATURE:
<223> OTHER INFORMATION: Antibody 16
```

-continued

<400> SEQUENCE: 156

```
aattttatgc tgactcagcc ccactctgtg tcggagtctc cggggaagac ggtaaccatc    60
tcctgcaccc gcagcagtgg cagccttgcc aactactatg tgcagtggta ccaacagcgc   120
ccgggcagtg cccccaccat tgtgatcttt gcgaataacc aaagaccctc tggggtccct   180
gatcgattct ctggctccat cgacagctcc tccaactctg cctccctcac catctctaga   240
ctgaagactg aggacgaggc tgactactac tgccagacgt acgacccta cagcgtggtg    300
ttcggcggag ggaccaagct gaccgtccta ggtgag                            336
```

<210> SEQ ID NO 157
<211> LENGTH: 112
<212> TYPE: PRT
<213> ORGANISM: Homo sapiens
<220> FEATURE:
<223> OTHER INFORMATION: Antibody 16

<400> SEQUENCE: 157

Asn Phe Met Leu Thr Gln Pro His Ser Val Ser Glu Ser Pro Gly Lys
                 5                  10                  15

Thr Val Thr Ile Ser Cys Thr Arg Ser Ser Gly Ser Leu Ala Asn Tyr
             20                  25                  30

Tyr Val Gln Trp Tyr Gln Gln Arg Pro Gly Ser Ala Pro Thr Ile Val
         35                  40                  45

Ile Phe Ala Asn Asn Gln Arg Pro Ser Gly Val Pro Asp Arg Phe Ser
     50                  55                  60

Gly Ser Ile Asp Ser Ser Ser Asn Ser Ala Ser Leu Thr Ile Ser Arg
 65                  70                  75                  80

Leu Lys Thr Glu Asp Glu Ala Asp Tyr Tyr Cys Gln Thr Tyr Asp Pro
                 85                  90                  95

Tyr Ser Val Val Phe Gly Gly Gly Thr Lys Leu Thr Val Leu Gly Glu
            100                 105                 110

<210> SEQ ID NO 158
<211> LENGTH: 13
<212> TYPE: PRT
<213> ORGANISM: Homo sapiens
<220> FEATURE:
<223> OTHER INFORMATION: Antibody 16

<400> SEQUENCE: 158

Thr Arg Ser Ser Gly Ser Leu Ala Asn Tyr Tyr Val Gln
                 5                  10

<210> SEQ ID NO 159
<211> LENGTH: 7
<212> TYPE: PRT
<213> ORGANISM: Homo sapiens
<220> FEATURE:
<223> OTHER INFORMATION: Antibody 16

<400> SEQUENCE: 159

Ala Asn Asn Gln Arg Pro Ser
                 5

<210> SEQ ID NO 160
<211> LENGTH: 9
<212> TYPE: PRT
<213> ORGANISM: Homo sapiens
<220> FEATURE:
<223> OTHER INFORMATION: Antibody 16

<400> SEQUENCE: 160

Gln Thr Tyr Asp Pro Tyr Ser Val Val
1               5

<210> SEQ ID NO 161
<211> LENGTH: 466
<212> TYPE: DNA
<213> ORGANISM: Macaca fascicularis

<400> SEQUENCE: 161

```
atgactcctg ggaagaccct cattggtgcta ctgctgctgc tgctgagcct ggaggccata    60
gtgaaggcag aatagcaat cccacgaaat tcaggatgcc caaattccga ggacaagaac   120
ttcccccgga ctgtgatggt caacctgaac atccataacc ggaataccag taccaatccc   180
aaaaggtcct cagattacta caaccgatcc acctcacctt ggaatctcca ccgcaatgag   240
gaccctgaga gatatccctc tgtgatctgg gaggcaaaat gccgccactt aggctgcgtc   300
aaggctgatg gaacgtaga ctaccacatg aactctgtcc ccatccagca agagatcctg   360
gtcctgcgca gggagcctcg gcactgcccc aactccttcc ggctggagaa gatactggtg   420
tccgtgggct gcacctgtgt cacccccatt gtccaccatg tagcct                  466
```

<210> SEQ ID NO 162
<211> LENGTH: 155
<212> TYPE: PRT
<213> ORGANISM: Macaca fascicularis

<400> SEQUENCE: 162

Met Thr Pro Gly Lys Thr Ser Leu Val Leu Leu Leu Leu Leu Leu Ser
1               5                   10                  15

Leu Glu Ala Ile Val Lys Ala Gly Ile Ala Ile Pro Arg Asn Ser Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Ser Thr Asn Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Val Lys Ala Asp Gly Asn Val Asp Tyr His Met Asn Ser
            100                 105                 110

Val Pro Ile Gln Gln Glu Ile Leu Val Leu Arg Arg Glu Pro Arg His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 163
<211> LENGTH: 330
<212> TYPE: DNA
<213> ORGANISM: Homo sapiens
<220> FEATURE:
<223> OTHER INFORMATION: Antibody 01

<400> SEQUENCE: 163

```
aattttatgc tgactcagcc ccactctgtg tcggagtctc cggggaagac ggtaaccatc    60
```

```
tcctgcaccc gcagcagtgg cagccttgcc aactactatg tgcagtggta ccaacagcgc      120
ccgggcagtg cccccaccat tgtgatcttt gcgaataacc aaagaccctc tggggtccct      180
gatcgattct ctggctccat cgacagctcc tccaactctg cctccctcac catctctaga      240
ctgaagactg aggacgaggc tgactactac tgccagtctt atgatgacag cagcgtggtg      300
ttcggcggag ggaccaagct gaccgtccta                                       330
```

<210> SEQ ID NO 164
<211> LENGTH: 110
<212> TYPE: PRT
<213> ORGANISM: Homo sapiens
<220> FEATURE:
<223> OTHER INFORMATION: Antibody 01

<400> SEQUENCE: 164

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Asp Asp
                85                  90                  95

Ser Ser Val Val Phe Gly Gly Gly Thr Lys Leu Thr Val Leu
            100                 105                 110

<210> SEQ ID NO 165
<211> LENGTH: 330
<212> TYPE: DNA
<213> ORGANISM: Homo sapiens
<220> FEATURE:
<223> OTHER INFORMATION: Antibody 02

<400> SEQUENCE: 165

```
aattttatgc tgactcagcc ccactctgtg tcggagtctc cggggaagac ggtaaccatc      60
tcctgcaccc gcagcagtgg cagccttgcc aactactatg tgcagtggta ccaacagcgc      120
ccgggcagtt cccccaccat tgtgatcttt gcgaataacc aaagaccctc tggggtccct      180
gatcgattct ctggctccat cgacagctcc tccaactctg cctccctcac catctctgga      240
ctgaagactg aggacgaggc tgactactac tgccagtcgt acgaccccca cagcgtggtg      300
ttcggcggag ggaccaagct gaccgtccta                                       330
```

<210> SEQ ID NO 166
<211> LENGTH: 110
<212> TYPE: PRT
<213> ORGANISM: Homo sapiens
<220> FEATURE:
<223> OTHER INFORMATION: Antibody 02

<400> SEQUENCE: 166

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

```
Tyr Val Gln Trp Tyr Gln Gln Arg Pro Gly Ser Ser Pro Thr Ile Val
            35                  40                  45

Ile Phe Ala Asn Asn Gln Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Pro
                85                  90                  95

His Ser Val Val Phe Gly Gly Gly Thr Lys Leu Thr Val Leu
            100                 105                 110

<210> SEQ ID NO 167
<211> LENGTH: 330
<212> TYPE: DNA
<213> ORGANISM: Homo sapiens
<220> FEATURE:
<223> OTHER INFORMATION: Antibody 03

<400> SEQUENCE: 167
aattttatgc tgactcagcc ccactctgtg tcggagtctc cggggaagac ggtaaccatc      60
tcctgcaccc gcagcagtgg cagccttgcc aactactatg tgcagtggta ccaacagcgc     120
ccgggcagtg cccccaccat tgtgatcttt gcgaataacc aaagaccctc tggggtccct     180
gatcgattct ctggctccat cgacagctcc tccaactctg cctccctcac catctctaga     240
ctgaagactg aggacgaggc tgactactac tgccagtcct actccccca cagcgtggtg     300 ttcggcggag ggaccaagct gaccgtccta                                      330

<210> SEQ ID NO 168
<211> LENGTH: 110
<212> TYPE: PRT
<213> ORGANISM: Homo sapiens
<220> FEATURE:
<223> OTHER INFORMATION: Antibody 03

<400> SEQUENCE: 168

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
            35                  40                  45

Ile Phe Ala Asn Asn Gln Arg Pro Ser Gly Val Pro Asp Arg Phe Ser
 50                  55                  60

Gly Ser Ile Asp Ser Ser Asn Ser Ala Ser Leu Thr Ile Ser Arg
 65                  70                  75                  80

Leu Lys Thr Glu Asp Glu Ala Asp Tyr Tyr Cys Gln Ser Tyr Ser Pro
                85                  90                  95

His Ser Val Val Phe Gly Gly Gly Thr Lys Leu Thr Val Leu
            100                 105                 110

<210> SEQ ID NO 169
<211> LENGTH: 330
<212> TYPE: DNA
<213> ORGANISM: Homo sapiens
<220> FEATURE:
<223> OTHER INFORMATION: Antibody 04

<400> SEQUENCE: 169
aattttatgc tgactcagcc ccactctgtg tcggagtctc cggggaagac ggtaaccatc      60
```

```
tcctgcaccc gcagcagtgg cagccttgcc aactactatg tgcagtggta ccaacagcgc      120
ccgggcagtg cccccaccat tgtgatcttt gcgaataacc aaagaccctc tggggtccct      180
gatcgattct ctggctccat cgacagctcc tccaactctg cctccctcac catctctaga      240
ctgaagactg aggacgaggc tgactactac tgccagtcct actccccgac gagcgtggtg      300
ttcggcggag ggaccaagct gaccgtccta                                       330
```

<210> SEQ ID NO 170
<211> LENGTH: 110
<212> TYPE: PRT
<213> ORGANISM: Homo sapiens
<220> FEATURE:
<223> OTHER INFORMATION: Antibody 04

<400> SEQUENCE: 170

```
Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Ser Pro
                85                  90                  95

Thr Ser Val Val Phe Gly Gly Gly Thr Lys Leu Thr Val Leu
            100                 105                 110
```

<210> SEQ ID NO 171
<211> LENGTH: 330
<212> TYPE: DNA
<213> ORGANISM: Homo sapiens
<220> FEATURE:
<223> OTHER INFORMATION: Antibody 05

<400> SEQUENCE: 171

```
aattttatgc tgactcagcc ccactctgtg tcggagtctc cggggaagac ggtaaccatc      60
tcctgcaccc gcagcagtgg cagccttgcc aactactatg tgcagtggta ccaacagcgc      120
ccgggcagtg cccccaccat tgtgatcttt gcgaataacc aaagaccctc tggggtccct      180
gatcgattct ctggctccat cgacagctcc tccaactctg cctccctcac catctctaga      240
ctgaagactg aggacgaggc tgactactac tgccagtctt ataaccacaa ggacatcgtg      300
ttcggcggag ggaccaagct gaccgtccta                                       330
```

<210> SEQ ID NO 172
<211> LENGTH: 110
<212> TYPE: PRT
<213> ORGANISM: Homo sapiens
<220> FEATURE:
<223> OTHER INFORMATION: Antibody 05

<400> SEQUENCE: 172

```
Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Leu Ala Asn Tyr
            20                  25                  30
```

Tyr Val Gln Trp Tyr Gln Gln Arg Pro Gly Ser Ala Pro Thr Ile Val
          35                  40                  45

Ile Phe Ala Asn Asn Gln Arg Pro Ser Gly Val Pro Asp Arg Phe Ser
      50                  55                  60

Gly Ser Ile Asp Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Asn His
                  85                  90                  95

Lys Asp Ile Val Phe Gly Gly Gly Thr Lys Leu Thr Val Leu
              100                 105                 110

<210> SEQ ID NO 173
<211> LENGTH: 330
<212> TYPE: DNA
<213> ORGANISM: Homo sapiens
<220> FEATURE:
<223> OTHER INFORMATION: Antibody 06

<400> SEQUENCE: 173
aattttatgc tgactcagcc ccactctgtg tcggagtctc cggggaagac ggtaaccatc     60
tcctgcaccc gcagcagtgg cagccttgcc aactactatg tgcagtggta ccaacagcgc    120
ccgggcagtg cccccaccat tgtgatcttt gcgaataacc aaagaccctc tggggtccct    180
gatcgattct ctggctccat cgacagctcc tccaactctg cctccctcac catctctaga    240
ctgaagactg aggacgaggc tgactactac tgccagtcgt acagcccgag cagcgtggtg    300
ttcggcggag ggaccaagct gaccgtccta                                     330

<210> SEQ ID NO 174
<211> LENGTH: 110
<212> TYPE: PRT
<213> ORGANISM: Homo sapiens
<220> FEATURE:
<223> OTHER INFORMATION: Antibody 06

<400> SEQUENCE: 174

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
              20                  25                  30

Tyr Val Gln Trp Tyr Gln Gln Arg Pro Gly Ser Ala Pro Thr Ile Val
          35                  40                  45

Ile Phe Ala Asn Asn Gln Arg Pro Ser Gly Val Pro Asp Arg Phe Ser
      50                  55                  60

Gly Ser Ile Asp Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Ser Pro
                  85                  90                  95

Ser Ser Val Val Phe Gly Gly Gly Thr Lys Leu Thr Val Leu
              100                 105                 110

<210> SEQ ID NO 175
<211> LENGTH: 330
<212> TYPE: DNA
<213> ORGANISM: Homo sapiens
<220> FEATURE:
<223> OTHER INFORMATION: Antibody 07

<400> SEQUENCE: 175

```
aattttatgc tgactcagcc ccactctgtg tcggagtctc cggggaagac ggtaaccatc      60
tcctgcaccc gcagcagtgg cagccttgcc aactactatg tgcagtggta ccaacagcgc     120
ccgggcagtt cccccaccat tgtgatcttt gcgaataacc aaagaccctc tggggtccct     180
gatcgattct ctggctccat cgacagctcc tccaactctg cctccctcac catctctgga     240
ctgaagactg aggacgaggc tgactactac tgccagacgt acgaccccta cagcgtggtg     300
ttcggcggag ggaccaagct gaccgtccta                                      330
```

```
<210> SEQ ID NO 176
<211> LENGTH: 110
<212> TYPE: PRT
<213> ORGANISM: Homo sapiens
<220> FEATURE:
<223> OTHER INFORMATION: Antibody 07

<400> SEQUENCE: 176
```

| Asn | Phe | Met | Leu | Thr | Gln | Pro | His | Ser | Val | Ser | Glu | Ser | Pro | Gly | Lys |
|---|---|---|---|---|---|---|---|---|---|---|---|---|---|---|---|
| 1 | | | | 5 | | | | | 10 | | | | | 15 | |

| Thr | Val | Thr | Ile | Ser | Cys | Thr | Arg | Ser | Ser | Gly | Ser | Leu | Ala | Asn | Tyr |
|---|---|---|---|---|---|---|---|---|---|---|---|---|---|---|---|
| | | | 20 | | | | | 25 | | | | | 30 | | |

| Tyr | Val | Gln | Trp | Tyr | Gln | Gln | Arg | Pro | Gly | Ser | Ser | Pro | Thr | Ile | Val |
|---|---|---|---|---|---|---|---|---|---|---|---|---|---|---|---|
| | | | 35 | | | | | 40 | | | | | 45 | | |

| Ile | Phe | Ala | Asn | Asn | Gln | Arg | Pro | Ser | Gly | Val | Pro | Asp | Arg | Phe | Ser |
|---|---|---|---|---|---|---|---|---|---|---|---|---|---|---|---|
| | 50 | | | | | 55 | | | | | 60 | | | | |

| Gly | Ser | Ile | Asp | Ser | Ser | Ser | Asn | Ser | Ala | Ser | Leu | Thr | Ile | Ser | Gly |
|---|---|---|---|---|---|---|---|---|---|---|---|---|---|---|---|
| 65 | | | | | 70 | | | | | 75 | | | | | 80 |

| Leu | Lys | Thr | Glu | Asp | Glu | Ala | Asp | Tyr | Tyr | Cys | Gln | Thr | Tyr | Asp | Pro |
|---|---|---|---|---|---|---|---|---|---|---|---|---|---|---|---|
| | | | | 85 | | | | | 90 | | | | | 95 | |

| Tyr | Ser | Val | Val | Phe | Gly | Gly | Gly | Thr | Lys | Leu | Thr | Val | Leu |
|---|---|---|---|---|---|---|---|---|---|---|---|---|---|
| | | | 100 | | | | | 105 | | | | | 110 |

```
<210> SEQ ID NO 177
<211> LENGTH: 330
<212> TYPE: DNA
<213> ORGANISM: Homo sapiens
<220> FEATURE:
<223> OTHER INFORMATION: Antibody 10

<400> SEQUENCE: 177
aattttatgc tgactcagcc ccactctgtg tcggagtctc cggggaagac ggtaaccatc      60
tcctgcaccc gcagcagtgg cagccttgcc aactactatg tgcagtggta ccaacagcgc     120
ccgggcagtg cccccaccat tgtgatcttt gcgaataacc aaagaccctc tggggtccct     180
gatcgattct ctggctccat cgacagctcc tccaactctg cctccctcac catctctaga     240
ctgaagactg aggacgaggc tgactactac tgccagtcgt acgaccccca cagcgtggtg     300
ttcggcggag ggaccaagct gaccgtccta                                      330
```

```
<210> SEQ ID NO 178
<211> LENGTH: 110
<212> TYPE: PRT
<213> ORGANISM: Homo sapiens
<220> FEATURE:
<223> OTHER INFORMATION: Antibody 10

<400> SEQUENCE: 178
```

| Asn | Phe | Met | Leu | Thr | Gln | Pro | His | Ser | Val | Ser | Glu | Ser | Pro | Gly | Lys |
|---|---|---|---|---|---|---|---|---|---|---|---|---|---|---|---|
| 1 | | | | 5 | | | | | 10 | | | | | 15 | |

| Thr | Val | Thr | Ile | Ser | Cys | Thr | Arg | Ser | Ser | Gly | Ser | Leu | Ala | Asn | Tyr |

```
            20                  25                  30
Tyr Val Gln Trp Tyr Gln Gln Arg Pro Gly Ser Ala Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Asp Pro
                85                  90                  95

His Ser Val Val Phe Gly Gly Gly Thr Lys Leu Thr Val Leu
            100                 105                 110

<210> SEQ ID NO 179
<211> LENGTH: 330
<212> TYPE: DNA
<213> ORGANISM: Homo sapiens
<220> FEATURE:
<223> OTHER INFORMATION: Antibody 11

<400> SEQUENCE: 179
aattttatgc tgactcagcc ccactctgtg tcggagtctc cggggaagac ggtaaccatc     60
tcctgcaccc gcagcagtgg cagccttgcc aactactatg tgcagtggta ccaacagcgc    120
ccgggcagtg cccccaccat tgtgatcttt gcgaataacc aaagaccctc tggggtccct    180
gatcgattct ctggctccat cgacagctcc tccaactctg cctccctcac catctctaga    240
ctgaagactg aggacgaggc tgactactac tgccagtcct actcccccca cagcgtggtg    300
ttcggcggag ggaccaagct gaccgtccta                                      330

<210> SEQ ID NO 180
<211> LENGTH: 110
<212> TYPE: PRT
<213> ORGANISM: Homo sapiens
<220> FEATURE:
<223> OTHER INFORMATION: Antibody 11

<400> SEQUENCE: 180

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Ser Pro
                85                  90                  95

His Ser Val Val Phe Gly Gly Gly Thr Lys Leu Thr Val Leu
            100                 105                 110

<210> SEQ ID NO 181
<211> LENGTH: 330
<212> TYPE: DNA
<213> ORGANISM: Homo sapiens
<220> FEATURE:
<223> OTHER INFORMATION: Antibody 12

<400> SEQUENCE: 181
```

```
aattttatgc tgactcagcc ccactctgtg tcggagtctc cggggaagac ggtaaccatc    60
tcctgcaccc gcagcagtgg cagccttgcc aactactatg tgcagtggta ccaacagcgc   120
ccgggcagtg cccccaccat tgtgatcttt gcgaataacc aaagaccctc tggggtccct   180
gatcgattct ctggctccat cgacagctcc tccaactctg cctccctcac catctctaga   240
ctgaagactg aggacgaggc tgactactac tgccagacgt acgaccccta cagcgtggtg   300
ttcggcggag ggaccaagct gaccgtccta                                    330
```

<210> SEQ ID NO 182
<211> LENGTH: 110
<212> TYPE: PRT
<213> ORGANISM: Homo sapiens
<220> FEATURE:
<223> OTHER INFORMATION: Antibody 12

<400> SEQUENCE: 182

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Arg
65                  70                  75                  80

Leu Lys Thr Glu Asp Glu Ala Asp Tyr Tyr Cys Gln Thr Tyr Asp Pro
                85                  90                  95

Tyr Ser Val Val Phe Gly Gly Gly Thr Lys Leu Thr Val Leu
            100                 105                 110
```

<210> SEQ ID NO 183
<211> LENGTH: 330
<212> TYPE: DNA
<213> ORGANISM: Homo sapiens
<220> FEATURE:
<223> OTHER INFORMATION: Antibody 13

<400> SEQUENCE: 183

```
aattttatgc tgactcagcc ccactctgtg tcggagtctc cggggaagac ggtaaccatc    60
tcctgcaccc gcagcagtgg cagccttgcc aactactatg tgcagtggta ccaacagcgc   120
ccgggcagtg cccccaccat tgtgatcttt gcgaataacc aaagaccctc tggggtccct   180
gatcgattct ctggctccat cgacagctcc tccaactctg cctccctcac catctctaga   240
ctgaagactg aggacgaggc tgactactac tgccagtctt atgacccgcg ggtggtcgtg   300
ttcggcggag ggaccaagct gaccgtccta                                    330
```

<210> SEQ ID NO 184
<211> LENGTH: 110
<212> TYPE: PRT
<213> ORGANISM: Homo sapiens
<220> FEATURE:
<223> OTHER INFORMATION: Antibody 13

<400> SEQUENCE: 184

```
Asn Phe Met Leu Thr Gln Pro His Ser Val Ser Glu Ser Pro Gly Lys
1               5                   10                  15
```

```
Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Asp Pro
                85                  90                  95

Arg Val Val Val Phe Gly Gly Gly Thr Lys Leu Thr Val Leu
            100                 105                 110

<210> SEQ ID NO 185
<211> LENGTH: 330
<212> TYPE: DNA
<213> ORGANISM: Homo sapiens
<220> FEATURE:
<223> OTHER INFORMATION: Antibody 14

<400> SEQUENCE: 185
aattttatgc tgactcagcc ccactctgtg tcggagtctc cggggaagac ggtaaccatc      60
tcctgcaccc gcagcagtgg cagccttgcc aactactatg tgcagtggta ccaacagcgc     120
ccgggcagtg cccccaccat tgtgatcttt gcgaataacc aaagaccctc tggggtccct     180
gatcgattct ctggctccat cgacagctcc tccaactctg cctccctcac catctctaga     240
ctgaagactg aggacgaggc tgactactac tgccagtctt atgacccgac gaaccaggtg     300
ttcggcggag ggaccaagct gaccgtccta                                      330

<210> SEQ ID NO 186
<211> LENGTH: 110
<212> TYPE: PRT
<213> ORGANISM: Homo sapiens
<220> FEATURE:
<223> OTHER INFORMATION: Antibody 14

<400> SEQUENCE: 186

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Asp Pro
                85                  90                  95

Thr Asn Gln Val Phe Gly Gly Gly Thr Lys Leu Thr Val Leu
            100                 105                 110

<210> SEQ ID NO 187
<211> LENGTH: 330
<212> TYPE: DNA
<213> ORGANISM: Homo sapiens
<220> FEATURE:
<223> OTHER INFORMATION: Antibody 15
```

```
<400> SEQUENCE: 187
aattttatgc tgactcagcc ccactctgtg tcggagtctc cggggaagac ggtaaccatc    60
tcctgcaccc gcagcagtgg cagccttgcc aactactatg tgcagtggta ccaacagcgc   120
ccgggcagtg cccccaccat tgtgatcttt gcgaataacc aaagaccctc tggggtccct   180
gatcgattct ctggctccat cgacagctcc tccaactctg cctccctcac catctctaga   240
ctgaagactg aggacgaggc tgactactac tgccagtcct actccccgac gagcgtggtg   300
ttcggcggag ggaccaagct gaccgtccta                                    330

<210> SEQ ID NO 188
<211> LENGTH: 110
<212> TYPE: PRT
<213> ORGANISM: Homo sapiens
<220> FEATURE:
<223> OTHER INFORMATION: Antibody 15

<400> SEQUENCE: 188

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ala Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Arg
65                  70                  75                  80

Leu Lys Thr Glu Asp Glu Ala Asp Tyr Tyr Cys Gln Ser Tyr Ser Pro
                85                  90                  95

Thr Ser Val Val Phe Gly Gly Gly Thr Lys Leu Thr Val Leu
            100                 105                 110

<210> SEQ ID NO 189
<211> LENGTH: 30
<212> TYPE: PRT
<213> ORGANISM: Homo sapiens
<220> FEATURE:
<223> OTHER INFORMATION: VH framework region 1

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 190
<211> LENGTH: 14
<212> TYPE: PRT
<213> ORGANISM: Homo sapiens
<220> FEATURE:
<223> OTHER INFORMATION: VH framework region 2

<400> SEQUENCE: 190

Trp Val Arg Gln Ala Pro Gly Lys Gly Leu Glu Trp Val Ser
1               5                   10

<210> SEQ ID NO 191
<211> LENGTH: 32
<212> TYPE: PRT
<213> ORGANISM: Homo sapiens
```

<220> FEATURE:
<223> OTHER INFORMATION: VH framework region 3

<400> SEQUENCE: 191

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 192
<211> LENGTH: 11
<212> TYPE: PRT
<213> ORGANISM: Homo sapiens
<220> FEATURE:
<223> OTHER INFORMATION: VH framework region 4

<400> SEQUENCE: 192

Trp Gly Gln Gly Thr Leu Val Thr Val Ser Ser
1               5                   10

<210> SEQ ID NO 193
<211> LENGTH: 22
<212> TYPE: PRT
<213> ORGANISM: Homo sapiens
<220> FEATURE:
<223> OTHER INFORMATION: VL framework region 1

<400> SEQUENCE: 193

Asn Phe Met Leu Thr Gln Pro His Ser Val Ser Glu Ser Pro Gly Lys
1               5                   10                  15

Thr Val Thr Ile Ser Cys
            20

<210> SEQ ID NO 194
<211> LENGTH: 15
<212> TYPE: PRT
<213> ORGANISM: Homo sapiens
<220> FEATURE:
<223> OTHER INFORMATION: VL framework region 2

<400> SEQUENCE: 194

Trp Tyr Gln Gln Arg Pro Gly Ser Ser Pro Thr Ile Val Ile Phe
1               5                   10                  15

<210> SEQ ID NO 195
<211> LENGTH: 34
<212> TYPE: PRT
<213> ORGANISM: Homo sapiens
<220> FEATURE:
<223> OTHER INFORMATION: VL framework region 3

<400> SEQUENCE: 195

Gly Val Pro Asp Arg Phe Ser Gly Ser Ile Asp Ser Ser Ser Asn Ser
1               5                   10                  15

Ala Ser Leu Thr Ile Ser Gly Leu Lys Thr Glu Asp Glu Ala Asp Tyr
            20                  25                  30

Tyr Cys

<210> SEQ ID NO 196
<211> LENGTH: 10
<212> TYPE: PRT
<213> ORGANISM: Homo sapiens
<220> FEATURE:
<223> OTHER INFORMATION: VL framework region 4

-continued

```
<400> SEQUENCE: 196

Phe Gly Gly Gly Thr Lys Leu Thr Val Leu
1               5                   10

<210> SEQ ID NO 197
<211> LENGTH: 153
<212> TYPE: PRT
<213> ORGANISM: Artificial sequence
<220> FEATURE:
<223> OTHER INFORMATION: Synthetic sequence: N-terminal tagged human
      IL-17A

<400> SEQUENCE: 197

Met Gly Gly Leu Asn Asp Ile Phe Glu Ala Gln Lys Ile Glu Trp His
1               5                   10                  15

Glu Ile Val Lys Ala Gly Ile Thr Ile Pro Arg Asn Pro Gly Cys Pro
            20                  25                  30

Asn Ser Glu Asp Lys Asn Phe Pro Arg Thr Val Met Val Asn Leu Asn
        35                  40                  45

Ile His Asn Arg Asn Thr Asn Thr Asn Pro Lys Arg Ser Ser Asp Tyr
    50                  55                  60

Tyr Asn Arg Ser Thr Ser Pro Trp Asn Leu His Arg Asn Glu Asp Pro
65                  70                  75                  80

Glu Arg Tyr Pro Ser Val Ile Trp Glu Ala Lys Cys Arg His Leu Gly
                85                  90                  95

Cys Ile Asn Ala Asp Gly Asn Val Asp Tyr His Met Asn Ser Val Pro
            100                 105                 110

Ile Gln Gln Glu Ile Leu Val Leu Arg Arg Glu Pro Pro His Cys Pro
        115                 120                 125

Asn Ser Phe Arg Leu Glu Lys Ile Leu Val Ser Val Gly Cys Thr Cys
    130                 135                 140

Val Thr Pro Ile Val His His Val Ala
145                 150

<210> SEQ ID NO 198
<211> LENGTH: 132
<212> TYPE: PRT
<213> ORGANISM: Homo sapiens
<220> FEATURE:
<223> OTHER INFORMATION: Mature human IL-17A

<400> SEQUENCE: 198

Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
            20                  25                  30

Thr Asn Thr Asn Pro Lys Arg Ser Ser Asp Tyr Tyr Asn Arg Ser Thr
        35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Ile Asn Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
            100                 105                 110

Glu Lys Ile Leu Val Ser Val Gly Cys Thr Cys Val Thr Pro Ile Val
        115                 120                 125
```

His His Val Ala
    130

<210> SEQ ID NO 199
<211> LENGTH: 17
<212> TYPE: PRT
<213> ORGANISM: Homo sapiens
<220> FEATURE:
<223> OTHER INFORMATION: Human IL-17A peptide

<400> SEQUENCE: 199

Cys Arg His Leu Gly Cys Ile Asn Ala Asp Gly Asn Val Asp Tyr His
1               5                   10                  15

Met

<210> SEQ ID NO 200
<211> LENGTH: 160
<212> TYPE: PRT
<213> ORGANISM: Artificial sequence
<220> FEATURE:
<223> OTHER INFORMATION: Synthetic sequence: Mutant IL-17A precursor
      with His tag

<400> SEQUENCE: 200

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Gln Arg Cys Val Asn Ala Glu Gly Lys Leu Asp His His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala His His His His His
145                 150                 155                 160

<210> SEQ ID NO 201
<211> LENGTH: 132
<212> TYPE: PRT
<213> ORGANISM: Artificial sequence
<220> FEATURE:
<223> OTHER INFORMATION: Synthetic sequence: Mutant mature IL-17A

<400> SEQUENCE: 201

Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
                20                  25                  30

Thr Asn Thr Asn Pro Lys Arg Ser Ser Asp Tyr Tyr Asn Arg Ser Thr
            35                  40                  45

-continued

```
Ser Pro Trp Asn Leu His Arg Asn Glu Asp Pro Glu Arg Tyr Pro Ser
    50                  55                  60

Val Ile Trp Glu Ala Lys Cys Arg His Gln Arg Cys Val Asn Ala Glu
65                  70                  75                  80

Gly Lys Leu Asp His His Met Asn Ser Val Pro Ile Gln Gln Glu Ile
                85                  90                  95

Leu Val Leu Arg Arg Glu Pro Pro His Cys Pro Asn Ser Phe Arg Leu
            100                 105                 110

Glu Lys Ile Leu Val Ser Val Gly Cys Thr Cys Val Thr Pro Ile Val
        115                 120                 125

His His Val Ala
    130
```

ANTIBODIES TO IL-17A AND USES THEREOF

This application is entitled to priority pursuant to 35 §U.S.C. 119(e) to U.S. Provisional Application Ser. No. 60/815,828, filed Jun. 23, 2006, and U.S. Provisional Application Ser. No. 60/913,566, filed Apr. 24, 2007, both of which are incorporated herein by reference in their entirety.

This invention relates to binding members for interleukin 17 (IL-17, also referred to as IL-17A), especially antibody molecules, and their therapeutic use e.g. in treating disorders associated with IL-17 such as rheumatoid arthritis.

IL-17A is a T-cell derived cytokine, which has pleiotropic pro-inflammatory activities. In vitro, IL-17A regulates production of inflammatory mediators from fibroblasts and synoviocytes, can synergise with other pro-inflammatory cytokines, and can promote cartilage degradation and osteoclastic bone resorption.

IL-17A is a homodimer consisting of two 155 amino acid chains. Each polypeptide chain includes a 23 amino acid N-terminal peptide which is cleaved to produce a mature polypeptide of 132 residues. IL-17A binds to and exerts its effects via activation of the IL-17 receptors A and C (Toy et al 2006). Five homologues of IL-17A exist, designated IL-17B to IL-17F, all with divergent and distinct biological roles. Swissprot accession numbers for the IL-17 homologues are: IL-17B Q9UHF5; IL-17C Q96POM4; IL-17D Q8TAD2; IL-17E Q9H293; IL-17F Q96PD4. IL-17B and IL-17C have a wide tissue expression with the cellular origin of the proteins unknown, although IL-17B transcripts can be found at high levels in the nervous system (Moore et al 2002). IL-17B and IL-17C can induce TNFα from the monocytic cell line THP-1 (Li et al 2000), and induce neutrophilia when injected into mouse models (Shi et al 2000). IL-17D is detected in multiple tissues and is expressed in resting CD4+ T cells and CD19+ B cells (Starnes et al 2002). IL-17E (IL-25) elicits Th2 type responses such as airway hyper responsiveness and eosinophilia and has properties distinct to the other family members (Fort et al 2001). IL-17F exists as two isoforms and exhibits greatest homology with IL-17A (55 and 40% homology) and shares many similar functional properties such as induction of neutrophilia in the lung and induction of pro-inflammatory cytokines including IL-8 (Hymowitz et al 2001; Hurst et al 2002, Oda et al. 2005). IL-17 family members may have a role in innate and adaptive immunity hence an antibody targeting only IL-17A will ensure the specific effects of IL-17A signalling are suppressed in areas where IL-17A is expressed.

Binding between family members and the IL-17 receptor family is not fully understood. IL-17E is known to signal via IL-17RB although IL-17B has also been reported to bind with lower affinity (Lee et al. 2001). IL-17A has been reported to bind IL-17RC (IL-17RL) in addition to IL-17RA and similarly IL-17F shares binding to these receptors (Toy et al. 2006, Kuestner et al. 2005). Further receptors, IL-17RD and IL-17RE exist although their endogenous ligands are yet to be identified. Multiple splice variants exist for IL-17RC and IL-17RD (Haudenschild et al. 2002; Haudenschild et al. 2006; Moseley et al. 2003).

Binding of IL-17A to its receptor is likely to induce oligomerisation of the receptor resulting in its activation. Activation of IL-17RA by IL-17A activates a number of pro-inflammatory signal pathways such as the extracellular signal-regulated protein kinase (ERK1/2), c-jun N-terminal kinase (JNK) and p38 MAP kinase pathways. Activation of these pathways triggers changes in the expression levels of a range of pro-inflammatory genes and proteins, via mechanisms which are not completely defined.

IL-17A is secreted primarily by CD4+ and CD8+ T cells (Lubberts et al. 2001). IL-17A, either as its RNA or intracellular protein, has also been detected in neutrophils, eosinophils and human blood monocytes (Molet et al. 2001; Ferretti et al. 2003). IL-6 and TGFβ have recently been implicated in differentiation of naïve T cells into IL-17 producing T cells (Betteli et al. 2006), while two further cytokines implicated in rheumatoid arthritis, IL-15 and IL-23, regulate the release of IL-17A from T lymphocytes.

IL-17A upregulates inflammatory cytokine production and prostaglandin production from synovial fibroblasts, enhances MMP production from synovial fibroblasts and articular chondrocytes and may play a role in osteoclastic bone resorption. In the context of the inflammatory milieu in rheumatoid arthritis (RA) tissue, IL-17A may have a particular role in synergising with other pro-inflammatory cytokines notably TNF-α and IL-1β.

Several lines of evidence suggest an important role for IL-17 in the pathogenesis of rheumatoid arthritis (RA). Functional IL-17A was spontaneously secreted by 16/18 RA synovial explants compared to 2/12 OA explants and 0/3 normal synovial explants. Immunostaining of RA synovium revealed IL-17A producing cells in the T cell rich area (Chabaud et al. 1999). The level of IL-17A in serum of RA patients is elevated compared with normal control serum (Cho et al. 2004).

IL-17A has been shown to stimulate the release of a range of pro-inflammatory cytokines. IL-17A, sometimes acting in synergy with other cytokines, enhances IL-1, IL-6, and LIF production from synovial fibroblasts (Katz et al. 2001; Chabaud et al. 1998). Additionally, IL-17A has been shown to upregulate COX-2 expression in inflammatory cells.

IL-17A induces COX-2 gene expression in human chondrocytes, synovial fibroblasts and macrophages and human synovial explants (e.g. Faour et al. 2003; Le Grand et al. 2001). Recombinant IL-17A upregulates synoviocyte COX-2 expression and enhances TNFα-stimulated synoviocyte COX-2 expression (Stamp et al. 2004).

In addition to these "classical" pro-inflammatory activities, IL-17A also elicits other effects in the RA joint such as promoting degradation of cartilage. IL-17 has also been shown to be involved in the upregulation of MMPs and impact on cartilage degradation. IL-17A increases spontaneous production of MMP1 by human RA synoviocytes. IL-17A co-ordinately upregulates MMP3, MMP13 and ADAMTS4 genes in bovine articular chondrocytes (Sylvester et al. 2004). IL-17A is a potent inducer of matrix breakdown and an inhibitor of matrix synthesis in articular cartilage explants (Cai et al. 2001). One mechanism by which IL-17A suppresses matrix synthesis by articular chondrocytes is through enhancement of NO production (Lubberts et al. 2000). Adenoviral IL-17A injected into the knee joint of type II collagen immunised mice accelerates onset, aggravates synovial inflammation and enhances joint destruction at this site (Lubberts et al. 2001). IL-17A may also be involved in osteoclastic bone resorption in R.A. (Kotake et al. 1999).

An important aspect of IL-17A biology is its ability to synergise with other cytokines. For example, IL-17A enhances TNF-α-induced synthesis of IL-1, IL-6 and IL-8 in synovial fibroblasts (Katz et al. 2001). Additionally, in the osteoblastic cell line, MC-3T3, IL-17 and TNF-α exhibit potent synergy in mediating IL-6 secretion (Ruddy et al. 2004). IL-17A enhances IL-1β-induced IL-6 and LIF production by RA synoviocytes (Chabaud et al. 1998).

The role of IL-17A in RA is further supported by in vivo evidence from animal models of disease. Overexpression of IL-17A induces cartilage damage in streptococcal cell wall (SCW)-induced arthritis in mice deficient in IL-1 (Koenders et al. 2005b). In a collagen-induced arthritis (CIA) model, overexpression of IL-17A enhances arthritis (Chabaud & Miossec 2001). Additionally, CIA is suppressed in IL-17A deficient mice or in mice treated with anti-IL-17 mAb (Nakae et al. 2003; Lubberts et al. 2001; Lubberts et al. 2004).

In addition to its role in RA, IL-17A activity has been linked with a number of other pathologies including:

osteoarthritis (e.g. Honorati et al. 2002); Malemud et al. 2004);
bone loss (Lubberts et al. 2003) and loosening of bone implants (Van Bezooijen et al. 1999);
airways hypersensitivity including allergic airway disease such as asthma (Molet et al. 2001; Wong et al. 2001; Linden 2006) and ARDS;
demyelinating disorders including multiple sclerosis (Lock et al. 2002; Touil et al. 2006);
psoriasis (Teunissen et al. 1998) and psoriatic arthritis;
dermal hypersensitivity including atopic dermatitis (Toda et al. 2003);
acute transplant rejection (Antonysamy et al. 1999; Yoshida et al. 2006; Tang et al. 2001);
allograft rejection (Hsieh et al. 2001);
graft-versus host disease;
systemic sclerosis (Kurasawa et al. 2000);
systemic lupus erythematosus (Wong et al. 2000);
autoimmune inflammatory bowel diseases including ulcerative colitis (Nielsen et al. 2003; Fujino et al. 2003; Yen et al. 2006) and Crohn's disease;
urological inflammatory disorders including benign prostatic hyperplasia (Kramer & Marberger 2006);
cardiovascular disease including atherosclerosis (Csiszar & Ungvari 2004), Kawasaki disease (Sohn et al. 2003), ischaemic heart disease (Csiszar 2003) and stroke;
vasculitis including Behcet's disease (Hamzaoui et al. 2002);
periodic fevers including familial Mediterranean fever (Haznedaroglu et al. 2005);
glucose metabolism including type 1 and type 2 diabetes (Fisman 2003);
pulmonary diseases including chronic obstructive pulmonary disease (Shen et al. 2004a; Shen et al. 2004b), bronchitis, emphysema, bronchiolitis obliterans syndrome (Vanaudenaerde et al. 2003) and lung fibrosis;
cancers including lymphoma (Maggio et al. 2002) and tumours (Numasaki et al. 2005);
peridontitis (Vernal et al. 2005; Takahashi 2005);
diseases caused by viral infection including herpetic stromal keratitis (Maertzdorf et al. 2002);
other IL-17 mediated inflammatory disorders including for example allergies, reactive arthritis, inflammatory pain, spondyloarthropathies including ankylosing spondylitis, inflammatory disease of the skin and cornea, inflammatory muscle disorders;
other IL-17 mediated acute inflammatory reactions such as infections including septicaemia, septic and endotoxic shock, meningitis and trauma (surgery);
other IL-17 mediated autoimmune disorders including for example autoimmune haematological disorders, Alzheimer's, sarcoidosis, cirrhosis, gall bladder and liver diseases including hepatitis, glomerulonephritis;
other IL-17 mediated metabolic disorders including for example dislipidemia.

Blockade of IL-17A in vivo suppresses inflammation, joint destruction and disease progression in a number of arthritis models. Use of IL-17R Fc fusion proteins have demonstrated suppression of joint damage at the macroscopic level in murine CIA (Lubberts et al. 2001) and also by histological analysis in rat adjuvant induced arthritis (AIA) models of arthritis (Bush et al. 2002). Use of commercial neutralising antibodies to IL-17 (rat anti-mouse) and IL-17R (rat anti-mouse) have demonstrated inhibition of swelling and arthritis onset in an infectious model of arthritis (Burchill et al. 2003). Rabbit anti-mouse polyclonal antibodies have been used in murine models of arthritis demonstrating decreased severity of joint damage and cartilage destruction and reduction in levels of pro-inflammatory mediators including RANKL, IL-$\beta$1 and IL-6 (Lubberts et al. 2004; Koenders et al. 2005a).

Neutralisation of IL-17 has demonstrated functional effects in other animal models of a range of diseases. IL-17R Fc fusion protein extended survival in a mouse allograft model (Antonysamy et al. 1999). IL-17R IgG fusion protein also attenuated colonic inflammation in a mouse model of trinitrobenzene sulphonic acid (TNBS) induced colitis (Zhang et al. 2006). Commercial monoclonal anti-IL-17 demonstrated efficacy in a mouse model of asthma by reducing bronchial neutrophilia upon Ova-challenge (Hellings et al. 2003). Rabbit polyclonal IL-17 neutralising antibodies also reduced adhesiogenesis in a rat model of surgical adhesion in a dose dependent manner (Chung et al. 2002).

Antibodies to IL-17A have been described. For example, a murine anti-IL-17 monoclonal antibody MAB317 has been produced by R&D Systems. This IgG2B antibody was developed from a mouse hybridoma elicited from a mouse immunised with purified recombinant human IL-17 (E. Coli-derived). Additionally a further murine anti-IL-17 antibody 53.159.16 (Biosource Inc.) has been developed which has neutralising properties. This IgG1K antibody was developed from a mouse hybridoma elicited from a mouse (Balb/c) immunised with purified recombinant human IL-17. This antibody recognises natural and recombinant human IL-17.

WO2006/054059 (UCB CellTech) describes a neutralising antibody molecule for IL-17A. A PEGylated antibody fragment is described, which was derived from a germlined version of an anti-IL-17 antibody originally isolated from a hybridoma. The document states that using BIAcore the antibody fragment was determined to have an affinity for IL-17 in the range 133-365 pM.

WO2006/013107 (Novartis Pharma GmbH) describes binding members for IL-17A, in particular a human anti-IL-17 IgG1 antibody designated AIN457, which was isolated from a hybridoma. WO2006/013107 reports BIAcore affinity measurements (Kd) for interaction between recombinant AIN457 and IL-17 from man (0.227 nM), marmoset (1.2 nM), rhesus monkey (9 nM) and cynomolgus monkey (6 nM), indicating an approximately 25-fold difference in affinity for human and cynomolgus IL-17 respectively.

Binding members for IL-17A, also referred to as IL-17A-binding members, are described herein. Binding members of the invention may be antibody molecules, especially human antibody molecules, for IL-17A.

The binding members are useful for treating disorders associated with IL-17A, e.g. one or more of the IL-17-related disorders referred to elsewhere herein, such as rheumatoid arthritis.

Described herein are binding members that bind within the region of positions 71-87 of mature human IL-17A. Positions 71-87 have sequence Cys-Arg-His-Leu-Gly-Cys-Ile-Asn-Ala-Asp-Gly-Asn-Val-Asp-Tyr-His-Met (SEQ ID NO: 199).

A binding member of the invention may bind at least one residue of Cys-Arg-His-Leu-Gly-Cys-Ile-Asn-Ala-Asp-Gly-Asn-Val-Asp-Tyr-His-Met (SEQ ID NO: 199). It may for example bind one, two, three, four, five or more than five residues of SEQ ID NO: 199.

A binding member of the invention may bind mature human IL-17A (SEQ ID NO: 198) at residue Leu74, Tyr85, His86 and/or Met 87. For example it may bind Leu74, Tyr85 and/or His86. The binding member may bind all of these residues. Binding may be determined for example by detecting or observing specific interactions between the binding member and the residues of IL-17A, e.g. in a structure of the binding member: IL-17A complex which may be determined for example using X-ray crystallography. A structure of Antibody 7 bound to human IL-17A determined using X-ray crystallography indicated that Antibody 7 binds residues 74 (Leu), 85 (Tyr), 86 (His) and 87 (Met) of the mature sequence (SEQ ID NO: 198).

Optionally a binding member may bind flanking residues or structurally neighbouring residues in the IL-17A molecule, in addition to binding one or more residues within SEQ ID NO: 199. For example a binding member may bind Asn88.

A binding member of the invention may bind mature human IL-17A (SEQ ID NO: 198) at one or more, e.g. five or more, e.g. ten or more, e.g. all, of the following residues:
  Ser40
  Ser41
  Asp42
  Tyr43
  Arg46
  Leu74
  Tyr85
  H is 86
  Met87
  Asn88
  Pro126
  Ile127.

A binding member of the invention may bind mature human IL-17A at residue Ser40, Ser41, Asp42, Tyr43 and/or Arg46.

A binding member of the invention may bind mature human IL-17A at residue Tyr85, His86, Met87 and/or Asn88.

A binding member may bind mature human IL-17A at Pro126 and/or Ile127.

As noted elsewhere herein, IL-17A forms a dimer of two polypeptide chains. A binding member or a VH domain of the invention may bind each of two mature IL-17A polypeptides in a dimer.

For example, the binding member may bind one IL-17A polypeptide of the dimer at Tyr85, His86, Met87 and/or Asn88, and/or may bind the same polypeptide at Pro126 and/or Ile127, and/or may bind the other IL-17A polypeptide of the dimer at Ser40, Ser41, Asp42, Tyr43 and/or Arg46.

Any suitable method may be used to determine the sequence of residues bound by a binding member, e.g. hydrogen-deuterium exchange, site-directed mutagenesis, mass spectrometry, NMR and X-ray crystallography.

Use of X-ray crystallography to determine the precise 3-dimensional structure of proteins at atomic resolution is well known to those in the art and has been used to visualise in detail the parts of proteins that interact with antibodies (Padavattan et al, 2007; Karpusas et al., 2001). Once crystals of the binding member complexed with the target antigen are obtained, they are irradiated with X-rays to give a diffraction pattern, which depends on the exact atomic distribution. The diffraction pattern can be analysed by crystallographers to determine the three dimensional positional coordinates of every atom in the structure. This allows a detailed inspection of the interaction sites between the binding member and the IL-17A.

Thus, residues of IL-17A bound by a binding member may be determined by observing interactions between the binding member and the residues of IL-17A in an X-ray crystal structure of the binding member bound to IL-17A. Binding may for example comprise hydrogen bonding and/or non-polar (hydrophobic) interactions. A cut-off distance of 3.2 Å may be used for determining hydrogen bonds, and a cut-off distance of 4.0 Å may be used for determining non-polar interactions. An example of an X-ray crystal structure determination and identification of bound residues is presented in Example 7.4 herein.

Peptide amide hydrogen exchange is a very well described methodology used to study proteins (Englander et al 1994). More recently this has been further developed to use deuterium labelled proteins that can exchange for protons and coupling this to mass spectrometry to measure the rates of exchange across a whole protein (Pantazatos et al 2004). This rate of hydrogen/deuterium exchange (H/D exchange) can be modified significantly by accessibility to solvent such that when a part of the protein is involved in binding to another molecule the rate of exchange will slow significantly. This approach has been used to map the regions of a protein involved in interacting with antibodies (Lu et al 2005), and was used to investigate regions of IL-17A involved in binding antibodies of the invention, as detailed in Example 7.1 herein. Mass spectrometry was used in conjunction with H/D exchange, to identify regions of IL-17A in contact with a binding member. It may be demonstrated for example that H/D exchange for residues within SEQ ID NO: 199 is significantly slowed when IL-17A is bound to a binding member of the invention.

Mutagenesis of single amino acids and regions of proteins in order to correlate structure with activity is well known to one skilled in the art and has been used to define regions of proteins that bind to antibodies (Lu et al 2005). Examples of the use of these techniques for binding members of the invention are shown in example 7.2.

Binding to and/or neutralisation of mutant human IL-17A having amino acid sequence SEQ ID NO: 201 may be used to assess whether a binding member binds within the region of positions 71-87 of mature human IL-17A. Absence of binding or neutralisation, or significantly reduced binding or neutralisation, with mutant IL-17A compared with wild-type indicates that a binding member binds at least one residue of SEQ ID NO: 199.

A binding member of the invention may optionally not bind and/or neutralise mutant human IL-17A having amino acid sequence SEQ ID NO: 201. For example, a binding member of the invention may not inhibit binding of mutant human IL-17A SEQ ID NO: 201 to its receptor. Neutralisation of IL-17A may be determined by a variety of assays, examples of which are described elsewhere herein.

A binding member of the invention may not inhibit IL-6 release induced by mutant human IL-17A (SEQ ID NO: 201) in HT1080 cells. A binding member of the invention may show no significant neutralisation potency in an IL-6 release assay in HT1080 cells using mutant IL-17A (SEQ ID NO: 201) at a concentration of 2 nM, e.g. when the binding member is at a concentration of up to 50 nM.

In an IL-6 release assay in HT1080 cells, a binding member of the invention may have an IC50 more than 10-fold higher, more than 20-fold higher, more than 50-fold higher or more than 100-fold higher in an assay with 1 nM mutant human IL-17A (SEQ ID NO: 201) than in an assay with 1 nM or 2 nM mature human IL-17A (SEQ ID NO: 198). Example data are shown in Example 7.3 (Table 20b), showing that Antibody 7 has a much lower potency (higher IC50) for mutant IL-17A compared with mature human IL-17A. It is noted that no IC50 value could be determined for Antibody 7 in the assay with mutant IL-17A, thus indicating that any IC50 value was higher than could be measured in this assay.

As described elsewhere herein, binding of a binding member to IL-17 may be determined using surface plasmon resonance e.g. BIAcore. A binding member of the invention may for example show no significant binding, e.g. less than about 10 RU in a surface plasmon resonance assay with mutant human IL-17A having amino acid sequence SEQ ID NO: 201.

Surface plasmon resonance data may be fitted to a bivalent analyte model (simultaneous ka kd) and an affinity constant Kd calculated from the ratio of rate constants kd1/ka1. A binding member of the invention may have an affinity for binding mature human IL-17A (SEQ ID NO: 198) that is more than 5-fold, e.g. more than 10-fold or more than 50-fold, greater than for binding mutant human IL-17A (SEQ ID NO: 201).

Techniques such as X-ray crystallography may also be used to identify residues of IL-17A bound by a binding member, and may be useful to confirm and/or refine results of other techniques, e.g. identifying residues that are contacted by the binding member. Use of X-ray crystallography of proteins to determine secondary, tertiary and quarternary structure is well known to those skilled in the art and has been used previously to map the parts of proteins that interact with antibodies (Padavattan et al, 2007; Karpusas et al 2001). An isolated polypeptide or peptide comprising, or an isolated peptide consisting of, amino acid sequence SEQ ID NO: 199, may be utilised in methods of generating, isolating and/or testing further binding members for IL-17A according to the present invention.

Accordingly, further aspects of the invention relate to isolated fragments of mature human IL-17A sequence SEQ ID NO: 198, the fragments comprising or consisting of amino acid sequence SEQ ID NO: 199. Fragments may for example be up to 20, 25, 30, 50 or 100 amino acids long. One or more fragments may be contained within a longer isolated peptide or polypeptide sequence which is not an IL-17A amino acid sequence, e.g. which is not precursor or mature IL-17A e.g. is not SEQ ID NO: 198. Peptides or polypeptides comprising an isolated fragment or fragments of the IL-17A amino acid sequence may comprise additional amino acid residues, wherein the additional residues are non-contiguous with an IL-17A amino acid sequence. For example, SEQ ID NO: 199 may be followed or preceded by one or more residues non-contiguous with SEQ ID NO: 198. Binding members, e.g. antibody molecules, for such polypeptides or peptides are aspects of the invention.

In vivo endogenous IL-17A is glycosylated and therefore glycosylated human IL-17A is the therapeutic target antigen for human therapy. Whilst recombinant human IL-17A, which may be bacterially-derived (e.g. expressed in *E. coli*) and not glycosylated, may be used in assays described herein, we have also demonstrated that binding members of the invention may bind glycosylated human IL-17A, such as IL-17A produced by human T cells or human embryonic kidney (HEK) EBNA cells. This represents a significant advantage of binding members of the invention, since glycosylated human IL-17A is the target antigen for in vivo human applications. Affinity and/or potency of binding members of the invention for glycosylated and non-glycosylated IL-17A may be about the same.

As described in more detail in the Examples, binding members according to the invention neutralise IL-17A with high potency. Neutralisation means inhibition of a biological activity of IL-17A. Binding members of the invention may neutralise one or more activities of IL-17A. The inhibited biological activity is typically IL-17A binding to one or more of its binding partners or receptors, e.g. to IL-17RA.

Neutralisation of IL-17 binding to its receptor may be measured as cellular release of a biological molecule e.g. MMP13, PGE2 or a cytokine such as IL-6 or IL-8, in a biological assay, since IL-17A binding to its receptor induces cellular release of these molecules, which can be determined using appropriate assays, e.g. in HT1080 cells (available under ECACC No. 85111505), chondrocytes or other suitable cell- or tissue-types.

Inhibition of biological activity may be partial or total. In specific embodiments, binding members are provided that inhibit IL-17 biological activity by at least 95%, at least 90%, at least 85%, at least 80%, at least 75%, at least 70%, at least 60%, or at least 50% of the activity in absence of the binding member. The degree to which a binding member neutralises IL-17A is referred to as its neutralising potency. Potency may be determined or measured using one or more assays known to the skilled person and/or as described or referred to herein. For example, potency may be assayed in:

HTRF® (Homogeneous Time-Resolved Fluorescence) receptor-ligand binding assay
HTRF® epitope competition assay
HT1080 IL-6 release assay
HT1080 cell assay using synergised IL-6 release in response to IL-17 and TNFα
Chondrocyte IL-6/IL-8/MMP13/PGE2-release assay
IL-6 release assay in cartilage explants
IL-6 release assay in synovial fibroblasts (e.g. from RA or OA patients), e.g. using synergised IL-6 response to IL-17 and TNFα

Assays methods are described in the Examples.

Neutralising potency of a binding member as calculated in an assay using IL-17 from a first species (e.g. human) may be compared with neutralising potency of the binding member in the same assay using IL-17 from a second species (e.g. cynomolgus), in order to assess the extent of cross-reactivity of the binding member for IL-17 of the two species.

Binding members of the invention bind human IL-17A and cynomolgus monkey IL-17A, and may have a less than 30-fold, e.g. less than 25-, 20-, 15-, 10-, 5- or 2-fold difference in potency for neutralising human and cynomolgus IL-17A, for example as determined in an HT1080 IL-6 release assay.

For example, the data herein indicate that Antibody nos 1-4 and 7-16 have a less than 20-fold difference in potency for neutralising human and cynomolgus IL-17A respectively, in an HT1080 IL-6 release assay described herein. Data are presented in Example 2. Thus, in some embodiments, neutralisation potency of binding members of the invention for human and cynomolgus IL-17A is within 20-fold. In some embodiments neutralisation potency for human and cynomolgus IL-17A is about the same or equipotent, i.e. within 10 fold.

Potency is normally expressed as an $IC_{50}$ value, in nM unless otherwise stated. In functional assays, $IC_{50}$ is the concentration of a binding member that reduces a biological response by 50% of its maximum. $IC_{50}$ may be calculated by plotting % of maximal biological response as a function of the log of the binding member concentration, and using a software program such as Prism (GraphPad) or Origin (Origin Labs) to fit a sigmoidal function to the data to generate $IC_{50}$ values.

A binding member of the invention may have a neutralising potency or $IC_{50}$ of up to 15 nM in a human IL-17A HTRF® assay as described herein. This assay can be used to determine $IC_{50}$ for binding members in scFv format. The $IC_{50}$ may for example be up to 10.0, 5.0, 4.0, 3.0, 2.0 or 1.0 nM. Examples of $IC_{50}$ data are presented in Example 2 (see Table 5). A final concentration of 0.75 nM human IL-17A is used in the HTRF® receptor-ligand binding assay and a detailed method is given in the examples.

A binding member of the invention may have a neutralising potency or $IC_{50}$ of up to 40 nM in a human IL-17 HT1080 IL-6 release assay. The $IC_{50}$ may be for example up to 35, 25, 20, 15, 10 or 5 nM. A binding member of the invention may have a neutralising potency or $IC_{50}$ of up to 3.0, 2.0 or 1.0 nM in a human IL-17 HT1080 IL-6 release assay. Examples of $IC_{50}$ data are presented in Example 2 (see Table 6A). This assay measures IL-6 release in response to 1 nM human IL-17A and a detailed method is given in the examples.

A binding member of the invention may have a $pA_2$ value of about or less than 10 in a human IL-17 HT1080 IL-6 release assay. Methods of $pA_2$ analysis are described in the Examples section. Example data are presented in Example 3 (see Table 8a).

A binding member of the invention may have a neutralising potency or $IC_{50}$ of not more than 1 nM in an HT1080 cell assay measuring the synergised release of IL-6 in response to 125 pM human IL-17A and 25 pM TNFα. A binding member of the invention may have a neutralising potency or $IC_{50}$ of not more than 1, 0.5, or 0.3 nM in this assay. Examples of $IC_{50}$ data are presented in Example 2 (see Table 6b).

A binding member of the invention may have an $IC_{50}$ of not more than 1 nM, e.g. not more than 0.9, 0.8, 0.7, 0.6, 0.5, 0.4, 0.3, 0.2 0.1 nM for inhibition of IL-6 release in HT1080 cells stimulated by glycosylated IL-17A from human T cells. Example data are presented in Example 2 (Table 6c). These data indicate that antibodies of the invention bind and neutralise native human IL-17A.

Advantageously, high neutralisation potency may be combined with good species cross-reactivity. Thus, for example, a binding member may have an IC50 of not more than 1 nM in an IL-6 release HT1080 assay with human IL-17A, wherein the IC50 in the human IL-17A HT1080 assay is not more than 10-fold different from the IC50 in the cynomolgus IL-17A HT1080 assay. Neutralisation potency for human IL-17A may be greater than with cynomolgus IL-17A.

A binding member of the invention may have a neutralising potency of $IC_{50}$ of up to 150 nM in a cynomolgus IL-17 HT1080 IL-6 release assay, e.g. in IgG1 format. The $IC_{50}$ may for example be up to 150, 100, 50, 40, 30, 25, 20, 15, 10 or 5 nM. Examples of $IC_{50}$ data are presented in Example 2 (see Table 6A). A final concentration of 1 nM cynomolgus IL-17A is used in the IL-6 release assay in HT1080 cells and a detailed method is given in the examples.

Potency for inhibition of release of IL-6, IL-8, MMP13, and/or $PGE_2$ may be determined in human primary chondrocytes using an assay as described herein. Examples of data for binding members of the invention in these assays are shown in Example 4. A binding member of the invention may have an $IC_{50}$ of up to 3.0 nM, e.g. up to 2.0, 1.0, 0.9, 0.8, 0.7, 0.6, 0.5, 0.4, 0.3 or 0.2 nM, in a chondrocyte IL-6 release assay using IL-17 at a concentration of 0.2 nM. A binding member of the invention may have an $IC_{50}$ of up to 20 nM, e.g. up to 10, 5.0, 4.0, 3.0 or 2.0 nM in a chondrocyte IL-6 release assay using IL-17 at a concentration of 2 nM.

A binding member of the invention may have an $IC_{50}$ of up to 3.0 nM, e.g. up to 2.5, 2.3, 1.0, 0.5, 0.4, 0.3, 0.2 or 0.1 nM in a chondrocyte IL-8 release assay using IL-17 at a concentration of 0.2 nM. A binding member of the invention may have an $IC_{50}$ of up to 8 nM, e.g. up to 5, 4, 3, 2, 1.8, 1.6, 1.5, 1.0 or 0.8 nM in a chondrocyte IL-8 release assay using IL-17 at a concentration of 2 nM.

A binding member of the invention may have an $IC_{50}$ of up to 5 nM, e.g. up to 4, 3, 2, 1, 0.5 nM in a chondrocyte MMP13 release assay using IL-17 at a concentration of 0.2 nM. A binding member of the invention may have an $IC_{50}$ of up to 40 nM, e.g. up to 30, 20, 10, 5 nM, in a chondrocyte MMP13 release assay using IL-17 at a concentration of 2 nM.

A binding member of the invention may have an $IC_{50}$ of up to 6 nM, e.g. up to 5, 4, 3, 2, 1, 0.5 nM in a chondrocyte $PGE_2$ release assay using IL-17 at a concentration of 2 nM.

Binding members of the invention may exhibit inhibitory activity, e.g. at least 80% or 90% inhibition, or 100% inhibition, in an IL-6 release assay using IL-17A at a concentration of 10 ng/ml in a synergised response with TNFα at 1 ng/ml in a post mortem cartilage explant assay. A binding member of the invention may have an $IC_{50}$ of not more than 5 nM, e.g. not more than 4, 3, 2, 1, 0.5 nM in a post-mortem cartilage explant IL-6 release assay using IL-17A at a concentration of 10 ng/ml in a synergised response with TNFα at 1 ng/ml. Example data are presented in Example 6.1 (Tables 15a and 15b).

Binding members of the invention may exhibit inhibitory activity, e.g. at least 50, 60 or 65% inhibition, in an IL-17/TNFα synergy assay in OA synovial fibroblasts, as described herein (e.g. in an IL-8 release assay using 10 ng/ml or 1 ng/ml IL-17 in a synergised response with TNFα, where the maximal response has an IL-17 and TNFα component). Example data are presented in Example 6.2 (Tables 16a and 16b).

A binding member of the invention may have an $IC_{50}$ of not more than 5 nM, e.g. not more than 4, 3 or 2 nM in an RA synovial fibroblast IL-8 release assay using IL-17 at a concentration of 2 nM. Example data are presented in Example 6.3 (Table 17).

A binding member of the invention may have an $IC_{50}$ of not more than 5 nM, e.g. not more than 4, 3 or 2 nM in a synergised IL-17A plus TNFα RA synovial fibroblast IL-8 release assay using IL-17 at a concentration of 1 nM and TNFα at 0.1 ng/ml. Example data are presented in Example 6.3 (Table 17).

In a pre-mix mouse airpouch assay described herein, a binding member of the invention may inhibit IL-17A (pre-mixed with binding member) induced IL-6 release by at least 25%, e.g. at least 30, 35, 40, 45, 50, 55 or 60'. Inhibition may be about 100%. A binding member may for example have an $ID_{50}$ of up to 10, e.g. up to 5, 4, 3, 2 1 or 0.5 µg in this assay. Also in the mouse pre-mix airpouch assay described herein, a binding member of the invention may inhibit IL-17A induced influx of leukocytes by at least 80', e.g. at least 85, 90, 95, 98 or 99%. Inhibition may be about 100%. A binding member may for example have an $ID_{50}$ of up to 5, 4, 3, 2 or 1 µg in this assay. Example data for a binding member of the invention with Antibody 2 and Antibody 7 sets of CDRs are presented in Example 5 (see Table 13a and Table 14a).

In a systemically dosed mouse airpouch assay described herein, a binding member of the invention may inhibit IL-17A (binding member dosed systemically followed by IL-17A administered to the airpouch) induced IL-6 release by at least 70%, e.g. at least 75, 80 or 85%. A binding member may for example have an $ID_{50}$ of up to 1 µg, e.g. up to 0.5, 0.4, 0.3, 0.2, 0.1 or 0.05 µg in this assay. Also in the mouse systemically dosed airpouch assay described herein, a binding member of the invention may inhibit IL-17A induced influx of leukocytes by at least 70%, e.g. at least 75, 80, 85, 90 or 95%. Inhibition may be about 100%. A binding member may for example have an $ID_{50}$ of up to 2, e.g. up to 1.5, 1, 0.9, 0.8, 0.7 or 0.6 µg in this assay. Example data for a binding member of the invention with the Antibody 7 set of CDRs are presented in Example 5 (see Table 13b and Table 14b).

The data obtained in the airpouch assay as described in Example 5 demonstrate ability of a binding member to inhibit IL-17A induced responses when administered locally or systemically. The data indicate that administration of a binding member of the invention is effective to treat disorders associated with IL-17A in localised sites of inflammation, and thus are useful for treatment of disorders such as rheumatoid arthritis through inhibition of IL-17A induced responses in the synovial joint. It is notable that systemic administration of a binding member of the invention was shown to be effective at inhibiting effects of IL-17A, and that local administration was not required for effective inhibition. This is of particular advantage for clinical use of binding members, e.g. in man, where systemic administration may be used, and where the site of administration is often separate from the site or sites where the disorder is manifested, e.g. site or sites of inflammation such as the synovial joint.

Additionally, binding kinetics and affinity (expressed as the equilibrium dissociation constant, Kd) of IL-17A binding members for IL-17A may be determined, e.g. using surface plasmon resonance such as BIAcore, or Kd may be estimated from $pA_2$ analysis.

A binding member of the invention may for example have a Kd for human IL-17A of less than 1000 pM, e.g. less than 600, 500, 400, 300 or 200 pM as calculated from $pA_2$ analysis in the human IL-17 HT1080 IL-6 release assay.

As described elsewhere herein, surface plasmon resonance involves passing an analyte in fluid phase over a ligand attached to a support, and determining binding between analyte and ligand. Surface plasmon resonance may for example be performed whereby IL-17A is passed in fluid phase over a binding member attached to a support. Surface plasmon resonance data may be fitted to a bivalent analyte data model or a monovalent analyte data model. As shown in the Examples herein, a bivalent analyte data model was found to be particularly appropriate for determining affinity of binding members to IL-17. An affinity constant Kd may be calculated from the ratio of rate constants kd1/ka1 as determined by surface plasmon resonance using a bivalent analyte data model.

Examples of estimated KD values for binding IL-17 calculated using surface plasmon resonance are presented in Example 3 (see Table 8b). These data demonstrate good binding properties of Antibody 7 for human IL-17A recombinantly produced by expression in *E. coli* or in HEK EBNA cells. Binding to IL-17A from HEK EBNA cells demonstrates that the antibody binds native glycosylated human IL-17A. Binding by Antibody 7 of the native glycosylated form indicates that all of Antibodies 1 to 16 are able to bind native glycosylated human IL-17A, given that all these antibodies were derived from a single parent antibody (Antibody 1) and are thus believed to all bind the same or highly similar epitope of IL-17A.

A binding member of the invention may have less than 5-fold, e.g. less than 2.5-fold or less than 2-fold, difference in affinity for binding human IL-17A expressed in human cells (e.g. HEK EBNA-derived IL-17A) than for binding human IL-17A expressed in bacterial cells (e.g. *E. coli* derived IL-17A).

A binding member of the invention may have a Kd for human IL-17A of about or less than 2.5 nM, calculated from the ratio of rate constants kd1/ka1 as determined by surface plasmon resonance using a bivalent analyte data model. For example, a binding member of the invention may have a Kd for human IL-17A of less than 2.5 nM, 2 nM, 1.5 nM, 1.0 nM or 0.5 nM calculated from the ratio of rate constants kd1/ka1 as determined using surface plasmon resonance, using a bivalent analyte data model.

A binding member of the invention may have an affinity for human IL-17A of about or less than 0.3 nM, as determined by surface plasmon resonance using a monovalent analyte data model. A binding member of the invention may for example have a Kd for human IL-17A of less than 300 pM, e.g. less than 200 pM, as calculated using surface plasmon resonance using a monovalent data model.

A binding member of the invention may have a Kd for cynomolgus IL-17A of about or less than 1.5 nM calculated from the ratio of rate constants kd1/ka1 as determined by surface plasmon resonance using a bivalent analyte data model.

Binding members of the invention may have a less than 10-fold difference in affinity for human and cynomolgus IL-17A, e.g. as determined using surface plasmon resonance, using a monovalent or bivalent model to fit the data. Thus, a binding member of the invention may bind cynomolgus IL-17A with a Kd less than 10-fold different than for binding human IL-17A, e.g. less than 5-fold or less than 3-fold different, as determined using surface plasmon resonance. As noted elsewhere herein, affinity may be Kd calculated from the ratio of rate constants kd1/ka1 as determined by surface plasmon resonance using a bivalent analyte data model.

As illustrated in Example 3 and Table 8b, a good cross-reactivity in binding human and cynomolgus IL-17A was determined for Antibody 7.

Cross-reactivity data obtained for Antibody 7 can be taken to be representative of cross-reactivity for all of Antibodies 1 to 16, given that all these antibodies were derived from a single parent antibody (Antibody 1) and are thus believed to all bind the same or highly similar epitope of IL-17.

The data reported herein indicate that binding members of the invention are not cross-reactive with IL-17 homologues IL-17B, IL-17C, IL-17D, IL-17E or IL-17F. Weak binding is observed with IL-17F in some cases. Cross-reactivity may be determined for example by measuring degree of inhibition by an IL-17 homologue of IL-17A binding to a binding member of the invention, e.g. using an HTRF® epitope competition assay as described herein. As described herein, IL-17 homologues B to E do not significantly inhibit binding of IL-17A to binding members of the invention in such an assay, demonstrating that the binding members are not cross-reactive with IL-17 homologues B to E.

A binding member of the invention may show partial (i.e. less than 100%) inhibition of binding to IL-17A in an epitope competition assay with IL-17F, e.g. wherein IL-17F is at a concentration of 1 µM or more. For example, IL-17F may inhibit binding to IL-17A by not more than 50%, e.g. not more than about 20%

None of IL-17B, C, D, E nor F may be able to fully inhibit binding of a binding member to human IL-17A. Binding of a binding member of the invention to human IL-17A may not be fully inhibited by 1 µM of any of IL-17B, IL-17C, IL-17D, IL-17E or IL-17F (individually) in an epitope competition assay. Thus, binding of the binding member to human IL-17A may not be inhibited by more than 50%, e.g. not more than 20%, by 1 µM of any of IL-17B, IL-17C, IL-17D, IL-17E or IL-17F in an epitope competition assay using labelled IL-17A at a concentration equal to the dissociation constant Kd of the interaction of the binding member with human IL-17A, wherein said Kd is calculated from the ratio of rate constants kd1/ka1 as determined by surface plasmon resonance, e.g. BIAcore, using a bivalent analyte data model. The binding of the binding member to human IL-17A in such an epitope competition assay may for example not be inhibited by 1 µM of any of IL-17B, IL-17C, IL-17D or IL-17E, and may not be inhibited, or may be inhibited but by less than 50%, by 1 µM IL-17F.

Example data in the epitope competition assay are presented in Example 2.7 (see Table 7). IC50 values could not be determined in an epitope competition assay with IL-17B, C, D, E or F, indicating that the IC50 values were too high to be measurable in this assay.

The limited cross-reactivity with IL-17 homologues exhibited by binding members of the invention offers an advantage for their therapeutic and/or diagnostic use, particularly in in vivo applications where it is desirable to specifically inhibit IL-17A. Side-effects caused by undesirable cross-reactivity are reduced. Further, lower concentrations of binding member may be used, since the limited cross-reactivity means that more of an administered dose of binding member is available for binding target IL-17A. This represents a particular advantage in dosing for in vivo therapeutic applications.

A binding member of the invention may comprise an antibody molecule, e.g. a human antibody molecule. The binding member normally comprises an antibody VH and/or VL domain. VH domains of binding members are also provided as part of the invention. Within each of the VH and VL domains are complementarity determining regions, ("CDRs"), and framework regions, ("FRs"). A VH domain comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. A VH or VL domain framework comprises four framework regions, FR1, FR2, FR3 and FR4, interspersed with CDRs in the following structure:

FR1-CDR1-FR2-CDR2-FR3-CDR3-FR4.

Examples of antibody VH and VL domains, FRs and CDRs according to the present invention are as listed in the appended sequence listing that forms part of the present disclosure. Further exemplary CDRs are disclosed below and in Table 21. All VH and VL sequences, CDR sequences, sets of CDRs and sets of HCDRs and sets of LCDRs disclosed herein represent aspects and embodiments of the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs. Typically binding members of the invention are monoclonal antibodies.

A further aspect of the invention is an antibody molecule comprising a VH domain that has at least 80, 85, 90, 95, 98 or 99% amino acid sequence identity with a VH domain of any of antibodies 1 to 16 shown in the appended sequence listing, and/or comprising a VL domain that has at least 80, 85, 90, 95, 98 or 99% amino acid sequence identity with a VL domain of any of antibodies 1 to 16 shown in the appended sequence listing. Algorithms that can be used to calculate % identity of two amino acid sequences include e.g. BLAST (Altschul et al. 1990), FASTA (Pearson & Lipman 1988), or the Smith-Waterman algorithm (Smith & Waterman 1981), e.g. employing default parameters.

A binding member of the invention may comprise an antigen-binding site within a non-antibody molecule, normally provided by one or more CDRs e.g. an HCDR3 and/or LCDR3, or a set of CDRs, in a non-antibody protein scaffold, as discussed further below.

As described in more detail in the Experimental Part, we isolated a parent antibody molecule (antibody no 1) with a set of CDR sequences as shown in Table 21. Through a process of optimisation we generated a panel of antibody clones numbered 2 to 16, with CDR3 sequences derived from the parent CDR3 sequences and having substitutions at the positions indicated in Table 21. Thus for example it can be seen from Table 21 that Antibody 2 has the parent HCDR1, HCDR2, HCDR3, LCDR1 and LCDR2 sequences, and has a parent LCDR3 sequence in which Kabat residues 93 and 94 are replaced with P and H, respectively. The parent antibody molecule, and antibody molecules 2 to 16, as described herein refer respectively to antibody molecules with CDRs of the parent antibody molecule and to antibody molecules with CDRs of antibody molecules 2 to 16.

Described herein is a binding member comprising the parent set of CDRs as shown in Table 21, in which HCDR1 is SEQ ID NO: 3 (Kabat residues 31-35), HCDR2 is SEQ ID NO: 4 (Kabat residues 50-65), HCDR3 is SEQ ID NO: 5 (Kabat residues 95-102), LCDR1 is SEQ ID NO: 8 (Kabat residues 24-34), LCDR2 is SEQ ID NO: 9 (Kabat residues 50-56) and LCDR3 is SEQ ID NO: 10 (Kabat residues 89-97).

A binding member of the invention may comprise one or more CDRs as described herein, e.g. a CDR3, and optionally also a CDR1 and CDR2 to form a set of CDRs. The CDR or set of CDRs may be a parent CDR or parent set of CDRs, or may be a CDR or set of CDRs of any of antibodies 2 to 16, or may be a variant thereof as described herein.

For example, a binding member or a VL domain according to the invention may comprise the parent LCDR3 with Kabat residues 93 and 94 replaced by P and H, respectively.

A binding member or a VH domain may comprise the parent HCDR3 with one or more of the following substitutions:

Kabat residue 98 replaced by F or H;
Kabat residue 100A replaced by G or T;
Kabat residue 101 replaced by R;
Kabat residue 102 replaced by G or N.

A binding member, or a VL domain thereof may comprise the parent LCDR3 with one or more of the following substitutions:

Kabat residue 90 replaced by T;
Kabat residue 92 replaced by N or S;
Kabat residue 93 replaced by H or P;
Kabat residue 94 replaced by H, K, R, T or Y;
Kabat residue 95 replaced by D, N or V;
Kabat residue 96 replaced by I or Q.

Substitution of D at Kabat position 93 in LCDR3 with P is associated with greater potency of a binding member against human and/or cynomolgus IL-17A.

Binding members of the invention may comprise an HCDR1, HCDR2 and/or HCDR3 of any of antibodies 1 to 16 and/or an LCDR1, LCDR2 and/or LCDR3 of any of antibodies 1 to 16, e.g. a set of CDRs of any of antibodies 1 to 16 shown in Table 21. A binding member may comprise a set of VH CDRs of one of these antibodies. Optionally it may also comprise a set of VL CDRs of one of these antibodies, and the VL CDRs may be from the same or a different antibody as the VH CDRs. A VH domain comprising a set of HCDRs of any of antibodies 1 to 16, and/or a VL domain comprising a set of LCDRs of any of antibodies 1 to 16, are also individual embodiments of the invention.

Typically, a VH domain is paired with a VL domain to provide an antibody antigen-binding site, although as discussed further below a VH or VL domain alone may be used to bind antigen. In one embodiment, the antibody 1 VH domain is paired with the antibody 1 VL domain, so that an antibody antigen-binding site is formed comprising both the antibody 1 VH and VL domains. Analogous embodiments are provided for the other VH and VL domains disclosed herein. In other embodiments, the antibody 1 VH is paired with a VL domain other than the antibody 1 VL. Light-chain promiscuity is well established in the art. Again, analogous embodiments are provided by the invention for the other VH and VL domains disclosed herein. Thus, the VH of the parent or of any of antibodies 2 to 16 may be paired with the VL of the parent or of any of antibodies 2 to 16.

One aspect of the invention is an isolated antibody molecule comprising a VH domain with the VH domain amino acid sequence shown in SEQ ID NO: 62 and a VL domain with the VL domain amino acid sequence shown in SEQ ID NO: 67 or SEQ ID NO: 176.

A binding member may comprise a set of H and/or L CDRs of the parent antibody or any of antibodies 2 to 16 with ten or nine or fewer, e.g. one, two, three, four or five, substitutions within the disclosed set of H and/or L CDRs. For example, a binding member of the invention may comprise the Antibody 7 set of H and/or L CDRs with 10 or fewer substitutions, e.g. five or fewer substitutions, e.g. zero, one or two substitutions. Substitutions may potentially be made at any residue within the set of CDRs, and may be within CDR1, CDR2 and/or CDR3.

Substitutions may be within CDR3, e.g. at the positions substituted in any of Antibodies 2 to 16, as shown in Table 21. Thus, the one or more substitutions may comprise one or more substitutions at the following residues:

Kabat residue 98, 100A, 101 or 102 in HCDR3; or
Kabat residue 90, 92, 93, 94, 95 or 96 in LCDR3.

Thus, a CDR3 may for example be a parent (Antibody 1) LCDR3 having a substitution at Kabat residue 93 and/or 94.

Examples of substitutions in parent CDRs are described elsewhere herein. As described, the substitutions may comprise one or more substitutions as shown in Table 21.

A binding member of the invention may comprise an HCDR1, HCDR2 and/or HCDR3 as follows:

HCDR1 wherein Kabat residue 31 is Ser, Ala, Gly, Thr or Cys e.g. Ser and/or Kabat residue 32 is Tyr;
HCDR2 wherein Kabat residue 58 is Tyr or Phe, e.g. Tyr;
HCDR3 wherein
Kabat residue 96 is a hydrophobic residue, i.e. an amino acid residue with a non-polar side chain, for example Leu, Ile, Val, Ala or Phe, e.g. Leu,
Kabat residue 97 is a hydrophobic residue, e.g. Ile, Leu, Val, Ala or Phe, e.g. Ile, and/or
Kabat residue 98 is cyclic residue, i.e. an amino acid residue with a side chain comprising a cyclic moiety. For example, Kabat residue 98 may be H is, Trp or Phe, e.g. H is or Trp, e.g. His.

As indicated in Example 7.4, residues at these HCDR positions may bind IL-17A.

A binding member of the invention may comprise an LCDR1 and/or LCDR3 as follows:

LCDR1 wherein Kabat residue 31 is Tyr or Phe, e.g. Tyr, and/or Kabat residue 32 is Tyr or Phe, e.g. Tyr;
LCDR3 wherein Kabat residue 91 is Tyr and/or Kabat residue 93 is Pro, hydroxyproline, H is, methylhistidine or Asp, e.g. Pro or H is, e.g. Pro.

Optionally, Kabat residue 29 in LCDR1 is Ala and/or Kabat residue 30 in LCDR1 is Asn.

Optionally, a binding member of the invention may comprise an LCDR2 wherein Kabat residue 53 is an amino acid residue with an uncharged polar side chain, e.g. Gln.

As indicated in Example 7.4, residues at these LCDR positions may bind IL-17A.

For example, a binding member of the invention may comprise a set of CDRs: HCDR1, HCDR2, HCDR3, LCDR1, LCDR2 and LCDR3, comprising 7 or more, e.g. 8, 9 or all of the following residues:

Ser, Ala, Gly, Thr or Cys, e.g. Ser, at Kabat residue 31 of HCDR1;
Tyr at Kabat residue 32 of HCDR1;
Tyr or Phe, e.g. Tyr, at Kabat residue 58 of HCDR2;
a hydrophobic residue, e.g. Leu, Ile, Val, Ala or Phe, e.g. Leu, at Kabat residue 96;
a hydrophobic residue, e.g. Ile, Leu, Val, Ala or Phe, e.g. Ile, at Kabat residue 97 of HCDR3;
a cyclic residue e.g. H is, Trp or Phe, e.g. H is or Trp, e.g. H is, at Kabat residue 98 of HCDR3;
Tyr or Phe, e.g. Tyr, at Kabat residue 31 of LCDR1;
Tyr or Phe, e.g. Tyr, at Kabat residue 32 of LCDR1;
Tyr at Kabat residue 91 of LCDR3; and
Pro, hydroxyproline, H is or 3-methylhistidine, e.g. Pro or H is, e.g. Pro, at Kabat residue 93 of LCDR3.

The binding member may comprise a set of CDRs wherein:
Kabat residue 31 of HCDR1 is Ser;
Kabat residue 32 of HCDR1 is Tyr;
Kabat residue 58 of HCDR2 is Tyr;
Kabat residue 96 of HCDR3 is Leu;
Kabat residue 97 of HCDR3 is Ile;
Kabat residue 98 of HCDR3 is H is;
Kabat residue 31 of LCDR1 is Tyr;
Kabat residue 32 of LCDR1 is Tyr;
Kabat residue 91 of LCDR3 is Tyr; and
Kabat residue 93 of LCDR3 is Pro.

In a binding member of the invention:
HCDR1 may be 5 amino acids long, consisting of Kabat residues 31-35;
HCDR2 may be 17 amino acids long, consisting of Kabat residues 50-65;
HCDR3 may be 9 amino acids long, consisting of Kabat residues 95-102;
LCDR1 may be 13 amino acids long, consisting of Kabat residues 24-34;
LCDR2 may be 7 amino acids long, consisting of Kabat residues 50-56; and/or
LCDR3 may be 9 amino acids long, consisting of Kabat residues 89-97.

Kabat numbering of a set of HCDRs and LCDRs, wherein HCDR1 is Kabat residues 31-35, HCDR2 is Kabat residues 50-65, HCDR3 is Kabat residues 95-102, LCDR1 is Kabat residues 24-34, LCDR2 is Kabat residues 50-56 and LCDR3 is Kabat residues 89-97, is exemplified in Table 21.

A binding member may comprise an antibody molecule having one or more CDRs, e.g. a set of CDRs, within an antibody framework. For example, one or more CDRs or a set of CDRs of an antibody may be grafted into a framework (e.g. human framework) to provide an antibody molecule. Framework regions may comprise human germline gene segment sequences. Thus, the framework may be germlined, whereby one or more residues within the framework are changed to match the residues at the equivalent position in the most similar human germline framework. The skilled person can select a germline segment that is closest in sequence to the framework sequence of the antibody before germlining and test the affinity or activity of the antibodies to confirm that germlining does not significantly reduce antigen binding or potency in assays described herein. Human germline gene segment sequences are known to those skilled in the art and can be accessed for example from the VBase compilation.

In one embodiment, a binding member of the invention is an isolated human antibody molecule having a VH domain comprising a set of HCDRs in a human germline framework, e.g. VH3-23. Thus, the VH domain framework regions FR1, FR2 and/or FR3 may comprise framework regions of human germline gene segment VH3-23. FR4 may comprise a framework region of human germline j segment JH1, JH4 or JH5 (these j segments have identical amino acid sequences) or it may comprise a framework region of human germline j segment JH3. The amino acid sequence of VH FR1 may be SEQ ID NO: 189. The amino acid sequence of VH FR2 may be SEQ ID NO: 190. The amino acid sequence of VH FR3 may be SEQ ID NO: 191. The amino acid sequence of VH FR4 may be SEQ ID NO: 192. Normally the binding member also has a VL domain comprising a set of LCDRs, e.g. in a human germline framework, e.g. VX6a. Thus, the VL domain framework regions FR1, FR2 and/or FR3 may comprise framework regions of human germline gene segment Vλ6a. FR4 may comprise a framework region of human germline j segment JL2 or JL3 (these j segments have identical amino acid sequences). The amino acid sequence of VL FR1 may be SEQ ID NO: 193. The amino acid sequence of VL FR2 may be SEQ ID NO: 194. The amino acid sequence of VL FR3 may be 195. The amino acid sequence of VL FR4 may be SEQ ID NO: 196. A germlined VH or VL domain may or may not be germlined at one or more Vernier residues, but is normally not.

An antibody molecule or VH domain of the invention may comprise a VH FR1 wherein Kabat residue 28 is Thr or Ser, e.g. Thr, and/or Kabat residue 30 is Ser or Thr, e.g. Ser.

An antibody molecule or VL domain of the invention may comprise a VL FR2 wherein Kabat residue 49 is a hydrophobic residue e.g. Phe, Tyr or H is, e.g. Phe.

As indicated in Example 7.4, Thr28 and Ser30 in the VH domain framework and Phe49 in the VL domain framework may bind IL-17A.

An antibody molecule or a VH domain of the invention may comprise the following set of heavy chain framework regions:
FR1 SEQ ID NO: 189;
FR2 SEQ ID NO: 190;
FR3 SEQ ID NO: 191;
FR4 SEQ ID NO: 192;
or may comprise the said set of heavy chain framework regions with one, two, three, four or five amino acid alterations, e.g. substitutions.

An antibody molecule or a VL domain of the invention may comprise the following set of light chain framework regions:
FR1 SEQ ID NO: 193;
FR2 SEQ ID NO: 194;
FR3 SEQ ID NO: 195;
FR4 SEQ ID NO: 196;
or may comprise the said set of light chain framework regions with one, two, three, four or five amino acid alterations, e.g. substitutions.

An amino acid alteration may be a substitution, an insertion or a deletion. Alterations are optionally not made at Kabat residue Thr28 in VH FR1, Kabat residue Ser30 in VH FR1 and/or Kabat residue Phe49 in VL FR2.

For example, an antibody molecule of the invention may comprise a set of heavy and light chain framework regions, wherein
heavy chain FR1 is SEQ ID NO: 189;
heavy chain FR2 is SEQ ID NO: 190;
heavy chain FR3 is SEQ ID NO: 191;
heavy chain FR4 is SEQ ID NO: 192;
light chain FR1 is SEQ ID NO: 193;
light chain FR2 is SEQ ID NO: 194;
light chain FR3 is SEQ ID NO: 195;
light chain FR4 is SEQ ID NO: 196;
or may comprise the said set of heavy and light chain framework regions with 10 or fewer, e.g. five or fewer, amino acid alterations, e.g. substitutions. For example there may be one or two amino acid substitutions in the said set of heavy and light chain framework regions.

A non-germlined antibody has the same CDRs, but different frameworks, compared with a germlined antibody.

Of the antibody sequences shown herein, VH domains of antibodies 2, 3, 4, 5, 6, 7, 13, 14 and 15 are germlined, VH domains of antibodies 1, 8, 9, 10, 11, 12 and 16 are not germlined, VL domains of antibodies 2 and 7 are germlined, and VL domains of antibodies 1, 3, 4, 5, 6, 8, 9, 10, 11, 12, 13, 14, 15 and 16 are not germlined.

A binding member of the present invention may be one which competes for binding to IL-17 with any binding member which both binds IL-17 and comprises a binding member, VH and/or VL domain, CDR e.g. HCDR3, and/or set of CDRs disclosed herein. Competition between binding members may be assayed easily in vitro, for example using ELISA and/or by tagging a specific reporter molecule to one binding member which can be detected in the presence of one or more other untagged binding members, to enable identification of binding members which bind the same epitope or an overlapping epitope. Competition may be determined for example using ELISA in which IL-17 is immobilized to a plate and a first tagged binding member along with one or more other untagged binding members is added to the plate. Presence of an untagged binding member that competes with the tagged binding member is observed by a decrease in the signal emitted by the tagged binding member. Such methods are readily known to one of ordinary skill in the art, and are described in more detail herein. In one embodiment, competitive binding is assayed using an epitope competition assay as described herein. A binding member of the present invention may comprise a antibody antigen-binding site that competes with an antibody molecule, for example especially an antibody molecule comprising a VH and/or VL domain, CDR e.g. HCDR3 or set of CDRs of the parent antibody or any of antibodies 1 to 16 for binding to IL-17. Aspects of the invention provide binding members that compete for binding to IL-17 with any binding member defined herein, e.g. compete with the parent antibody or any of antibodies 2 to 16, e.g. in scFv or IgG1 format. A binding member that competes for binding to IL-17 with any binding member defined herein may have any one or more of the structural and/or functional properties disclosed herein for binding members of the invention.

In further aspects, the invention provides an isolated nucleic acid which comprises a sequence encoding a binding member, VH domain and/or VL domain according to the present invention, and methods of preparing a binding member, a VH domain and/or a VL domain of the invention, which comprise expressing said nucleic acid under conditions to bring about production of said binding member, VH domain and/or VL domain, and recovering it.

Another aspect of the present invention provides nucleic acid, generally isolated, encoding a VH CDR or VL CDR sequence disclosed herein.

A further aspect provides a host cell containing or transformed with nucleic acid of the invention.

Further aspects of the present invention provide for compositions containing binding members of the invention, and their use in methods of inhibiting and/or neutralising IL-17, including methods of treatment of the human or animal body by therapy.

Binding members according to the invention may be used in a method of treatment or diagnosis of the human or animal body, such as a method of treatment (which may include prophylactic treatment) of a disease or disorder in a human patient which comprises administering to said patient an effective amount of a binding member of the invention. Conditions treatable in accordance with the present invention include any in which IL-17 plays a role, as discussed in detail elsewhere herein.

These and other aspects of the invention are described in further detail below.

Terminology

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

IL-17

IL-17, or IL-17A, is interleukin-17. References to IL-17 are normally to human IL-17A unless otherwise indicated.

IL-17A is expressed in vivo with a 23 amino acid N-terminal signal peptide, which is cleaved to produce mature IL-17A. A sequence of wild-type mature human IL-17A is SEQ ID NO: 198.

It is conventional to refer to amino acid residues in IL-17 according to residue numbering of the mature sequence, without the signal peptide. Residue numbering of human IL-17 herein refers to the mature sequence SEQ ID NO: 198 unless otherwise indicated. Residue 1 of mature IL-17A is Gly, which is position 24 of the full-length polypeptide.

A sequence of human IL-17 is deposited under Accession number Q16552 (Swiss-Prot), which shows the full-length precursor IL-17A including the signal peptide.

A sequence of cynomolgus IL-17 is shown as SEQ ID NO: 162, encoded by SEQ ID NO: 161.

As described elsewhere herein, IL-17A may be recombinant, and/or may be either glycosylated or unglycosylated. IL-17A is expressed naturally in vivo in N-linked glycosylated form. Glycosylated IL-17A may also be expressed in recombinant systems, e.g. in HEK EBNA cells. IL-17A may be expressed in non-glycosylated form in *E. coli* cells.

Binding Member

This describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A binding member normally comprises a molecule having an antigen-binding site. For example, a binding member may be an antibody molecule or a non-antibody protein that comprises an antigen-binding site.

An antigen binding site may be provided by means of arrangement of CDRs on non-antibody protein scaffolds such as fibronectin or cytochrome B etc. (Haan & Maggos, 2004; Koide 1998; Nygren 1997), or by randomising or mutating amino acid residues of a loop within a protein scaffold to confer binding specificity for a desired target. Scaffolds for engineering novel binding sites in proteins have been reviewed in detail by Nygren et al. (1997). Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs or an HCDR and/or LCDR3, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties such as an ability to enter cells, penetrate deep into tissues or reach targets within other structures, or to bind within protein cavities of the target antigen. Use of antigen binding sites in non-antibody protein scaffolds is reviewed in Wess, 2004. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g. 10th fibronectin type III domain) and lipocalins. Other approaches include synthetic "Microbodies" (Selecore GmbH), which are based on cyclotides—small proteins having intra-molecular disulphide bonds.

In addition to antibody sequences and/or an antigen-binding site, a binding member according to the present invention may comprise other amino acids, e.g. forming a peptide or polypeptide, such as a folded domain, or to impart to the molecule another functional characteristic in addition to ability to bind antigen. Binding members of the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR, e.g. CDR3, or a set of CDRs of the invention will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat 1987, and updates thereof, now available on the Internet (at immuno.bme.nwu.edu or find "Kabat" using any search engine).

By CDR region or CDR, it is intended to indicate the hypervariable regions of the heavy and light chains of the immunoglobulin as defined by Kabat et al., (Kabat 1991a, and later editions). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It can be as short as 2 amino acids although the longest size known is 26. Functionally, HCDR3 plays a role in part in the determination of the specificity of the antibody (Segal 1974; Amit 1986; Chothia 1987; Chothia 1989; Caton 1990; Sharon 1990a; Sharon 1990b; Kabat et al., 1991b).

HCDR1 may be 5 amino acids long, consisting of Kabat residues 31-35.

HCDR2 may be 17 amino acids long, consisting of Kabat residues 50-65.

HCDR3 may be 9 amino acids long, consisting of Kabat residues 95-102.

LCDR1 may be 13 amino acids long, consisting of Kabat residues 24-34.

LCDR2 may be 7 amino acids long, consisting of Kabat residues 50-56.

LCDR3 may be 9 amino acids long, consisting of Kabat residues 89-97.

Antibody Molecule

This describes an immunoglobulin whether natural or partly or wholly synthetically produced. The term also covers any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described later. Antibody fragments that comprise an antibody antigen-binding site include, but are not limited to molecules such as Fab, Fab', Fab'-SH, scFv, Fv, dAb, Fd; and diabodies.

Antibody molecules of the invention may be IgG, e.g. IgG1.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann & Dubel (2001). Phage display, another established technique for generating binding members has been described in detail in many publications such as WO92/01047 (discussed further below) and U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160, 6,521,404 and Kontermann & Dubel (2001). Transgenic mice in which the mouse antibody genes are inactivated and functionally replaced with human antibody genes while leaving intact other components of the mouse immune system, can be used for isolating human antibodies (Mendez 1997).

Synthetic antibody molecules may be created by expression from genes generated by means of oligonucleotides synthesized and assembled within suitable expression vectors, for example as described by Knappik et al. (2000) or Krebs et al. (2001).

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward 1989; McCafferty 1990; Holt 2003), which consists of a VH or a VL domain; (v) isolated CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird 1988; Huston 1988); (viii) bispecific single chain Fv dimers (PCT/US92/09965) and (ix) "diabodies", multivalent or multispecific fragments constructed by gene fusion (WO94/13804; Holliger 1993a). Fv, scFv or diabody molecules may be stabilized by the incorporation of disulphide bridges linking the VH and VL domains (Reiter 1996). Minibodies comprising a scFv joined to a CH3 domain may also be made (Hu 1996). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Antibody fragments of the invention can be obtained starting from any of the antibody molecules described herein, e.g. antibody molecules comprising VH and/or VL domains or CDRs of any of antibodies 1 to 16, by methods such as digestion by enzymes, such as pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain (Holt 2003). VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. A binding member of the present invention may be a dAb comprising a VH or VL domain substantially as set out herein, or a VH or VL domain comprising a set of CDRs substantially as set out herein.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 5, e.g. from 1 to 4, including 1 to 3, or 1 or 2, or 3 or 4, amino acid substitutions may be made in the CDR and/or VH or VL domain.

Bispecific or bifunctional antibodies form a second generation of monoclonal antibodies in which two different variable regions are combined in the same molecule (Holliger 1999). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger 1993b), e.g. prepared chemically or from hybrid hybridomas, or may be any of the bispecific antibody fragments mentioned above. These antibodies can be obtained by chemical methods (Glennie 1987; Repp 1995) or somatic methods (Staerz 1986; Suresh 1986) but likewise by genetic engineering techniques which allow the heterodimerization to be forced and thus facilitate the process of purification of the antibody sought (Merchand 1998). Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against IL-17, then a library can be made where the other arm is varied and an antibody of appropriate specificity selected. Bispecific whole antibodies may be made by alternative engineering methods as described in Ridgeway 1996.

Various methods are available in the art for obtaining antibodies against IL-17. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane 1988) or to the technique of preparation from hybridomas described by Kohler and Milstein, 1975.

Monoclonal antibodies can be obtained, for example, from an animal cell immunized against IL-17, or one of their fragments containing the epitope recognized by said monoclonal antibodies. The IL-17, or one of its fragments, can especially be produced according to the usual working methods, by genetic recombination starting with a nucleic acid sequence contained in the cDNA sequence coding for IL-17 or fragment thereof, by peptide synthesis starting from a sequence of amino acids comprised in the peptide sequence of the IL-17 and/or fragment thereof. The monoclonal antibodies can, for example, be purified on an affinity column on which IL-17 or one of its fragments containing the epitope recognized by said monoclonal antibodies, has previously been immobilized. More particularly, the monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. In one embodiment, the whole of these techniques can be used simultaneously or successively.

Antigen-binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

Isolated

This refers to the state in which binding members of the invention, or nucleic acid encoding such binding members, will generally be in accordance with the present invention. Thus, binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503)) cells, or they may be (for example if produced by expression in a prokaryotic cell) unglycosylated.

Heterogeneous preparations comprising anti-IL-17 antibody molecules also form part of the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

BRIEF DESCRIPTION OF THE DRAWINGS

FIG. 1. N-terminally tagged human IL-17A amino acid sequence (SEQ ID NO: 197). N-terminal tag residues 1 to 21 are shown underlined. Residues 92-108, corresponding to residues 71-87 of mature human IL-17A, are boxed (SEQ ID NO: 199).

FIG. 2. Full-length precursor human IL-17A amino acid sequence with C-terminal His5 tag (SEQ ID NO: 200). N-terminal signal peptide of 23 amino acid residues is shown underlined. Residues mutated from wild-type human IL-17A (SEQ ID NO: 198) are bold and underlined, within boxed sequence SEQ ID NO: 199 corresponding to residues 71-87 of mature human IL-17A. Mature mutant human IL-17A, without N-terminal peptide and His tag, is SEQ ID NO: 201.

DETAILED DESCRIPTION

As noted above, a binding member in accordance with the present invention modulates and may neutralise a biological activity of IL-17. As described herein, IL-17-binding members of the present invention may be optimised for neutralizing potency. Generally, potency optimisation involves mutating the sequence of a selected binding member (normally the variable domain sequence of an antibody) to generate a library of binding members, which are then assayed for potency and the more potent binding members are selected. Thus selected "potency-optimised" binding members tend to have a higher potency than the binding member from which the library was generated. Nevertheless, high potency binding members may also be obtained without optimisation, for example a high potency binding member may be obtained directly from an initial screen e.g. a biochemical neutralization assay. A "potency optimized" binding member refers to a binding member with an optimized potency of neutralization of a particular activity or downstream function of IL-17. Assays and potencies are described in more detail elsewhere herein. The present invention provides both potency-optimized and non-optimized binding members, as well as methods for potency optimization from a selected binding member. The present invention thus allows the skilled person to generate binding members having high potency.

Although potency optimization may be used to generate higher potency binding members from a given binding member, it is also noted that high potency binding members may be obtained even without potency optimization.

In a further aspect, the present invention provides a method of obtaining one or more binding members able to bind the antigen, the method including bringing into contact a library of binding members according to the invention and said antigen, and selecting one or more binding members of the library able to bind said antigen.

The library may be displayed on particles or molecular complexes, e.g. replicable genetic packages such as yeast, bacterial or bacteriophage (e.g. T7) particles, viruses, cells or covalent, ribosomal or other in vitro display systems, each particle or molecular complex containing nucleic acid encoding the antibody VH variable domain displayed on it, and optionally also a displayed VL domain if present. Phage display is described in WO92/01047 and e.g. U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404, each of which is herein incorporated by reference in their entirety.

Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind IL-17 may be further tested, also ability to compete with e.g. a parent antibody molecule or an antibody molecule 1 to 16 (e.g. in scFv format and/or IgG format, e.g. IgG 1) for binding to IL-17. Ability to neutralize IL-17 may be tested, as discussed further elsewhere herein.

A binding member according to the present invention may bind IL-17 with the affinity of one of antibodies 1 to 16 e.g. in scFv or IgG1 format, or with an affinity that is better.

A binding member according to the present invention may neutralize a biological activity of IL-17 with the potency of one of antibodies 1 to 16 e.g. in scFv or IgG1 format, or with a potency that is better.

Binding affinity and neutralization potency of different binding members can be compared under appropriate conditions.

Variants of antibody molecules disclosed herein may be produced and used in the present invention. Following the lead of computational chemistry in applying multivariate data analysis techniques to the structure/property-activity relationships (Wold 1984) quantitative activity-property relationships of antibodies can be derived using well-known mathematical techniques such as statistical regression, pattern recognition and classification (Norman 1998; Kandel & Backer 1995; Krzanowski 2000; Witten & Frank 1999; Denison (Ed) 2002; Ghose & Viswanadhan). The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites (Chothia 1992; Al-Lazikani 1997). These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions (Chothia 1992; Al-Lazikani 1997).

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule (Chothia 1986) using any freely available or commercial package such as WAM (Whitelegg & Rees 2000). A protein visualisation and analysis software package such as Insight II (Accelerys, Inc.) or Deep View (Guex & Peitsch 1997) may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind and/or neutralize IL-17 and/or for any other desired property.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, maybe 5, 4, 3, 2 or 1. Alterations may be made in one or more framework regions and/or one or more CDRs. The alterations normally do not result in loss of function, so a binding member comprising a thus-altered amino acid sequence may retain an ability to bind and/or neutralize IL-17. For example, it may retain the same quantitative binding and/or neutralizing ability as a binding member in which the alteration is not made, e.g. as measured in an assay described herein. The binding member comprising a thus-altered amino acid sequence may have an improved ability to bind and/or neutralize IL-17.

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Example numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. (Voet & Voet 1995). Those amino acid residues that are derivatised at their N-alpha position will only be located at the N-terminus of an amino-acid sequence. Normally in the present invention an amino acid is an L-amino acid, but in some embodiments it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. In some embodiments non-standard amino acids (e.g. D-amino acids) may be incorporated into an amino acid sequence during synthesis, while in other embodiments the non-standard amino acids may be introduced by modification or replacement of the "original" standard amino acids after synthesis of the amino acid sequence.

Use of non-standard and/or non-naturally occurring amino acids increases structural and functional diversity, and can thus increase the potential for achieving desired IL-17-binding and neutralizing properties in a binding member of the invention. Additionally, D-amino acids and analogues have been shown to have better pharmacokinetic profiles compared with standard L-amino acids, owing to in vivo degradation of polypeptides having L-amino acids after administration to an animal e.g. a human.

Novel VH or VL regions carrying CDR-derived sequences of the invention may be generated using random mutagenesis of one or more selected VH and/or VL genes to generate mutations within the entire variable domain. Such a technique is described by Gram et al. (1992), who used error-prone PCR. In some embodiments one or two amino acid substitutions are made within an entire variable domain or set of CDRs. Another method that may be used is to direct mutagenesis to CDR regions of VH or VL genes. Such techniques are disclosed by Barbas et al. (1994) and Schier et al. (1996).

All the above-described techniques are known as such in the art and the skilled person will be able to use such techniques to provide binding members of the invention using routine methodology in the art.

A further aspect of the invention provides a method for obtaining an antibody antigen-binding site for IL-17, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a binding member or an antibody antigen-binding site for IL-17 and optionally with one or more functional properties, e.g. ability to neutralize IL-17 activity. Said VL domain may have an amino acid sequence which is substantially as set out herein. An analogous method may be employed in which one or more sequence variants of a VL domain disclosed herein are combined with one or more VH domains.

As noted above, a CDR amino acid sequence substantially as set out herein may be carried as a CDR in a human antibody variable domain or a substantial portion thereof. The HCDR3 sequences substantially as set out herein represent embodiments of the present invention and for example each of these may be carried as a HCDR3 in a human heavy chain variable domain or a substantial portion thereof.

Variable domains employed in the invention may be obtained or derived from any germ-line or rearranged human variable domain, or may be a synthetic variable domain based on consensus or actual sequences of known human variable domains. A variable domain can be derived from a non-human antibody. A CDR sequence of the invention (e.g. CDR3) may be introduced into a repertoire of variable domains lacking a CDR (e.g. CDR3), using recombinant DNA technology. For example, Marks et al. (1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members of the invention. The repertoire may then be displayed in a suitable host system such as the phage display system of WO92/01047, which is herein incorporated by reference in its entirety, or any of a subsequent large body of literature, including Kay, Winter & McCafferty (1996), so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members. Other suitable host systems include, but are not limited to, yeast display, bacterial display, T7 display, viral display, cell display, ribosome display and covalent display.

Analogous shuffling or combinatorial techniques are also disclosed by Stemmer (1994), who describes the technique in relation to a β-lactamase gene but observes that the approach may be used for the generation of antibodies.

A method of preparing a binding member for IL-17 antigen is provided, which method comprises:
  (a) providing a starting repertoire of nucleic acids encoding a VH domain which either include a CDR3 to be replaced or lack a CDR3 encoding region;
  (b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;
  (c) expressing the nucleic acids of said product repertoire;
  (d) selecting a binding member for IL-17; and
  (e) recovering said binding member or nucleic acid encoding it.

Again, an analogous method may be employed in which a VL CDR3 of the invention is combined with a repertoire of nucleic acids encoding a VL domain that either include a CDR3 to be replaced or lack a CDR3 encoding region.

Similarly, one or more, or all three CDRs may be grafted into a repertoire of VH or VL domains that are then screened for a binding member or binding members for IL-17.

In one embodiment, one or more of the parent, or antibody 2 to 16 HCDR1, HCDR2 and HCDR3, or the parent or antibody 2 to 16 set of HCDRs, may be employed, and/or one or more of the parent or antibody 2 to 16 LCDR1, LCDR2 and LCDR3 or the parent or antibody 2 to 16 set of LCDRs may be employed.

Similarly, other VH and VL domains, sets of CDRs and sets of HCDRs and/or sets of LCDRs disclosed herein may be employed.

In some embodiments, a substantial portion of an immunoglobulin variable domain will comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in some aspects of the invention, binding members comprise a pair of VH and VL domains, single binding domains based on either VH or VL domain sequences form further aspects of the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to bind IL-17. This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques such as those described in that reference. This technique is also disclosed in Marks 1992.

Binding members of the present invention may further comprise antibody constant regions or parts thereof, e.g. human antibody constant regions or parts thereof. For example, a VL domain may be attached at its C-terminal end to antibody light chain constant domains including human Cκ or Cλ chains, e.g. Cλ chains. Similarly, a binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. IgG1 is advantageous, due to its effector function and ease of manufacture. Any synthetic or other constant region variant that has these properties and stabilizes variable regions is also useful in embodiments of the present invention.

Binding members of the invention may be labelled with a detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Suitable labels include, by way of illustration and not limitation, enzymes such as alkaline phosphatase, glucose-6-phosphate dehydrogenase ("G6PDH") and horseradish peroxidase; dyes; fluorescers, such as fluorescein, rhodamine compounds, phycoerythrin, phycocyanin, allophycocyanin, o-phthaldehyde, fluorescamine, fluorophores such as lanthanide cryptates and chelates (Perkin Elmer and C is Biointernational); chemiluminescers such as isoluminol; sensitizers; coenzymes; enzyme substrates; radiolabels including but not limited to $^{125}$I, $^{131}$I, $^{35}$S, $^{32}$P, $^{14}$C, $^{3}$H, $^{57}$Co, $^{99}$Tc and $^{75}$Se and other radiolabels mentioned herein; particles such as latex or carbon particles; metal sol; crystallite; liposomes; cells, etc., which may be further labelled with a dye, catalyst or other detectable group. Suitable enzymes and coenzymes are disclosed in Litman, et al., U.S. Pat. No. 4,275,149, and Boguslaski, et al., U.S. Pat. No. 4,318,980, each of which are herein incorporated by reference in their entireties. Suitable fluorescers and chemiluminescers are disclosed in Litman, et al., U.S. Pat. No. 4,275,149, which is incorporated herein by reference in its entirety. Labels further include chemical moieties such as biotin that may be detected via binding to a specific cognate detectable moiety, e.g. labelled avidin or streptavidin. Detectable labels may be attached to antibodies of the invention using conventional chemistry known in the art.

There are numerous methods by which the label can produce a signal detectable by external means, for example, by visual examination, electromagnetic radiation, heat, and chemical reagents. The label can also be bound to another binding member that binds the antibody of the invention, or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. This second wavelength emission may also transfer energy to a labelled acceptor molecule, and the resultant energy dissipated from the acceptor molecule by emission of light for example fluorescence resonance energy transfer (FRET). Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, which is herein incorporated herein by reference in its entirety.

The binding member, antibody, or one of its functional fragments, can be present in the form of an immunoconjugate so as to obtain a detectable and/or quantifiable signal. The immunoconjugates can be conjugated, for example, with enzymes such as peroxidase, alkaline phosphatase, alpha-D-galactosidase, glucose oxydase, glucose amylase, carbonic anhydrase, acetylcholinesterase, lysozyme, malate dehydrogenase or glucose 6-phosphate dehydrogenase or by a molecule such as biotin, digoxygenin or 5-bromodeoxyuridine. Fluorescent labels can be likewise conjugated to the immunoconjugates or to their functional fragments according to the invention and especially include fluorescein and its derivatives, fluorochrome, rhodamine and its derivatives, GFP (GFP for "Green Fluorescent Protein"), dansyl, umbelliferone, Lanthanide chelates or cryptates eg. Europium etc. The immunoconjugates or their functional fragments can be prepared by methods known to the person skilled in the art. They can be coupled to the enzymes or to the fluorescent labels directly or by the intermediary of a spacer group or of a linking group such as a polyaldehyde, like glutaraldehyde, ethylenediaminetetraacetic acid (EDTA), diethylene-triaminepentaacetic acid (DPTA), or in the presence of coupling agents such as those mentioned above for the therapeutic conjugates. The conjugates containing labels of fluorescein type can be prepared by reaction with an isothiocyanate. Other immunoconjugates can likewise include chemoluminescent labels such as luminol and the dioxetanes, bio-luminescent labels such as luciferase and luciferin, or else radioactive labels such as iodine123, iodine125, iodine126, iodine131, iodine133, bromine77, technetium99m, indium111, indium 113m, gallium67, gallium 68, sulphur35, phosphorus32, carbon14, tritium (hydrogen3), cobalt57, selenium75, ruthenium95, ruthenium97, ruthenium103, ruthenium105, mercury107, mercury203, rhenium99m, rhenium 101, rhenium105, scandium47, tellurium121 m, tellurium122m, tellurium125m, thulium165, thulium167, thulium168, fluorine-8, yttrium 199. The methods known to the person skilled in the art existing for coupling the therapeutic radioisotopes to the antibodies either directly or via a chelating agent such as EDTA, DTPA mentioned above can be used for the radioelements which can be used in diagnosis. It is likewise possible to mention labelling with Na[I 125] by the chloramine T method (Hunter and Greenwood 1962) or else with technetium99m by the technique of Crockford et al., (U.S. Pat. No. 4,424,200, herein incorporated by reference in its entirety) or attached via DTPA as described by Hnatowich (U.S. Pat. No. 4,479,930, herein incorporated by reference in its entirety). Further immunoconjugates can include a toxin moiety such as for example a toxin moiety selected from a group of *Pseudomonas* exotoxin (PE or a cytotoxic fragment or mutant thereof), Diptheria toxin or a cytotoxic fragment or mutant thereof, a botulinum toxin A through F, ricin or a cytotoxic fragment thereof, abrin or a cytotoxic fragment thereof, saporin or a cytotoxic fragment thereof, pokeweed antiviral toxin or a cytotoxic fragment thereof and bryodin 1 or a cytotoxic fragment thereof.

The present invention provides a method comprising causing or allowing binding of a binding member as provided herein to IL-17. As noted, such binding may take place in vivo, e.g. following administration of a binding member, or nucleic acid encoding a binding member, or it may take place in vitro, for example in ELISA, Western blotting, immuno-cytochemistry, immuno-precipitation, affinity chromatography, and biochemical or cell based assays such as are described herein. The invention also provides for measuring levels of antigen directly, by employing a binding member according to the invention for example in a biosensor system.

For instance, the present invention comprises a method of detecting and/or measuring binding to IL-17, comprising, (i) exposing said binding member to IL-17 and (ii) detecting binding of said binding member to IL-17, wherein binding is detected using any method or detectable label described herein. This, and any other binding detection method described herein, may be interpreted directly by the person performing the method, for instance, by visually observing a detectable label. Alternatively, this method, or any other binding detection method described herein, may produce a report in the form of an autoradiograph, a photograph, a computer printout, a flow cytometry report, a graph, a chart, a test tube or container or well containing the result, or any other visual or physical representation of a result of the method.

The amount of binding of binding member to IL-17 may be determined. Quantification may be related to the amount of the antigen in a test sample, which may be of diagnostic interest. Screening for IL-17 binding and/or the quantification thereof may be useful, for instance, in screening patients for diseases or disorders associated with IL-17, such as are referred to elsewhere herein. In one embodiment, among others, a diagnostic method of the invention comprises (i) obtaining a tissue or fluid sample from a subject, (ii) exposing said tissue or fluid sample to one or more binding members of the present invention; and (iii) detecting bound IL-17 as compared to a control sample, wherein an increase in the amount of IL-17 binding as compared to the control may indicate an aberrant level of IL-17 expression or activity. Tissue or fluid samples to be tested include blood, serum, urine, biopsy material, tumours, or any tissue suspected of containing aberrant IL-17 levels. Subjects testing positive for aberrant IL-17 levels or activity may also benefit from the treatment methods disclosed later herein.

Those skilled in the art are able to choose a suitable mode of determining binding of the binding member to an antigen according to their preference and general knowledge, in light of the methods disclosed herein.

The reactivities of binding members in a sample may be determined by any appropriate means. Radioimmunoassay (RIA) is one possibility. Radioactive labelled antigen is mixed with unlabelled antigen (the test sample) and allowed to bind to the binding member. Bound antigen is physically separated from unbound antigen and the amount of radioactive antigen bound to the binding member determined. The more antigen there is in the test sample the less radioactive antigen will bind to the binding member. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin, Texas Red, and lanthanide chelates or cryptates. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes, which catalyze reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual binding member-reporter conjugates may be used to derive quantifiable absolute or relative data of the relevant binding member binding in samples (normal and test).

A kit comprising a binding member according to any aspect or embodiment of the present invention is also provided as an aspect of the present invention. In the kit, the binding member may be labelled to allow its reactivity in a sample to be determined, e.g. as described further below. Further the binding member may or may not be attached to a solid support. Components of a kit are generally sterile and in sealed vials or other containers. Kits may be employed in diagnostic analysis or other methods for which binding members are useful. A kit may contain instructions for use of the components in a method, e.g. a method in accordance with the present invention. Ancillary materials to assist in or to enable performing such a method may be included within a kit of the invention. The ancillary materials include a second, different binding member which binds to the first binding member and is conjugated to a detectable label (e.g., a fluorescent label, radioactive isotope or enzyme). Antibody-based kits may also comprise beads for conducting an immunoprecipitation. Each component of the kits is generally in its own suitable container. Thus, these kits generally comprise distinct containers suitable for each binding member. Further, the kits may comprise instructions for performing the assay and methods for interpreting and analyzing the data resulting from the performance of the assay.

The present invention also provides the use of a binding member as above for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g. via a peptide bond or non-covalently. Linkage via a peptide bond may be as a result of recombinant expression of a gene fusion encoding antibody and reporter molecule.

For example, the present invention includes a method of identifying an IL-17 binding compound, comprising (i) immobilizing IL-17 to a support, (ii) contacting said immobilized IL-17 simultaneously or in a step-wise manner with at least one tagged or labelled binding member according to the invention and one or more untagged or unlabelled test binding compounds, and (iii) identifying a new IL-17 binding compound by observing a decrease in the amount of bound tag from the tagged binding member.

An alternative method of identifying an IL-17 binding compound may comprise (i) immobilizing binding member to a support, (ii) contacting said immobilized binding member simultaneously or in a step-wise manner with tagged IL-17 and one or more untagged or unlabelled test binding members or binding compounds, (iii) identifying a new IL-17 binding compound by observing a decrease in the amount of bound tag from the tagged IL-17.

Such methods can be performed in a high-throughput manner using a multiwell or array format. Such assays may be also be performed in solution for example as an HTRF® assay as described in example 2. See, for instance, U.S. Pat. No. 5,814,468, which is herein incorporated by reference in its entirety. As described above, detection of binding may be interpreted directly by the person performing the method, for instance, by visually observing a detectable label, or a decrease in the presence thereof. Alternatively, the binding methods of the invention may produce a report in the form of an autoradiograph, a photograph, a computer printout, a flow cytometry report, a graph, a chart, a test tube or container or well containing the result, or any other visual or physical representation of a result of the method.

Competition assays can also be used in epitope mapping. In one instance epitope mapping may be used to identify the epitope bound by an IL-17 binding member which optionally may have optimized neutralizing and/or modulating characteristics. Such an epitope can be linear or conformational. A conformational epitope can comprise at least two different fragments of IL-17, wherein said fragments are positioned in proximity to each other when IL-17 is folded in its tertiary or quaternary structure to form a conformational epitope which is recognized by an inhibitor of IL-17, such as an IL-17 binding member. In testing for competition a peptide fragment of the antigen may be employed, especially a peptide including or consisting essentially of an epitope of interest. A peptide having the epitope sequence plus one or more amino acids at either end may be used. Binding members according to the present invention may be such that their binding for antigen is inhibited by a peptide with or including the sequence given.

The present invention further provides an isolated nucleic acid encoding a binding member of the present invention. Nucleic acid may include DNA and/or RNA. In one aspect, the present invention provides a nucleic acid that codes for a CDR or set of CDRs or VH domain or VL domain or antibody antigen-binding site or antibody molecule, e.g. scFv or IgG, e.g. IgG1, of the invention as defined above.

The present invention also provides constructs in the form of plasmids, vectors, transcription or expression cassettes which comprise at least one polynucleotide as above.

The present invention also provides a recombinant host cell that comprises one or more constructs as above. A nucleic acid encoding any CDR or set of CDRs or VH domain or VL domain or antibody antigen-binding site or antibody molecule, e.g. scFv or IgG1 as provided, itself forms an aspect of the present invention, as does a method of production of the encoded product, which method comprises expression from encoding nucleic acid. Expression may conveniently be achieved by culturing under appropriate conditions recombinant host cells containing the nucleic acid. Following production by expression a VH or VL domain, or binding member may be isolated and/or purified using any suitable technique, then used as appropriate.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and binding members comprising a VH and/or VL domain are provided as further aspects of the present invention.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Plückthun 1991. A common bacterial host is *E. coli*.

Expression in eukaryotic cells in culture is also available to those skilled in the art as an option for production of a binding member for example Chadd & Chamow (2001), Andersen & Krummen (2002), Larrick & Thomas (2001). Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (2001). Many known techniques and protocols for manipulation of nucleic acid, for example in preparation of nucleic acid constructs, mutagenesis, sequencing, introduction of DNA into cells and gene expression, and analysis of proteins, are described in detail in Ausubel 1999.

A further aspect of the present invention provides a host cell containing nucleic acid as disclosed herein. Such a host cell may be in vitro and may be in culture. Such a host cell may be in vivo. In vivo presence of the host cell may allow intracellular expression of the binding members of the present invention as "intrabodies" or intracellular antibodies. Intrabodies may be used for gene therapy.

A still further aspect provides a method comprising introducing nucleic acid of the invention into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

In one embodiment, the nucleic acid of the invention is integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above.

Binding members of the present invention are designed to be used in methods of diagnosis or treatment in human or animal subjects, e.g. human. For instance, binding members may be used in diagnosis or treatment of IL-17-associated diseases or disorders, examples of which are referred to elsewhere herein.

Further examples of conditions for which a binding member of the invention may be used in treatment or diagnosis include:

1. Respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2 Bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. Pain and connective tissue remodelling of musculoskeletal disorders due to injury, for example sports injury, or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. Skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. Eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. Gastrointestinal tract: glossitis, gingivitis, periodontitis; oesophagitis, including reflux; eosinophilic gastro-enteritis, mastocytosis, Crohn's disease, colitis e.g. ulcerative colitis, indeterminant colitis, proctitis, microscopic colitis, pruritis ani; Coeliac disease, irritable bowel syndrome, irritable bowel disorder, non-inflammatory diarrhoea and food-related allergies which may have effects remote from the gut (for example migraine, rhinitis or eczema);

7. Abdominal: hepatitis, including autoimmune, alcoholic and viral; fibrosis and cirrhosis of the liver; cholecystitis; pancreatitis, both acute and chronic;

8. Genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. Allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. Other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. Other disorders with an inflammatory or immunological component; including acquired immune deficiency syndrome (AIDS), leprosy, Sezary syndrome, and paraneoplastic syndromes;

13. Cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins; and 14. Oncology: treatment of common cancers including prostate, breast, lung, ovarian, pancreatic, bowel and colon, stomach, skin and brain tumours and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

Thus, binding members of the invention are useful as therapeutic agents in the treatment of conditions involving aberrant IL-17 expression and/or activity. One embodiment, among others, is a method of treatment comprising administering an effective amount of a binding member of the invention to a patient in need thereof, wherein aberrant expression and/or activity of IL-17 is decreased. Another embodiment, among others, is a method of treatment comprising (i) identifying a patient demonstrating aberrant IL-17 levels or activity, for instance using the diagnostic methods described above, and (ii) administering an effective amount of a binding member of the invention to the patient, wherein aberrant expression and/or activity of IL-17 is decreased. An effective amount according to the invention is an amount that decreases the aberrant expression and/or activity of IL-17 so as to decrease or lessen the severity of at least one symptom of the particular disease or disorder being treated, but not necessarily cure the disease or disorder. Accordingly, one embodiment of the invention is a method of treating or reducing the severity of at least one symptom of any of the disorders referred to herein, comprising administering to a patient in need thereof an effective amount of one or more binding members of the present invention alone or in a combined therapeutic regimen with another appropriate medicament known in the art or described herein such that the severity of at least one symptom of any of the disorders is reduced. Another embodiment of the invention, among others, is a method of antagonizing at least one effect of IL-17 comprising contacting with or administering an effective amount of one or more binding members of the present invention such that said at least one effect of IL-17 is antagonized, e.g. IL-17 binding to IL-17RA, or downstream effects such as cytokine release.

Accordingly, further aspects of the invention provide methods of treatment comprising administration of a binding member as provided, pharmaceutical compositions comprising such a binding member, and use of such a binding member in the manufacture of a medicament for administration, for example in a method of making a medicament or pharmaceutical composition comprising formulating the binding member with a pharmaceutically acceptable excipient. A pharmaceutically acceptable excipient may be a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Binding members of the present invention will usually be administered in the form of a pharmaceutical composition, which may comprise at least one component in addition to the binding member. Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled or by injection, e.g. intravenous.

Pharmaceutical compositions for oral administration such as for example nanobodies etc are also envisaged in the present invention. Such oral formulations may be in tablet, capsule, powder, liquid or semi-solid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required, including buffers such as phosphate, citrate, histidine and other organic acids; antioxidants such as ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3'-pentanol; and m-cresol); low molecular weight polypeptides; proteins such as serum albumin, gelatin or immunoglobulins; hydrophilic polymers such as polyvinylpyrrolidone; amino acids such as glycine, glutamine, asparagines, histidine, arginine, or lysine; monosaccharides, disaccharides and other carbohydrates including glucose, mannose or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Binding members of the present invention may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by super-critical fluid technology, for example. Formulations of anti-IL-17 will depend upon the intended route of delivery: for example, formulations for pulmonary delivery may consist of particles with physical properties that ensure penetration into the deep lung upon inhalation; topical formulations may include viscosity modifying agents, which prolong the time that the drug is resident at the site of action. In certain embodiments, the binding member may be prepared with a carrier that will protect the binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art. See, e.g., Robinson, 1978.

Anti-IL-17 treatment with a binding member of the invention may be given orally (for example nanobodies) by injection (for example, subcutaneously, intra-articular, intravenously, intraperitoneal, intra-arterial or intramuscularly), by inhalation, by the intravesicular route (instillation into the urinary bladder), or topically (for example intraocular, intranasal, rectal, into wounds, on skin). The treatment may be administered by pulse infusion, particularly with declining doses of the binding member. The route of administration can be determined by the physicochemical characteristics of the treatment, by special considerations for the disease or by the requirement to optimize efficacy or to minimize side-effects. One particular route of administration is intravenous. Another route of administering pharmaceutical compositions of the present invention is subcutaneously. It is envisaged that anti-IL-17 treatment will not be restricted to use in the clinic. Therefore, subcutaneous injection using a needle-free device is advantageous.

A composition may be administered alone or in combination with other treatments, concurrently or sequentially or as a combined preparation with another therapeutic agent or agents, dependent upon the condition to be treated.

A binding member for IL-17 may be used as part of a combination therapy in conjunction with an additional medicinal component. Combination treatments may be used to provide significant synergistic effects, particularly the combination of an anti-IL-17 binding member with one or more other drugs. A binding member for IL-17 may be administered concurrently or sequentially or as a combined preparation with another therapeutic agent or agents, for the treatment of one or more of the conditions listed herein.

A binding member according to the present invention may be provided in combination or addition with one or more of the following agents:

an antagonist of cytokine function, (e.g. an agent which act on cytokine signalling pathways such as a modulator of the SOCS system), such as an alpha-, beta-, and/or gamma-interferon; modulators of insulin-like growth factor type I (IGF-1), its receptors and associated binding proteins; interleukins (IL) e.g. one or more of IL-1 to 33, and/or an interleukin antagonist or inhibitor such as anakinra; inhibitors of receptors of interleukin family members or inhibitors of specific subunits of such receptors; a tumour necrosis factor alpha (TNF-α) inhibitor such as an anti-TNF monoclonal antibody (for example infliximab; adalimumab, and/or CDP-870), and/or a TNF receptor antagonist e.g. an immunoglobulin molecule (such as etanercept) and/or a low-molecular-weight agent such as pentoxyfylline;

a modulator of B cells, e.g. a monoclonal antibody targeting B-lymphocytes (such as $CD_{20}$(rituximab) or MRA-aIL16R) or T-lymphocytes (e.g. CTLA4-Ig, HuMax Il-15 or Abatacept);

a modulator that inhibits osteoclast activity, for example an antibody to RANKL;

a modulator of chemokine or chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 and CXCR6 (for the C—X—C family) and $CX_3CR1$ for the C—$X_3$—C family;

an inhibitor of matrix metalloproteases (MMPs), i.e., one or more of the stromelysins, the collagenases, and the gelatinases, as well as aggrecanase; especially collagenase-1 (MMP1), collagenase-2 (MMP8), collagenase-3 (MMP13), stromelysin-1 (MMP3), stromelysin-2 (MMP10), and/or stromelysin-3 (MMP11) and/or MMP9 and/or MMP12, e.g. an agent such as doxycycline;

a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; N-(5-substituted)-thiophene-2-alkylsulfonamides; 2,6-di-tert-butylphenolhydrazones; methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; indole and/or a quinoline compound such as MK-591, MK-886, and/or BAY x 1005;

a receptor antagonist for leukotrienes (LT) B4, LTC4, LTD4, and LTE4, selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195;

a phosphodiesterase (PDE) inhibitor such as a methylxanthanine, e.g. theophylline and/or aminophylline; and/or a selective PDE isoenzyme inhibitor e.g. a PDE4 inhibitor and/or inhibitor of the isoform PDE4D, and/or an inhibitor of PDE5;

a histamine type 1 receptor antagonist such as cetirizine, loratadine, desloratadine, fexofenadine, acrivastine, terfenadine, astemizole, azelastine, levocabastine, chlorpheniramine, promethazine, cyclizine, and/or mizolastine (generally applied orally, topically or parenterally);

a proton pump inhibitor (such as omeprazole) or gastro-protective histamine type 2 receptor antagonist;

an antagonist of the histamine type 4 receptor;

an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride, and ethylnorepinephrine hydrochloride;

an anticholinergic agent, e.g. a muscarinic receptor (M1, M2, and M3) antagonist such as atropine, hyoscine, glycopyrrolate, ipratropium bromide, tiotropium bromide, oxitropium bromide, pirenzepine, and telenzepine;

a beta-adrenoceptor agonist (including beta receptor subtypes 1-4) such as isoprenaline, salbutamol, formoterol, salmeterol, terbutaline, orciprenaline, bitolterol mesylate, and/or pirbuterol e.g. a chiral enantiomer thereof;

a chromone, e.g. sodium cromoglycate and/or nedocromil sodium;

a glucocorticoid, such as flunisolide, triamcinolone acetonide, beclomethasone dipropionate, budesonide, fluticasone propionate, ciclesonide, and/or mometasone furoate;

an agent that modulate nuclear hormone receptors such as a PPAR;

an immunoglobulin (Ig) or Ig preparation or an antagonist or antibody modulating Ig function such as anti-IgE (e.g. omalizumab);

other systemic or topically-applied anti-inflammatory agent, e.g. thalidomide or a derivative thereof, a retinoid, dithranol, and/or calcipotriol;

combinations of aminosalicylates and sulfapyridine such as sulfasalazine, mesalazine, balsalazide, and olsalazine; and immunomodulatory agents such as the thiopurines, and corticosteroids such as budesonide;

an antibacterial agent e.g. a penicillin derivative, a tetracycline, a macrolide, a beta-lactam, a fluoroquinolone, metronidazole, and/or an inhaled aminoglycoside; and/or an antiviral agent e.g. acyclovir, famciclovir, valaciclovir, ganciclovir, cidofovir; amantadine, rimantadine; ribavirin; zanamavir and/or oseltamavir; a protease inhibitor such as indinavir, nelfinavir, ritonavir, and/or saquinavir; a nucleoside reverse transcriptase inhibitor such as didanosine, lamivudine, stavudine, zalcitabine, zidovudine; a non-nucleoside reverse transcriptase inhibitor such as nevirapine, efavirenz;

a cardiovascular agent such as a calcium channel blocker, beta-adrenoceptor blocker, angiotensin-converting enzyme (ACE) inhibitor, angiotensin-2 receptor antagonist; lipid lowering agent such as a statin, and/or fibrate; a modulator of blood cell morphology such as pentoxyfylline; a thrombolytic, and/or an anticoagulant e.g. a platelet aggregation inhibitor;

a CNS agent such as an antidepressant (such as sertraline), anti-Parkinsonian drug (such as deprenyl, L-dopa, ropinirole, pramipexole, MAOB inhibitor such as selegine and rasagiline, comP inhibitor such as tasmar, A-2 inhibitor, dopamine reuptake inhibitor, NMDA antagonist, nicotine agonist, dopamine agonist and/or inhibitor of neuronal nitric oxide synthase), and an anti-Alzheimer's drug such as donepezil, rivastigmine, tacrine, COX-2 inhibitor, propentofylline or metrifonate;

an agent for the treatment of acute and chronic pain, e.g. a centrally or peripherally-acting analgesic such as an opioid analogue or derivative, carbamazepine, phenyloin, sodium valproate, amitryptiline or other antidepressant agent, paracetamol, or non-steroidal anti-inflammatory agent;

a parenterally or topically-applied (including inhaled) local anaesthetic agent such as lignocaine or an analogue thereof;

an anti-osteoporosis agent e.g. a hormonal agent such as raloxifene, or a biphosphonate such as alendronate;

(i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitors including VLA-4 antagonist; (vi) a cathepsin; (vii) a kinase inhibitor e.g. an inhibitor of tyrosine kinases (such as Btk, Itk, Jak3 MAP examples of inhibitors might include Gefitinib, Imatinib mesylate), a serine/threonine kinase (e.g. an inhibitor of MAP kinase such as p38, JNK, protein kinases A, B and C and IKK), or a kinase involved in cell cycle regulation (e.g. a cylin dependent kinase); (viii) a glucose-6 phosphate dehydrogenase inhibitor; (ix) a kinin-$B_1$- and/or $B_2$-receptor antagonist; (x) an anti-gout agent, e.g., colchicine; (xi) a xanthine oxidase inhibitor, e.g., allopurinol; (xii) a uricosuric agent, e.g., probenecid, sulfinpyrazone, and/or benzbromarone; (xiii) a growth hormone secretagogue; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) a tachykinin $NK_1$ and/or $NK_3$ receptor antagonist such NKP-608C, SB-233412 (talnetant), and/or D-4418; (xx) an elastase inhibitor e.g. UT-77 and/or ZD-0892; (xxi) a TNF-alpha converting enzyme inhibitor (TACE); (xxii) induced nitric oxide synthase (iNOS) inhibitor or (xxiii) a chemoattractant receptor-homologous molecule expressed on TH2 cells, (such as a CRTH2 antagonist) (xxiv) an inhibitor of a P38 (xxv) agent modulating the function of Toll-like receptors (TLR) and (xxvi) an agent modulating the activity of purinergic receptors such as P2×7; (xxvii) an inhibitor of transcription factor activation such as NFkB, API, and/or STATS.

An inhibitor may be specific or may be a mixed inhibitor, e.g. an inhibitor targeting more than one of the molecules (e.g. receptors) or molecular classes mentioned above.

The binding member could also be used in association with a chemotherapeutic agent or another tyrosine kinase inhibitor in co-administration or in the form of an immuno-conjugate. Fragments of said antibody could also be use in bispecific antibodies obtained by recombinant mechanisms or biochemical coupling, and then associating the specificity of the above described antibody with the specificity of other antibodies able to recognize other molecules involved in the activity for which IL-17 is associated.

For treatment of an inflammatory disease, a binding member of the invention may be combined with one or more agents such as:—Non-steroidal anti-inflammatory agents (hereinafter NSAIDS) including non-selective cyclo-oxygenase (COX)-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate, leflunomide; hydroxychloroquine, d-penicillamine, auranofin or other parenteral or oral gold preparations; analgesics; diacerein; intra-articular therapies such as hyaluronic acid derivatives; and nutritional supplements such as glucosamine.

A binding member of the invention can also be used in combination with an existing therapeutic agent for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab, compounds such as those disclosed in International Patent Applications WO 97/22596, WO 97/30035, WO 97/32856 and WO 98/13354, each of which is incorporated herein in its entirety) and compounds that work by other mechanisms (for example linomide, inhibitors of integrin αvβ3 function and angiostatin);

(vi) vascular damaging agents such as combretastatin A4 and compounds disclosed in International Patent Applications WO 99/02166, WO 00/40529, WO 00/41669, WO 01/92224, WO 02/04434 and WO 02/08213, each of which is incorporated herein in its entirety;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti-idiotypic antibodies.

A binding member of the invention and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration may be in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors, and may depend on the severity of the symptoms and/or progression of a disease being treated. Appropriate doses of antibody are well known in the art (Ledermann 1991 and Bagshawe 1991. Specific dosages indicated herein, or in the Physician's Desk Reference (2003) as appropriate for the type of medicament being administered, may be used. A therapeutically effective amount or suitable dose of a binding member of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody), and the nature of any detectable label or other molecule attached to the antibody. A typical antibody dose will be in the range 100 μg to 1 g for systemic applications, and 1 μg to 1 mg for topical applications. An initial higher loading dose, followed by one or more lower doses, may be administered. Typically, the antibody will be a whole antibody, e.g. the IgG1 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intravenous administration. In some embodiments of the present invention, treatment is periodic, and the period between administrations is about two weeks or more, e.g. about three weeks or more, about four weeks or more, or about once a month. In other embodiments of the invention, treatment may be given before, and/or after surgery, and may be administered or applied directly at the anatomical site of surgical treatment.

EXAMPLES

Example 1

Antibody Lead Isolation 1.1 Selections

Large single chain Fv (scFv) human antibody libraries cloned into a phagemid vector based on filamentous phage M13 were used for selections (Vaughan et al 1996, Hutchings et al 2001). Anti-IL-17A specific scFv antibodies were isolated from the phage display libraries using a series of selection cycles on recombinant human IL-17A essentially as previously described (Vaughan et al 1996). In brief human IL-17A in PBS (Dulbecco's PBS, pH7.4) was adsorbed onto wells of a microtitre plate overnight at 4° C. Wells were washed with PBS then blocked for 1 h with PBS-Marvel (3% w/v). Purified phage in PBS-Marvel (3% w/v) were added to the wells and allowed to bind coated antigen for 1 h. Unbound phage was removed by a series of wash cycles using PBS-Tween (0.1° v/v) and PBS. Bound phage particles were eluted, infected into bacteria and rescued for the next round of selection (Vaughan et al 1996).

A representative number of individual clones from the second round of selections was grown up in 96-well plates. ScFvs were expressed in the bacterial periplasm and screened for their inhibitory activity in a human IL-17 receptor A binding assay. ScFv which showed a significant inhibitory effect on the IL-17A:IL-17RA interaction as crude periplasmic extracts, were subjected to DNA sequencing (Vaughan 1996, Osbourn 1996). Unique scFvs were expressed again in bacteria and purified by affinity chromatography (Bannister et al 2006), and $IC_{50}$ values were determined by testing dilution series of purified scFvs in the HTRF® receptor-ligand binding assay, and in the HT1080 IL-6 release assays against human and cynomolgus IL-17.

1.2 Selectivity and Species Cross Reactivity of Antibodies in DELFIA® Epitope Competition Assays The species cross reactivity and selectivity of antibodies to IL-17 family members was established using DELFIA® epitope competition assays, by measuring inhibition of HIS FLAG IL-17A (in house, HEK EBNA derived), binding each immobilised anti-IL-17 antibody.

Titrations of untagged purified human IL-17A (in house *E. coli* derived), IL-17B (Peprotech), IL-17C(R & D Systems), IL-17D (Peprotech), IL-17E (R & D Systems), and IL-17F (Peprotech) were tested in each assay to establish the potency for each IL-17 family member, as measured by $IC_{50}$ values in the assay.

Titrations of IL-17 species including human, cynomolgus (in house *E. Coli* derived), and murine IL-17A (R & D Systems) were tested in each assay to establish the species cross-reactivity of the antibodies.

Purified IgG were adsorbed onto 96-well Maxisorp microtitre plates (Nunc) in phosphate buffered saline (PBS), at a concentration which gave a significant signal when biotinylated human IL-17A was added at approximately its estimated Kd for that particular IgG. Excess IgG was washed away with PBS-Tween (0.1° v/v) and the wells were blocked with PBS-Marvel (3% w/v) for 1 h. A dilution series of competitor (murine or cynomolgus IL-17A, or IL-17 family members) was prepared in PBS, starting at a concentration of approximately 200-fold the Kd value of the interaction between biotinylated human IL-17A and the respective IgG. Unbiotinylated human IL-17A was used as a positive control. To this series, an equal volume of biotinylated recombinant human IL-17A at a concentration of approximately 2-fold the Kd was added (resulting in a series starting at a ratio of competitor antigen:biotinylated human IL-17A of approximately 100:1). These mixtures were then transferred onto the blocked IgG and allowed to equilibrate for 1 h. Unbound antigen was removed by washing with PBS-Tween (0.1° v/v), while the remaining biotinylated human IL-17A was detected by streptavidin-Europium3+ conjugate (DELFIA® detection, PerkinElmer). Time-resolved fluorescence was measured at 620 nm on an EnVision plate reader (PerkinElmer). Fluorescence data was converted to % specific binding (100% was determined from control wells containing biotinylated human IL-17A but no competitor, 0% was from wells containing biotinylated human IL-17A and a 100-fold excess of unbiotinylated human IL-17A). Resultant data were analysed using Prism curve fitting software (Graphpad) to determine $IC_{50}$ values. Due to the different affinities of each IgG to IL-17A, and therefore the different assay conditions used, results were expressed as fold difference in $IC_{50}$ values between human IL-17A and competing antigens. This enables comparison of different IgG.

TABLE 1

Potency of IL-17 family members and different IL-17 species in human IL-17A binding IgG assays (DELFIA ®)

| | $IC_{50}$ (nM) | | | | | |
|---|---|---|---|---|---|---|
| Clone Name | Human IL-17A | Murine IL-17A | Fold difference from Human IL-17A | Cyno IL-17A | Fold difference from Human IL-17A | Human IL-17 B to F |
| TINA1 | 12 | 98 | 12 | NI | — | NI |
| TINA7 | 28 | NI | — | 4 | 0.14 | ND |
| TINA10 | 7 | 50% | — | 21 | 3 | NI |
| TINA11 | 4 | NI | — | 28 | 7 | NI |
| Antibody 1 | 6 | NI | — | 69 | 11.5 | NI |
| TINA21 | 6 | NI | — | 20 | 3.1 | NI |
| TINA22 | 7 | NI | — | 7 | 1 | ND |
| TINA48 | 9 | NI | — | 7 | 0.8 | NI |
| TINA51 | 25 | 35 | 0.7 | NI | — | NI |

ND indicates not determined,
NI no inhibition.
No inhibition of human IL-17A binding was observed with IL-17B to F for any of the clones tested.

1.3 Inhibition of IL-17A Binding to IL-17 Receptor

Selection outputs were screened in receptor-ligand binding HTRF® (Homogeneous Time-Resolved Fluorescence, CIS Bio international) assay format for inhibition of either, biotinylated human IL-17A (Peprotech 200-17), or HIS FLAG tagged human IL-17A (in house HEK EBNA derived) binding IL-17RA Fc fusion protein (R & D Systems 177-IR). A reference anti-IL-17 mAb (Biosource) was included in all potency assays as a positive control. The detailed assay method is provided in the Assay Materials and Methods section.

Examples of the lead scFv potencies obtained from the HIS FLAG tagged human IL-17A binding IL-17RA Fc fusion protein assay are shown in Table 2.

TABLE 2

Examples of lead scFv potencies in HIS FLAG IL-17A binding IL-17RA Fc assay

| Clone name | $IC_{50}$ (nM) in HTRF ® assay |
|---|---|
| TINA1 | 213 |
| TINA7 | 118 |
| TINA10 | 59 |
| TINA11 | 156 |
| Antibody 1 | 12 |
| TINA21 | 36 |
| TINA22 | 53 |
| TINA48 | 57 |
| TINA51 | 80 |
| TINA55 | 79 |
| TINA62 | 4 |
| TINA107 | 25 |

1.4 Epitope Binding

Lead scFv were tested in epitope competition assays for inhibition of HIS FLAG human IL-17A (in house HEK EBNA derived) binding anti-human IL-17 antibodies including parent Antibody 1, mAb317 (R & D Systems) or the Biosource mAb.

Epitope competition assays using mAb317 or the Biosource mAb involved pre-incubating 3 nM or 6 nM anti-IL-17 antibody with 20 nM or 10 nM anti-murine Fc labelled with XL665 (CIS Bio International 61PAMXLB) in 50 mM HEPES buffer containing 0.4M potassium fluoride and 0.1% BSA (assay buffer) respectively. Antibody and XL665 detection were pre-incubated for 1 h in the dark at room temperature. For the assay using Antibody 1, Antibody 1 was directly labelled with cryptate (CIS Bio International 62EUSPEA) and diluted 500-fold in assay buffer prior to use.

In parallel, for assays using mAb317 or Biosource mAb, 10 nM of biotinylated IL-17A (20 nM monomeric) was pre-incubated for 1 h at room temperature in the dark with 3.2 nM streptavidin cryptate in assay buffer. For the Antibody 1 assay, 2 nM HIS FLAG IL-17A (4 nM monomeric) was pre-incubated for 1 h at room temperature in the dark with 2 nM anti-Flag antibody labelled with XL665 (CIS Bio International 61FG2XLB) in assay buffer.

After pre-incubation of the reagents, 10 μl of purified scFv sample was added to a 384 well low volume assay plate (Costar). This was followed by the addition of 5 μl of the pre-incubated IL-17 antibody and its XL665 detection for assays using mAb317 or the Biosource mAb, and then 5 μl of the human biotinylated IL-17A and cryptate detection mix.

For the Antibody 1 assay, 10 μl of purified scFv sample was added to a 384 well low volume assay plate, followed by the addition of 5 μl of the cryptate labelled Antibody 1, and then 5 μl of the HIS FLAG IL-17A and XL665 detection mix.

Assay plates were then centrifuged at 1000 rpm at room temperature for 1 min, and incubated for up to 4 h at room temperature, prior to reading time-resolved fluorescence at 620 nm and 665 nm emission wavelengths using an EnVision plate reader (Perkin Elmer).

Data was analysed by calculating % Delta F values (CIS Bio International) for each sample, which were then used to determine W specific binding.

Results are summarised in Table 3.

TABLE 3

Example results of lead scFv characterisation in IL-17A epitope competition assays

| Clone name | Inhibition in epitope competition assay against: | | |
|---|---|---|---|
| | Antibody 1 | mAb 317 | Biosource mAb |
| TINA1 | +++ | + | +++ |
| TINA7 | + | + | + |
| TINA10 | +++ | + | +++ |
| TINA11 | +++ | + | +++ |
| TINA12 | +++ | + | +++ |
| TINA21 | +++ | ++ | +++ |
| TINA22 | +++ | +++ | ++ |
| TINA48 | +++ | + | +++ |
| TINA51 | ++ | + | ++ |
| TINA55 | +/− | + | +++ |
| TINA62 | +/− | + | ++ |
| TINA107 | +++ | + | +++ |
| Antibody 1 (TINA12 IgG1) | +++ | − | +++ |
| mAb 317 (R & D systems) | +/− | +++ | +/− |
| Biosource mAb | +++ | +/− | +++ |

+++ good inhibition observed.
+ poor inhibition observed.
− no inhibition observed Different degrees of inhibition were observed between the lead panel of scFv in the 3 epitope competition assays, indicating that some of these clones recognised slightly different or overlapping epitopes from other scFv in the panel, and from the mAbs with which the assays were set-up.

1.5 Reformatting of scFv to IgG1

Clones were converted from scFv to IgG format by subcloning the $V_H$ and $V_L$ domains into vectors expressing whole antibody heavy and light chains respectively. The $V_H$ domain was cloned into a vector (pEU15.1) containing the human heavy chain constant domains and regulatory elements to express whole IgG heavy chain in mammalian cells. Similarly, the $V_L$ domain was cloned into a vector (pEU4.4) for the expression of the human light chain (lambda) constant domains and regulatory elements to express whole IgG light chain in mammalian cells. Vectors for the expression of heavy chains and light chains were originally described in Persic et al, 1997. Cambridge Antibody Technology vectors have been engineered simply by introducing an OriP element. To obtain IgGs, the heavy and light chain IgG expressing vectors were transfected into EBNA-HEK293 mammalian cells. IgGs were expressed and secreted into the medium. Harvests were pooled and filtered prior to purification. The IgG was purified using Protein A chromatography. Culture supernatants are loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralised by the addition of Tris-HCl (pH 9.0). The eluted material was buffer exchanged into PBS using Nap10 columns (Amersham, #17-0854-02) and the concentration of IgG was determined spectrophotometrically using an extinction coefficient based on the amino acid sequence of the IgG Mach et al 1992. The purified IgG were analysed for aggregation or degradation using SEC-HPLC and by SDS-PAGE.

1.6 IL-17 Induced Release of IL-6 from HT1080 Cells

To determine the bioactivity of IL-17 inhibitors, scFv and IgG activity was evaluated in an HT1080 human fibrosarcoma cell assay. These cells respond to human IL-17 by releasing IL-6 in a dose dependent manner. For details of the assay method, see the section "Assay Materials and Methods".

In this assay, the inhibitory activity, as determined by their IC50 values, of a panel of anti-IL-17 scFv/IgG was determined in response to 1 nM human or 1 nM cynomolgus (cyno) non-human primate IL-17A. The scFv and IgG potencies obtained are shown in Table 4.

TABLE 4

Examples of scFv and IgG potencies in the HT1080 assay

| | Human IL-17 | | Cyno IL-17 |
|---|---|---|---|
| Clone name | scFv Inhibition | IgG $IC_{50}$ (nM) | IgG $IC_{50}$ (nM) |
| TINA1 | IA | 50% Inhibition | IA |
| TINA10 | inhibition | 54 ± 26 (n = 3) | 155 ± 26 (n = 3) |
| TINA11 | inhibition | 92 ± 16 (n = 2) | 216 ± 188 (n = 2) |
| Antibody 1 | inhibition | 22 ± 10 (n = 6) | 172 ± 32 (n = 5) |
| TINA21 | inhibition | 29 ± 11 (n = 6) | 28 ± 15 (n = 5) |
| TINA48 | inhibition | 69 ± 15 (n = 3) | 33 ± 4 (n = 3) |
| TINA51 | inhibition | 17 (n = 1) | IA |

NT Not tested
IA Inactive scFv from lead isolation generally gave weak inhibition in the HT1080 assay, such that the potencies could not be determined. Therefore, any scFv exhibiting inhibition in the HT1080 assay were reformatted to IgG1 and re-tested in the assay to determine potency more accurately, and to enable the clones to be ranked.

Example 2

Antibody Optimisation 2.1 Affinity Maturation

Lead antibodies were optimised using a targeted mutagenesis approach and affinity-based phage display selections. Large scFv-phage libraries derived from the lead clones were created by oligonucleotide-directed mutagenesis of the variable heavy ($V_H$) and light ($V_L$) chain complementarity determining regions 3 (CDR3) using standard molecular biology techniques as described (Clackson 2004). The libraries were subjected to affinity-based phage display selections in order to select variants with higher affinity for IL-17A. In consequence, these would show an improved inhibitory activity for IL-17A binding its receptor. The selections were performed essentially as described previously (Thompson 1996). In brief, the scFv-phage particles were incubated with recombinant biotinylated human IL-17A in solution (bio-huIL-17A, in house HEK EBNA derived and modified in house). ScFv-phage bound to antigen were then captured on streptavidin-coated paramagnetic beads (Dynabeads® M-280) following the manufacturer's recommendations. The selected scFv-phage particles were then rescued as described previously (Osbourn 1996), and the selection process was repeated in the presence of decreasing concentrations of bio-huIL-17A (100 nM to 10 pM over 5 rounds). Crude scFv-containing periplasmic extracts were prepared of a representative number of individual clones from the selection outputs and screened for the ability to inhibit the binding of human bio-huIL-17A to human IL-17 receptor A essentially as described in Example 1. Screening hits, i.e. scFv variants, which showed a significantly improved inhibitory effect when compared to their respective parent antibody, were subjected to DNA sequencing, and unique variants were produced as purified scFv for further characterisation (see Example 1).

Some scFv were then selected and were converted to IgG1 as described in Example 1 and tested again. In an effort to realise additional potency gains, improved $V_H$ and $V_L$ were recombined at the transfection step and the resulting IgG1 were assessed. Recombination of VH and VL at transfection level is recognised as a somewhat unpredictable technique, with mixed success at generating antibodies of improved potency. However, fortuitously, in this instance the technique succeeded in producing a number of IgG of high potency, including antibodies 3, 4, 5, 7, 9, 10 and 12, as described below.

2.2 Germlining

The amino acid sequences of the $V_H$ and $V_L$ domains of the optimised anti-IL-17A antibodies were aligned to the known human germline sequences in the VBASE database (Tomlinson 1997), and the closest germline was identified by sequence similarity. For the $V_H$ domains of the Tina 12 antibody lineage this was VH3-23. For the VL domains it was Vλ6a.

Without considering the Vernier residues (Foote & Winter 1992), which were left unchanged, there was 1 change in the frameworks of the $V_H$ domains and 2 changes in the $V_L$ domains, all of which were reverted to the closest germline sequence to identically match human antibodies using standard site directed mutagenesis techniques with the appropriate mutagenic primers. Vernier residues in the VH domain were the C-terminal Arg in VH FR3 (residue number 98 in the VH domain sequence), which was not changed to germline Lys. Vernier residues in the VL domain were Ile in VL FR2 (residue number 47 in the VL domain sequence), which was not reverted to germline Thr, and Phe in VL FR2 (residue number 50 in the VL domain sequence), which was not reverted to germline Tyr.

2.3 HTRF® Receptor-ligand Assay of Optimised Clones

Optimised selection outputs were screened in an HTRF® receptor-ligand binding assay for inhibition of HIS FLAG tagged human IL-17A (in house HEK EBNA derived) binding IL-17RA Fc fusion protein, as described in the assay materials and methods section.

The potencies of purified scFv identified as hits from screening were then determined in the HTRF® receptor-ligand binding assay. Examples of the lead scFv potencies obtained are shown in Table 5. Data shown here are for non-germlined antibody sequences.

TABLE 5

Examples of optimised lead scFv potencies in HTRF receptor-ligand assay

| Clone name | $IC_{50}$ (nM) in HTRF ® assay |
|---|---|
| Antibody 1 | 12.0 |
| Antibody 2 | 0.7 |
| Antibody 3 | ND |
| Antibody 4 | ND |
| Antibody 5 | ND |
| Antibody 6 | 1.7 |
| Antibody 7 | ND |
| Antibody 8 | 0.7 |

TABLE 5-continued

Examples of optimised lead scFv potencies in HTRF receptor-ligand assay

| Clone name | $IC_{50}$ (nM) in HTRF ® assay |
|---|---|
| Antibody 9 | ND |
| Antibody 10 | ND |
| Antibody 11 | 0.6 |
| Antibody 12 | ND |
| Antibody 13 | 1.6 |
| Antibody 14 | 2.5 |
| Antibody 15 | 1.6 |
| Antibody 16 | 1.6 |
| FORD022E03 | 8 |
| FORD023A05 | 6 |
| FORD025D03 | 7 |
| FORD022B08 | 6 |
| FORD023B10 | 4 |
| FORD146B02 | 13 |
| FORD016D04 | 0.6 |
| Biosource mAb | 1.5 |

*ND = not determined, as scFv of these clones not available. These clones were created by recombination at IgG stage.

2.4 HT1080 IL-6 Release Assay of Optimised Clones

Improvements in bioactivity following optimisation of the antibodies from lead isolation were assessed in the HT1080 human fibrosarcoma cell as described in the "Assay Materials and Methods" section. All assays were performed using human IL-17A derived from the HEK-EBNA expression system, and cynomologous IL-17A either from derived from *E. coli* or the HEK EBNA expression systems.

A panel of optimised anti-IL-17 scFv/IgG were evaluated in the HT1080 assay in response to 1 nM human or 1 nM cynomolgus (cyno) IL-17A in a concentration-dependent manner. Example scFv and IgG potencies obtained are shown in Table 6A.

TABLE 6A

Examples of scFv and IgG improved potencies in the HT1080 assay.

| Clone name | Human IL-17 scFv $IC_{50}$ (nM) | Human IL-17 IgG $IC_{50}$ (nM) | Cyno IL-17 scFv $IC_{50}$ (nM) | Cyno IL-17 IgG $IC_{50}$ (nM) | Fold difference in cross-reactivity (IgG) |
|---|---|---|---|---|---|
| Antibody 1 | 70% Inhibition | 23.0 | IA | 144.0 | 6 |
| Antibody 2 | 16.2 | 1.5 | 99.0 | 18.3 | 12 |
| Antibody 3 | — | 0.8 | — | 13.0 | 16 |
| Antibody 4 | — | 0.9 | — | 7.3 | 8 |
| Antibody 5 | — | 1.4 | — | 39.7 | 28 |
| Antibody 6 | 31.2 | 1.5 | 135.8 | 39.6 | 26 |
| Antibody 7 | — | 0.7* | — | 5.0† | 7 |
| Antibody 8 | 34.3 | 2.9 | 96.4 | 53.0 | 18 |
| Antibody 9 | — | 2.3 | — | 9.2 | 4 |
| Antibody 10 | — | 2.2 | — | 4.9 | 2 |
| Antibody 11 | 8.2 | 2.2 | 20% Inhibition | 25.0 | 4 |
| Antibody 12 | — | 2.1 | — | 4.2 | 2 |
| Antibody 13 | 35.9 | 2.0 | 147.0 | 28.8 | 14 |
| Antibody 14 | 36.7 | 1.8 | 99.5 | 29.0 | 16 |
| Antibody 15 | 21.7 | 1.7 | 158.8 | 30.9 | 19 |
| Antibody 16 | 13.0 | 1.6 | 249.0 | 29.5 | 19 |
| FORD023B10 | 24.7 | 3.4 | 14.1 | 1.5 | 2 |
| FORD023A05 | 30.6 | 3.3 | 17.0 | 8.7 | 3 |
| FORD025D03 | 34.1 | 2.5 | 26.3 | 6.6 | 3 |
| FORD022B08 | 39.6 | 4.5 | 22.1 | 4.6 | 1 |
| FORD022E03 | 47.7 | 14.6 | 31.2 | 17.0 | 1 |
| FORD146B02 | 52.1 | 9.3 | 30.7 | 17.5 | 2 |

TABLE 6A-continued

Examples of scFv and IgG improved potencies in the HT1080 assay.

| Clone name | Human IL-17 scFv IC$_{50}$ (nM) | IgG IC$_{50}$ (nM) | Cyno IL-17 scFv IC$_{50}$ (nM) | IgG IC$_{50}$ (nM) | Fold difference in cross-reactivity (IgG) |
|---|---|---|---|---|---|
| mAb 317 (R & D systems) | — | 3.2 | — | 14.1 | 4 |
| Biosource mAb | — | 6.2 | — | 6.8 | 1 |

*Further experiments (dataset n = 15) indicated a geometric mean IC50 value of 0.8, 95% confidence intervals 0.6 to 1.0
†Further experiments (dataset n = 12) indicated a geometric mean IC50 value of 4.8, 95% confidence intervals 3.2 to 6.4.

2.5 HT1080 Cell Assay Measuring Synergised IL-6 Release

HT1080 cells can respond to human IL-17A and human TNFα by synergistically releasing IL-6 in a concentration dependent manner. The bioactivity of optimised Antibodies 2 and 7 to the synergised IL-6 response was assessed using a modification to the HT1080 cell assay method previously described, in which IL-6 release was measured in response to 125 pM human IL-17 and 25 pM human TNFα (see "Assay Materials and Methods" section).

Both Antibodies 2 and 7 neutralised the synergised IL-6 response. Example IC$_{50}$ values are shown in Table 6b.

TABLE 6b

Examples of IgG1 potencies in the IL-17/TNFα HT1080 assay

| Clone name | IgG IC$_{50}$ (nM) |
|---|---|
| Antibody 7 | 0.24(95% CI 0.19-0.28) |
| Antibody 2 | 0.41 |

2.6 Inhibition of Native IL-17a Induced Responses in HT1080 cells

The ability of antibodies to inhibit a native source of IL-17A was assessed using IL-17A derived from primary human T cells. E. Coli derived recombinant IL-17A is non-glycosylated unlike a native source which has an N-linked glycosylation site. Assessing the antibodies using T cell derived IL-17A will ensure activity maintained against a natural source of protein.

T cells from healthy human donors were stimulated using conditions to enhance IL-17A production. These supernatants will contain other cytokines such as TNFα which may synergise with any IL-17A present. Conditioned media from the T cells was added to HT1080 cells in the presence or absence of antibody and IL-6 induction over baseline was assessed. From this, IC$_{50}$ values were calculated. A detailed method for this assay is provided in the Assay Materials and Methods section.

TABLE 6c

Effects of antibodies on T cell supernatant induced IL-6 production in HT1080 cells (IC$_{50}$ values calculated in nM, with 95% confidence intervals)

| Antibody (IgG1) | IC$_{50}$ (nM) Mean (95% CI) | n |
|---|---|---|
| Antibody 2 | 0.25 (0.09-0.74) | 3 |
| Antibody 7 | 0.13 (0.04-0.46) | 3 |

2.7 Selectivity and Species Cross Reactivity of Optimised Antibodies in HTRF® Epitope Competition Assays The selectivity and species cross reactivity of lead antibodies to IL-17 family members was established using HTRF® epitope competition assays, by measuring inhibition of HIS FLAG IL-17A (in house HEK EBNA derived) binding each optimised anti-IL-17 antibody.

Titrations of untagged purified human IL-17A (in house E. coli derived), IL-17B (Peprotech), IL-17C(R&D Systems), IL-17D (Peprotech), IL-17E (R&D Systems), and IL-17F (Peprotech) were tested in each assay to establish the potency for each IL-17 family member, as measured by IC$_{50}$ values in the assay.

Titrations of IL-17 species including human, cynomolgus, dog (all in house E. Coli derived) and murine IL-17A (R & D Systems) were tested in each assay to establish the species cross-reactivity of the optimised antibodies.

Results are summarised in Table 7. Initial data indicated that the lead optimised antibodies tested were selective for human IL-17A, and did not recognise family members IL-17B, C, D, E and F.

In further experiments, partial inhibition was observed with human IL-17F, when used at a concentration of 1 μM or greater, with Antibody 7.

Additionally all optimised antibodies tested recognised human, cynomolgus and dog IL-17A with varying degrees of potency. Murine IL-17A was not recognised by any of the optimised antibodies.

TABLE 7

Potency of IL-17 family members and different IL-17 species in human IL-17A binding optimised IgG assay (HTRF ®)

| Optimised Antibody Assay | IC$_{50}$ nM of IL-17 species/family member | | | | | | | | |
|---|---|---|---|---|---|---|---|---|---|
|  | Human IL-17A | Cyno IL-17A | Murine IL-17A | Dog IL-17A | B | C | D | E | F |
| FORD023A05 | 1.5 | ND | ND | ND | NI | NI | NI | NI | NI |
| Antibody 2 | 2.9 (1.6*) | 4.5 | NI | 34 | NI | NI | NI | NI | NI |

TABLE 7-continued

Potency of IL-17 family members and different IL-17 species in human IL-17A binding optimised IgG assay (HTRF ®)

| Optimised Antibody Assay | IC$_{50}$ nM of IL-17 species/family member | | | | | | | | |
|---|---|---|---|---|---|---|---|---|---|
| | Human IL-17A | Cyno IL-17A | Murine IL-17A | Dog IL-17A | B | C | D | E | F |
| Antibody 7 | 1.4 (0.9*) | 2.0 (1.7*) | NI | 14 (11.9*) | NI | NI | NI | NI | Partial inhibition observed (20% inhibition at approx 1 µM or more) |
| Biosource mAb | 3.7 | 4.0 | NI | 50 nM | NI | NI | NI | NI | NI |

B = human IL-17B
C = human IL-17C
D = human IL-17D
E = human IL-17E
F = human IL-17F
NI = no inhibition
ND = not determined
*Values in brackets represent subsequently calculated average IC$_{50}$ values obtained from 2 or more separate experiments.

Example 3

Affinity of Antibodies for Human IL-17a 3.1 pA$_2$ Analysis

In order to further characterise the anti-IL-17A antibodies pA$_2$ analysis was carried out on antibodies, using the method described in the Assay Materials and Methods section. This was used to estimate the equilibrium dissociation constant (Kd) for the IgG against human IL-17A. Analysis was performed using HT1080 human fibrosarcoma cells and HEK EBNA expressed human IL-17A.

Analysis estimated the anti-IL-17 IgG affinities to be between 65 pM and 550 pM for human IL-17A, with example data shown in Table 8. Analysis was also performed with the Biosource mAb and a negative control mAb. The affinity of the isolated antibodies was shown to be between 2 and 5 fold greater than the Biosource mAb.

TABLE 8a

Example affinities of IgG for human IL-17A

| | pA$_2$ Value | Kd (pM) |
|---|---|---|
| Antibody 2 | 9.73 | 188 |
| Antibody 7 | 9.23 | 553 |
| Biosource mAb | 8.96 | 1100 |

3.2 Binding Affinity Data Using Biosensor Analysis

The BIAcore 2000 (GE Healthcare) was used to assess the kinetic parameters of the interaction between Antibody 7 and different species of IL-17A.

The Biosensor uses the optical effects of surface plasmon resonance (SPR) to study changes in surface concentration resulting from the interaction of an analyte molecule that is flowed over a ligand molecule covalently attached to the dextran layer of a biosensor chip. Typically, a defined concentration of the analyte species is flowed over the coupled ligand and any binding is detected as an increase in local SPR signal (association phase). This is followed by a period of buffer flow, during which dissociation of the analyte species can be observed as a decrease in signal (dissociation phase). The remaining analyte can then be stripped from the chip-bound ligand and the procedure repeated at several different analyte concentrations. A series of controls are usually employed during an experiment to ensure that neither the absolute binding capacity nor kinetic profile of the coupled ligand change significantly during the entire experiment. A proprietary Hepes Buffered Saline (HBS-EP) is typically used as the main diluent buffer for the analyte samples and as the flow buffer during dissociation phase. The experimental data is recorded as arbitrary Resonance Units (RUs, which are arbitrary units that directly correspond to the SPR signal) versus time (seconds). The RUs are directly proportional to changes in the refractive index on the chip surface which in turn is an approximate measure of the mass of analyte bound. The BIAevaluation software package can then be used to process data and fit binding models to the data sets. Returned association ($M^{-1}$ $s^{-1}$) and dissociation ($s^{-1}$) rate constants allow calculation of Association (M−1) and Dissociation (M) Affinity constants.

The affinity of antibody 7 was estimated using a single assay in which the IgG1 was covalently (amine linked) coupled to a proprietary CM3 chip surface to a final 300 R$^U$ surface density. A series of dilutions of recombinant human or cynomolgus IL-17A (0.78-50 nM) were then sequentially passed over antibody 7. The molarity of the ligand was based on 280 nm absorbance and extinction coefficients calculated using published methods. Blank flow cell data was subtracted from the IgG$_1$, and a HBS-EP buffer blank was subtracted from the main data set ("double blank subtraction"). The 1:1 Langmuir model and Bivalent Analyte models were then fitted to the data from each analyte concentration set simultaneously using the BIAevaluation 3.2 software.

The validity of the data was assessed/constrained by the calculated Chi2 and T value (parameter value/offset), which had to be <2 and >100 respectively.

Antibody 7 was immobilised to the surface of a CM3 chip and a series of dilutions of recombinant IL-17 variants (0.78-50 nM) were sequentially passed over the IgG$_1$. Data was fitted simultaneously to the 1:1 Langmuir model (simultaneous $k_a$ $k_d$) and simultaneously to the Bivalent Analyte model (simultaneous ka kd). The Bivalent Analyte model gave better fits as judged by eye and by their superior Chi$^2$ values. An affinity constant (Kd) was then calculated from the ratio of rate constants kd1/ka1.

TABLE 8b

Kinetic analysis of Antibody 7

| Antigen | 1:1 Langmiur $K_D$ (nM) | Bivalent Analyte $K_D$ (nM) |
|---|---|---|
| Human IL-17A (E. coli) | 0.195 | 2.098 |
| Cyno IL-17A (E. coli) | 0.512 | 1.340 |
| Human IL-17A-Flag-His10 (HEK) | 0.171 | 0.41-1.88 |

Example 4

Inhibition of IL-17A Induced Activity in Human Primary Chondrocytes

Destruction of articular cartilage is a feature of many inflammatory diseases including rheumatoid arthritis and osteoarthritis. The main cell type within the articular cartilage of the joint is the chondrocyte. Primary human chondrocytes can be isolated from tissue removed during knee replacement surgery. Cells are extracted from cartilage by collagenase digestion and cultured under aseptic conditions for use in in vitro assays. Chondrocytes when stimulated with recombinant or native IL-17 produce a range of inflammatory and destructive mediators including cytokines (such as IL-6, IL-8), $PGE_2$ and degradative enzymes such as MMP13. The assay is described in detail in the Assay Materials and Methods section herein.

Tables 9a and 10a show preliminary data for IgG1 antibodies used in this assay. Tables 9b and 10b show updated data calculated for a larger data set (increased n numbers).

TABLE 9a

Preliminary data on Inhibition of IL-17A Induced IL-6 release from human primary chondrocytes by anti-IL-17A antibodies

| IgG1 | 0.2 nM IL-17A | n | 2 nM IL-17A | n |
|---|---|---|---|---|
| FORD023A05 | 2.77 (1.05-7.31) | 4 | 5.75 (2.69-12.30) | 4 |
| Antibody 2 (non-GL*) | 0.85 (0.44-1.65) | 4 | 5.76 (3.39-9.90) | 4 |
| Biosource mAb | 1.02 (0.78-1.32) | 9 | 5.18 (4.02-6.67) | 12 |
| TINA10 | 27.23 (10.02-74.00) | 5 | 87.97 (52.92-146.24) | 7 |
| Antibody 1 | 29.85 (11.23-79.29) | 4 | 75.67 (27.55-207.82) | 4 |

Geometric Mean $IC_{50}$ shown in nM (95% confidence limits).
*Antibody 2 was used in non-germlined form in this assay.

TABLE 9b

Updated data on Inhibition of IL-17A Induced IL-6 release from human primary chondrocytes by anti-IL-17A antibodies

| IgG1 | 0.2 nM IL-17A | n | 2 nM IL-17A | n |
|---|---|---|---|---|
| Antibody 2 | 1.52 (0.61-3.78) | 5 | 5.51 (3.54-8.57) | 5 |
| Biosource mAb | 1.03 (0.80-1.33) | 12 | 5.70 (4.64-7.01) | 12 |
| Antibody 7 | 0.51 (0.18-1.43) | 6 | 1.44 (0.79-2.64) | 6 |

Geometric Mean $IC_{50}$ shown in nM (95% confidence limits).

TABLE 10a

Preliminary data on Inhibition of IL-17A Induced IL-8 release from human primary chondrocytes by anti-IL-17A antibodies

| IgG1 | 0.2 nM IL-17A | n | 2 nM IL-17A | n |
|---|---|---|---|---|
| FORD023A05 | 2.77 (1.86-4.11) | 7 | 7.84 (4.12-14.90) | 7 |
| Antibody 2 (non-GL*) | 0.74 (0.46-1.18) | 7 | 3.81 (2.24-6.45) | 7 |
| Antibody 2 | 2.30 | 3 | 7.91 | 3 |
| Antibody 7 | 0.17 | 3 | 1.60 | 3 |
| Biosource mAb | 0.78 (0.52-1.17) | 10 | 3.98 (3.09-5.12) | 14 |
| TINA10 | 21.42 (12.85-35.69) | 7 | 61.96 (45.76-83.90) | 9 |
| Antibody 1 | 18.12 (10.7-30.67) | 4 | 44.47 (39.93-49.53) | 4 |

Geometric Mean $IC_{50}$ shown in nM (95% confidence limits).
*Antibody 2 was tested in germlined and non-germlined forms in this assay.

TABLE 10b

Updated data on Inhibition of IL-17A Induced IL-8 release from human primary chondrocytes by anti-IL-17A antibodies

| IgG1 | 0.2 nM IL-17A | n | 2 nM IL-17A | n |
|---|---|---|---|---|
| Antibody 2 | 1.49 (0.80-2.78) | 8 | 7.18 (4.38-11.75) | 8 |
| Antibody 7 | 0.30 (0.14-0.63) | 8 | 1.30 (1.10-1.54) | 9 |
| Biosource mAb | 0.85 (0.58-1.24) | 14 | 5.09 (4.06-6.37) | 15 |

Geometric Mean $IC_{50}$ shown in nM (95% confidence limits).

TABLE 11

Inhibition of IL-17A Induced MMP13 release from human primary chondrocytes by anti-IL-17A antibodies

| IgG1 | 0.2 nM IL-17A | n | 2 nM IL-17A | n |
|---|---|---|---|---|
| FORD023A05 | 4.79 | 2 | 6.84, >50 | 2 |
| Antibody 2 (non-GL*) | 1.55 | 2 | 11.53 | 2 |
| Biosource mAb | 1.69 (1.01-2.82) | 7 | 11.56 (8.05-16.60) | 7 |
| TINA10 | 59.06 (22.49-155.07) | 6 | Range: 63.4->400 | 7 |
| Antibody 1 | 110.04 (35.29-343.16) | 4 | Range: 147->400 | 5 |

Geometric Mean $IC_{50}$ shown in nM (95% confidence limits).
*Antibody 2 was used in non-germlined form in this assay.

TABLE 12

Inhibition of IL-17A Induced $PGE_2$ release from human primary chondrocytes by anti-IL-17A antibodies

| IgG1 | 2 nM IL-17A | n |
|---|---|---|
| FORD023A05 | 4.75 | 3 |
| Antibody 2 (non-GL*) | 1.94 | 3 |
| Biosource mAb | 2.83 | 3 |
| TINA10 | NT | |
| Antibody 1 | NT | |

Geometric Mean $IC_{50}$ shown in nM (95% confidence limits).
NT: Not tested
*Antibody 2 was used in non-germlined form in this assay.

Example 5

Inhibition of IL-17A Induced In vivo Biological Activity in the Airpouch of Balb C Mice 5.1 Air Pouch Formation Balb C mice were anaesthetised with isoflurane and shaved on the dorsal surface. To form the air pouch, 2.5 ml of filtered sterile air was injected sub-cutaneously at the dorsal midline with a 25 g needle. Mice were transferred to their home cage post recovery and on day 3 mice were gently restrained and the pouch was re-inflated with 2.5 ml of sterile air.

Antibodies (IgG1) were assessed using two methods: pre-mixed, where antibody and IL-17 were mixed together prior to injection, and systemic, where antibody was administered prior to injection of IL-17A. In the case of systemic dosing, antibody was diluted in sterile PBS and injected as a bolus, intra-peritoneally on day 5.

On day 6 mice were again gently restrained and each animal received an intra pouch injection volume of 1 ml of 0.5% methylcellulose containing E. Coli derived human IL-17A (in house reagent) either alone (in the case of control, or systemically dosed animals) or in combination with anti-IL-17 antibodies (pre-mix antibody and IL-17A). In these experiments, antibody and ligand were mixed together and pre-incubated at 37° C. for 30 min prior to injection into the pouch. Mice were returned to their home cages until terminal sampling at which point they were culled with rising concentrations of $CO_2$. To aid recovery of lavage fluid from the pouch, 2 ml of PBS containing 4 mM EDTA was gently injected into the pouch and the pouch was gently palpated for approximately 15 sec. The lavage fluid was gently withdrawn from the pouch and decanted into a graduated polypropylene tube. The retrieved volume was recorded. Samples were kept on ice until processed for storage.

5.2 Lavage Fluid Analysis

Total White Blood Cell (TWBC) Counts

To each Coulter pot containing 10 ml of Isoton, 20 μl of lavage fluid was added. Samples were read in duplicate on a Coulter Z1 counter, a duplicate count was produced for each sample and the background reading was kept to <2000. Cell numbers were then adjusted to take account of the lavage volume retrieved from the pouch.

IL-6 Quantification

Samples were centrifuged at 1500 rpm for 5 min and 300 μl of supernatant was aliquoted into 96 well plates in triplicate and stored at −20° C. until ready for analysis. 50 μl of standards, controls and lavage fluid samples were analysed by R & D Systems Quantikine Mouse IL-6 cytokine ELISA kit (Catalogue # M6000B) as per kit protocol.

Concentrations of IL-6 in lavage fluid were determined from the mouse IL-6 standard curve using the SoftMax Pro ELISA plate reader at 450 nm and correction wavelength of 540 nm.

5.3 Inhibition of IL-17A Induced IL-6 Release in the Airpouch

TABLE 13A

Inhibition of IL-17A induced IL-6 release in mouse airpouch: pre-mixed antibody and IL-17A

| Antibody (IgG1) | IL-6 Maximum % Inhibition | $ID_{50}$ μg |
|---|---|---|
| Antibody 2 (non-GL*) | 46 ± 9 | 4 ± 3 |

TABLE 13A-continued

Inhibition of IL-17A induced IL-6 release in mouse airpouch: pre-mixed antibody and IL-17A

| Antibody (IgG1) | IL-6 Maximum % Inhibition | $ID_{50}$ μg |
|---|---|---|
| FORD023A05 | 51 ± 15 | 10 ± 11 |
| Biosource mAb | 96 ± 8 | 6 ± 2 |
| Antibody 7 | 115.9 | 0.5 |

*Antibody 2 was used in non-germlined form in this assay.

TABLE 13b

Inhibition of IL-17A induced IL-6 release in mouse airpouch: systemic administration of antibody

| Antibody (IgG1) | IL-6 Maximum % Inhibition | ID50 μg (95% CI) |
|---|---|---|
| Antibody 7 | 85.2 | 0.056 (−0.071-0.184) |

5.4 Inhibition of IL-17A Induced Influx of White Blood Cells in the Airpouch

TABLE 14a

Inhibition of IL-17A induced influx of leukocytes in airpouch: pre-mixed antibody and IL-17A

| Antibody (IgG1) | TWBC Counts Maximum % Inhibition | $ID_{50}$ μg |
|---|---|---|
| Antibody 2 (non-GL*) | 110 ± 23 | 1 ± 0.4 |
| FORD023A05 | 91 ± 5 | 17 ± 12 |
| Biosource mAb | 71 ± 7 | 3 ± 1.4 |
| Antibody 7 | 111 | 0.3 |

*Antibody 2 was used in non-germlined form in this assay.

TABLE 14b

Inhibition of IL-17A induced influx of leukocytes in airpouch: systemic administration of antibody

| Antibody (IgG1) | TWBC Maximum % Inhibition | $ID_{50}$ μg (95% CI) |
|---|---|---|
| Antibody 7 | 100.9 | 0.617 (−0.518-1.752) |

Example 6

IL-17A/TNFα Synergy Assays 6.1 IL-17A/TNFα Synergy in Post Mortem Cartilage Explants Destruction of articular cartilage is a feature of many inflammatory diseases including rheumatoid arthritis and osteoarthritis. The main cell type within the articular cartilage of the joint is the chondrocyte. Human cartilage can be isolated from tissue removed during knee replacement surgery or from post-mortem donors. Explant discs are cut from cartilage and cultured under aseptic conditions for use in in vitro assays, retaining the chondrocytes within their cellular matrix. Explants when stimulated with IL-17A or TNFα produce a range of inflammatory and destructive mediators including cytokines such as IL-6. A detailed method for this assay is provided in the Assay Materials and Methods section.

In initial experiments to assess functional effects of antibodies in IL-17/TNFα synergy assay in cartilage explants, $IC_{50}$ data were not generated due to limited tissue supply. % inhibition vs. the response in the absence of binding member (0% inhibition) was calculated for a given concentration of binding member. Data are shown in Table 15a. In further experiments IC50 data were calculated, as shown in Table 15b.

IL-17A and TNFα in combination induced a synergised IL-6 response, which was inhibited by IL-17A neutralising antibodies. Isotype control antibodies did not affect the synergised response.

TABLE 15a

Effects of antibodies on IL-17A and TNFα synergised IL-6 responses in human post-mortem cartilage explants (error = standard deviation of 12 replicates, n = 1 donor)

| Antibody (IgG1) | IL-6 (pg/ml) Mean | SEM (+/−) | % inhibition |
|---|---|---|---|
| IL-17A 10 ng/ml | 0.38 | 0.16 | — |
| TNF 1 ng/ml | 6.19 | 3.32 | — |
| IL-17A + TNF | 55.00 | 4.62 | 0 |
| IL-17A + TNF + Biosource mAb | 4.91 | 1.08 | 91.1 |
| IL-17A + TNF + mIgG1 isotype control | 47.41 | 5.77 | 13.8 |
| IL-17A + TNF + Antibody 2 (non-GL*) | 4.63 | 2.30 | 91.6 |
| IL-17A + TNF + hIgG1 isotype control | 53.17 | 8.59 | 3.3 |

*Antibody 2 was used in non-germlined form in this assay.

TABLE 15b $IC_{50}$s of antibodies on IL-17A and TNFα synergised IL-6 responses in human post-mortem cartilage explants (mean data, 95% confidence intervals)

| Antibody (IgG1) | Mean $IC_{50}$ (95% CI) | n |
|---|---|---|
| Antibody 2 | 3.39 | 2 |
| Antibody 7 | 0.61 (0.26-1.42) | 5 |

6.2 IL-17A/TNFα Synergy in OA Synovial Fibroblasts

A feature of joint damage in diseases such as rheumatoid arthritis includes the presence of an inflamed synovium composed of cells of the immune system including e.g. macrophages, T cells, B cells and proliferating fibroblasts. Inflamed synovium can be isolated from joint tissue removed during joint replacement surgery. Synovium is collagenase digested and the isolated cells cultured under aseptic conditions for use in in vitro assays, with a predominantly fibroblast cellular composition. Fibroblasts when stimulated with IL-17A or TNFα produce a range of inflammatory and destructive mediators including cytokines such as IL-8. A detailed method for this assay is provided in the Assay Materials and Methods section.

IL-17A and TNFα together induced a synergised IL-8 response using two different sets of cytokine concentrations. This response was reduced using IL-17A neutralising antibodies although isotype control antibodies had no effect on the synergised response.

TABLE 16a

Effects of antibodies on IL-17A (10 ng/ml) and TNFα (1 ng/ml) synergised IL-8 responses in human OA synovial fibroblasts (cytokine concentrations in pg/ml, error = standard deviation of triplicate data points, n = 1 donor)

| Antibody (IgG1) | IL-8 (pg/ml) Mean | % Inhibition |
|---|---|---|
| IL-17A 10 ng/ml + TNF 1 ng/ml | 62519.10 | 0 |
| IL-17A + TNF + hIgG1 isotype control | 64967.81 | −3.9 |
| IL-17A + TNF + FORD23A05 | 32117.64 | 48.6 |
| IL-17A + TNF + Antibody 2 | 23340.13 | 62.7 |
| IL-17A + TNF + Antibody 7 | 20829.47 | 66.7 |

TABLE 16b

Effects of antibodies on IL-17A (1 ng/ml) and TNFα (0.01 ng/ml) synergised IL-8 responses in human OA synovial fibroblasts (cytokine concentrations in pg/ml, error = standard deviation of triplicate data points, n = 1 donor)

| Antibody (IgG1) | IL-8 (pg/ml) Mean | % Inhibition |
|---|---|---|
| IL-17A 1 ng/ml + TNF 0.01 ng/ml | 3255.86 | 0 |
| IL-17A + TNF + hIgG1 isotype control | 3298.59 | −1.3 |
| IL-17A + TNF + FORD023A05 | 1731.59 | 46.8 |
| IL-17A + TNF + Antibody 2 | 1506.59 | 53.7 |
| IL-17A + TNF + Antibody 7 | 1107.75 | 66.0 |

6.3 Inhibition of IL-17A and IL-17A/TNFα induced IL-8 in RA synovial fibroblasts As outlined in 6.2, inflamed synovium is a key feature of RA. RA synovium can also be isolated from joint tissue removed during RA joint replacement surgery using the same methods as described. These cells are disease relevant and respond to IL-17A and TNFα by producing cytokines including IL-8. A synergistic response is produced when both cytokines are added simultaneously. A detailed method for this assay is provided in the Assay Materials and Methods section.

TABLE 17

Effects of antibodies ($IC_{50}$s) on IL-17A and IL-17A/TNFα induced IL-8 responses in human RA synovial fibroblasts (mean data, 95% confidence intervals)

| Antibody (IgG1) and stimulation | Mean IC50 nM, 95% CI | n |
|---|---|---|
| Antibody 7 versus IL-17A (2 nM) | 2.85 (1.96-4.15) | 3 |
| Antibody 7 versus IL-17A (1 nM) and TNFα (0.1 ng/ml) | 4.97 (1.48-16.73) | 3 |

Example 7

Epitope Mapping of the Binding of Antibody 7 to Human IL-17A 7.1 Perturbation of H/D Exchange Rate of IL-17A by Antibody 7

In the first experiment the IL-17A was exchanged for $D_2O$ in solution, bound to antibody 7 (IgG1) immobilised on a column, and then back exchanged in H$_2$O while still bound to the antibody column, resulting in the epitope being protected during the back exchange reaction and consequently labelled with deuterons. In the second experiment the IL-17A was first bound to antibody 7 (IgG1) on the column, then labelled with D$_2$O and finally exchanged back into H$_2$O while still bound to the column, such that no parts of the IL-17A were labelled with deuterons. The difference in masses of peptides between the two experiments were then determined. The difference in deuteration levels between the two experiments is a measure of the retardation of exchange when bound to antibody. A detailed method for this protocol is provided in the Materials and Methods section.

N-terminally tagged IL-17A was used in this study with the sequence shown in FIG. 1 (SEQ ID NO: 197). Residues 1-21 represent a peptide tag which was added for detection purposes and comprises "Avitag™", which allows enzymatic biotinylation specifically at a lysine residue in the tag. Gly22 is the first residue of mature IL-17A.

The only region to show a significant perturbation in the rate of H/D exchange was between amino acids 92-108 of SEQ ID NO: 197 shown in FIG. 1 encompassing the sequence CRHLGCINADGNVDYHM (SEQ ID NO: 199). This sequence corresponds to residues 71-87 of mature human IL-17A (SEQ ID NO: 198).

TABLE 18

Percentage difference in deuteration levels comparing deuteration and exchange back to protons when bound to antibody 7 with deuteration in solution and exchange back to protons when bound to antibody. Differences of more than 10% especially at early time points were considered to be significant. Residue numbering is with the sequence shown in FIG. 1 (SEQ ID NO: 197)

| Residue number | | Time point (s) | | | |
|---|---|---|---|---|---|
| start | end | 150 | 500 | 1500 | 5000 |
| 3 | 8 | −5 | 0 | −4 | 1 |
| 11 | 17 | −4 | −3 | −1 | −1 |
| 20 | 44 | −3 | −3 | −1 | −3 |
| 47 | 63 | −1 | −2 | −2 | −2 |
| 66 | 74 | −8 | −13 | −12 | −13 |
| 77 | 89 | −1 | −1 | 1 | −2 |
| 92 | 108 | −23 | −21 | −15 | −13 |
| 111 | 118 | −3 | −2 | −2 | −2 |
| 121 | 131 | −5 | −3 | −1 | −2 |
| 134 | 137 | −3 | −2 | 0 | 0 |
| 140 | 153 | −5 | −9 | −8 | −3 |

7.2 Analysis of Binding of Mutant IL-17A to Antibody 7

A second approach was taken to confirm that the epitope identified in example 7.1 is correct. This took advantage of the observation that antibody 7 does not bind to murine IL-17A although mur TABLE 20b Examples of IC$_{50}$s of antibody 7 against IL-17A or mutant IL-17A in the HT1080 assay

| Ligand | Source | [Ligand] (nM) | Antibody 7 IC$_{50}$ (nM) |
|---|---|---|---|
| IL-17A | Peprotech (E. Coli) | 1 | 0.35 |
| IL-17A | In-house (HEK EBNA) | 2 | 0.43 |
| Mutant IL-17A | In-house (HEK EBNA) | 1 | No inhibition |

7.4 X-ray Crystal Structure Determination of the IL-17A Antibody Complex

A structure of IL-17A bound to Antibody 7 Fab was determined by X-ray crystallography. The methods of Fab production, IL-17A protein preparation, crystallisation and crystallography are set out in the Materials and Methods section.

Crystals of the IL-17A/Fab complex were obtained that were thin plates of the monoclinic space group P2$_1$. Complete diffraction data to 2.6 Å resolution were obtained. The structure could be solved by Molecular Replacement using a Fab fragment as a trial model, thereby orienting and positioning the Fab fragments in the crystallographic asymmetric unit. There were four Fab fragments in the asymmetric unit. There was additional electron density into which the IL-17A dimer could be modelled. Two IL-17A dimers were found in the asymmetric unit.

In the crystal structure, each IL-17A dimer is bound to two Fab fragments. The IL-17A dimer is an elongated molecule which is characterised by long beta-strands. The structure is similar to that reported for IL-17F (Hymowitz et al, 2001). The IL-17A dimer is sandwiched between two Fab fragments. The two interaction sites are equivalent; they are related by the IL-17A dimer symmetry. A portion of the IL-17A dimer distal from the binding Fab fragments is disordered, which is to say it is flexible and adopts different orientations throughout the crystal such that the electron density is averaged out. Thus, it is not possible to build a model of this part of the IL-17A dimer. The complex, therefore, makes crystal lattice interactions that are mediated through the Fab molecules only. To use the descriptors used by Hymowitz et al. (2001), the epitope interaction sites are near the "collar" of the structure, while the "skirt" region at the opposite end is disordered.

The crystal structure allows the epitope interactions between IL-17A and Fab to be examined in atomic detail. These are shown in Table 22.

TABLE 22

IL-17A/Fab direct interactions

| IL-17A Hydrogen bonds | Fab | Fab Kabat no. | Distance [Å] |
|---|---|---|---|
| Ser A40 O | Ser H30 OG | H30* | 2.9 |
| Asp A42 N | Ser H31 OG | H31 | 3.2 |
| Asp A42 OD1 | Thr H28 OG | H28 | 2.9 |
| Asp A42 OD1 | Tyr H32 OH | H32 | 2.7 |
| Arg A46 NH2 | Leu H100 O | H96 | 2.6 |
| Arg A46 NH1 | Ser H31 0 | H31 | 2.8 |
| Tyr B85 O | Tyr L94 OH | L91 | 2.5 |
| His B86 NE2 | Ala L30 O | L29 | 3.0 |
| Asn B88 OD1 | His H102 N | H98 | 2.8 |

TABLE 22-continued

IL-17A/Fab direct interactions

| IL-17A Hydrogen bonds | Fab | Fab Kabat no. | Distance [Å] |
|---|---|---|---|
| Non-polar (distance corresponds to closest atom pair) | | | |
| Ser A40 | Thr H28 | H28* | 3.5 |
| Ser A41 | Thr H28 | H28* | 3.7 |
| Tyr A43 | Ser H31 | H31 | 3.6 |
| Ser A41 | Ser H31 | H31 | 3.4 |
| Arg A46 | Tyr H32 | H32 | 3.4 |
| His B86 | Asn L31 | L30 | 3.5 |
| His B86 | Tyr L32 | L31 | 3.8 |
| Tyr B85 | Tyr L32 | L31 | 3.7 |
| His B86 | Tyr L33 | L32 | 3.4 |
| Pro B126 | Tyr L33 | L32 | 3.3 |
| Pro B126 | Phe L50 | L49* | 3.4 |
| Ile B127 | Gln L54 | L53 | 3.2 |
| Tyr B85 | Pro L96 | L93 | 3.7 |
| Leu B74 | Pro L96 | L93 | 3.6 |
| Leu B74 | Tyr H59 | H58 | 3.6 |
| Pro B126 | Leu H100 | H96 | 3.6 |
| Asn B88 | Ile H101 | H97 | 3.4 |
| Met B87 | Ile H101 | H97 | 3.8 |
| His B86 | Ile H101 | H97 | 3.8 |
| Leu B74 | His H102 | H98 | 3.9 |

In Table 22, the residue number contains a chain indicator (H: Fab Heavy chain, L: Fab Light chain, A: monomer A in IL-17A, B: monomer P in IL-17A). Residue numbering of IL-17A corresponds to the mature sequence SEQ ID NO: 198. Residue numbering of the Fab VH and VL domains corresponds to SEQ ID NO: 62 and SEQ ID NO: 176 respectively. Kabat residue numbering for the Fab is also shown. *Asterisks indicate Fab framework residues. The distance cut-off used for hydrogen bonds is 3.2 Å, for non-polar interactions 4.0 Å.

The distances were obtained using the CCP4 program CONTACT (CCP4, 1994). It is only necessary to describe one of the two interactions sites, since they are equivalent. The interactions involve the complementarity determining regions (CDRs) from both the Heavy and the Light chain of the antibody fragment, and amino acid residues from both monomers in the IL-17A dimer. The antibody Heavy chain interacts with both chains A and B in the IL-17A dimer, while the Light chain interacts only with monomer B. The amino acid residues in IL-17A that form part of the interaction site are Ser40 to Tyr43 inclusive and Arg46 in the A chain, and Leu74, Pro91, Tyr85 to Asn88 and Pro126 to Ile127 in the B chain of the dimer. Residues contributed from the Fab Light chain are Ala30 to Tyr33, inclusive, Phe50, Gln54, Tyr94 and Pro96. Residues from the Heavy chain are Thr28, Ser30 to Tyr32, Tyr59, and L100 to H102. Thus, in IL-17A, twelve amino acids form the epitope site, interacting with sixteen amino acid residues in the antibody. The interactions include 9 hydrogen bonds and non-polar van der Waals interactions (also termed hydrophobic interactions). Some of the hydrophobic interactions include electronic stacking interactions, involving the pi electrons in an aromatic system.

Examination of the crystal structure indicated that some of the residues of the Fab that appear to interact with IL-17 could be substituted for other residues that would maintain an interaction.

For example, hydrogen bonding between Ala30L (Kabat residue 29 in LCDR1) and the IL-17 is to the main chain oxygen of the alanine and does not involve the Ala side chain, which is located at the surface of the binding member. This indicates that other amino acid residues could be substituted for Ala at this position without loss of the interaction, and thus would not result in loss of affinity of the binding member for IL-17A.

Hydrogen bonds are also formed between atoms of the main chain of the binding member at Ser31H, Leu100H, Ala30L and His102H, indicating that other residues could be substituted at these positions without losing these hydrogen bonds.

The main chain C-alpha of Asn31L (Kabat residue 30 in LCDR1) forms a non-polar interaction with IL-17, which would also be unaffected by substituting this residue.

The following are further, non-exhaustive, examples of residues that are indicated to interact with IL-17, based on an examination of the structure, and consideration of the locations and nature of interactions, and steric constraints:

Ser, Ala, Gly, Thr or Cys at Kabat residue 31 of HCDR1
Tyr at Kabat residue 32 of HCDR1
Tyr or Phe at Kabat residue 58 of HCDR2
a hydrophobic residue, e.g. Leu, Ile, Val, Ala or Phe, at Kabat residue 96
a hydrophobic residue, e.g. Ile, Leu, Val, Ala or Phe, at Kabat residue 97 of HCDR3
a cyclic residue, e.g. H is, Trp or Phe at Kabat residue 98 of HCDR3
Tyr or Phe at Kabat residue 31 of LCDR1
Tyr or Phe at Kabat residue 32 of LCDR1
a polar residue, e.g. Gln, at Kabat residue 53 of LCDR2
Tyr at Kabat residue 91 of LCDR3
Pro, hydroxyproline, H is, 3-methylhistidine or Asp at Kabat residue 93 of LCDR3
Thr or Ser at Kabat residue 28 in heavy chain FR1
Ser or Thr at Kabat residue 30 in heavy chain FR1
a hydrophobic residue, e.g. Phe, Tyr or H is at Kabat residue 49 in light chain FR2.

TABLE 21

CDR Sequences of Antibodies 1 to 16

| Kabat | HCDR1 | | | | | HCDR2 | | | | | | | | | | | | | | | | |
|---|---|---|---|---|---|---|---|---|---|---|---|---|---|---|---|---|---|---|---|---|---|---|
| numbering | 31 | 32 | 33 | 34 | 35 | 50 | 51 | 52 | 52A | 53 | 54 | 55 | 56 | 57 | 58 | 59 | 60 | 61 | 62 | 63 | 64 | 65 |
| Antibody 01 | S | Y | A | M | S | A | I | S | G | S | G | G | S | T | Y | Y | A | D | S | V | K | G |
| Antibody 02 | | | | | | | | | | | | | | | | | | | | | | |
| Antibody 03 | | | | | | | | | | | | | | | | | | | | | | |
| Antibody 04 | | | | | | | | | | | | | | | | | | | | | | |
| Antibody 05 | | | | | | | | | | | | | | | | | | | | | | |
| Antibody 06 | | | | | | | | | | | | | | | | | | | | | | |
| Antibody 07 | | | | | | | | | | | | | | | | | | | | | | |
| Antibody 08 | | | | | | | | | | | | | | | | | | | | | | |
| Antibody 09 | | | | | | | | | | | | | | | | | | | | | | |
| Antibody 10 | | | | | | | | | | | | | | | | | | | | | | |
| Antibody 11 | | | | | | | | | | | | | | | | | | | | | | |
| Antibody 12 | | | | | | | | | | | | | | | | | | | | | | |
| Antibody 13 | | | | | | | | | | | | | | | | | | | | | | |
| Antibody 14 | | | | | | | | | | | | | | | | | | | | | | |
| Antibody 15 | | | | | | | | | | | | | | | | | | | | | | |
| Antibody 16 | | | | | | | | | | | | | | | | | | | | | | |

| Kabat | HCDR3 | | | | | | | | | LCDR1 | | | | | | | | | |
|---|---|---|---|---|---|---|---|---|---|---|---|---|---|---|---|---|---|---|---|
| numbering | 95 | 96 | 97 | 98 | 99 | 100 | 100A | 101 | 102 | 24 | 25 | 26 | 27 | 27A | 27B | 28 | 29 | 30 | 31 |
| Antibody 01 | D | L | I | W | G | V | A | G | S | T | R | S | S | G | S | L | A | N | Y |
| Antibody 02 | | | | | | | | | | | | | | | | | | | |
| Antibody 03 | | | | H | | | T | R | N | | | | | | | | | | |
| Antibody 04 | | | | H | | | T | R | N | | | | | | | | | | |
| Antibody 05 | | | | H | | | T | R | N | | | | | | | | | | |
| Antibody 06 | | | | | | | | | | | | | | | | | | | |
| Antibody 07 | | | | H | | | T | R | N | | | | | | | | | | |
| Antibody 08 | | | | | | | | | | | | | | | | | | | |
| Antibody 09 | | | | F | | | G | | G | | | | | | | | | | |
| Antibody 10 | | | | F | | | G | | G | | | | | | | | | | |
| Antibody 11 | | | | | | | | | | | | | | | | | | | |
| Antibody 12 | | | | F | | | G | | G | | | | | | | | | | |
| Antibody 13 | | | | | | | | | | | | | | | | | | | |
| Antibody 14 | | | | | | | | | | | | | | | | | | | |
| Antibody 15 | | | | | | | | | | | | | | | | | | | |
| Antibody 16 | | | | | | | | | | | | | | | | | | | |

| Kabat | LCDR1 | | | LCDR2 | | | | | | | LCDR3 | | | | | | | | |
|---|---|---|---|---|---|---|---|---|---|---|---|---|---|---|---|---|---|---|---|
| numbering | 32 | 33 | 34 | 50 | 51 | 52 | 53 | 54 | 55 | 56 | 89 | 90 | 91 | 92 | 93 | 94 | 95 | 96 | 97 |
| Antibody 01 | Y | V | Q | A | N | N | Q | R | P | S | Q | S | Y | D | D | S | S | V | V |
| Antibody 02 | | | | | | | | | | | | | | | P | H | | | |
| Antibody 03 | | | | | | | | | | | | | | S | P | H | | | |
| Antibody 04 | | | | | | | | | | | | | | S | P | T | | | |
| Antibody 05 | | | | | | | | | | | | | | N | H | K | D | I | |
| Antibody 06 | | | | | | | | | | | | | | S | P | | | | |
| Antibody 07 | | | | | | | | | | | | T | | | P | Y | | | |
| Antibody 08 | | | | | | | | | | | | | | N | H | K | D | I | |

TABLE 21-continued

CDR Sequences of Antibodies 1 to 16

| | | | | | | |
|---|---|---|---|---|---|---|
| Antibody 09 | | S | P | H | | |
| Antibody 10 | | | P | H | | |
| Antibody 11 | | S | P | H | | |
| Antibody 12 | T | | P | Y | | |
| Antibody 13 | | | P | R | V | |
| Antibody 14 | | | P | T | N | Q |
| Antibody 15 | | S | P | T | | |
| Antibody 16 | T | | P | Y | | |

Assay Materials and Methods

HEK EBNA Cells

HEK EBNA cells (ATCC cat no. CRL-10852) were obtained from Invitrogen.

IL-17 Concentrations

In all the assays described below and elsewhere herein, concentrations of IL-17A or IL-17 homologues refer to the concentration of the disulphide-linked IL-17 homodimer.

Receptor-ligand Binding HTRF® Assay

Selection outputs were screened in receptor-ligand binding HTRF® (Homogeneous Time-Resolved Fluorescence) assay format for inhibition of either, biotinylated human IL-17A (Peprotech 200-17), or HIS FLAG tagged human IL-17A (in house HEK EBNA derived) binding IL-17RA Fc fusion protein (R&D Systems 177-IR).

An HTRF® (Homogeneous Time-Resolved Fluorescence) assay, is a homogeneous assay technology that utilises fluorescence resonance energy transfer between a donor and acceptor fluorophore that are in close proximity. Such assays can be used to measure macromolecular interactions by directly or indirectly coupling one of the molecules of interest to a donor fluorophore, europium (Eu3+) cryptate, and coupling the other molecule of interest to an acceptor fluorophore XL665, (a stable cross linked allophycocyanin). Excitation of the cryptate molecule (at 337 nm) results in fluorescence emission at 620 nm. The energy from this emission can be transferred to XL665 in close proximity to the cryptate, resulting in the emission of a specific long-lived fluorescence (at 665 nm) from the XL665. The specific signals of both the donor (at 620 nm) and the acceptor (at 665 nm) are measured, allowing the calculation of a 665/620 nm ratio that compensates for the presence of coloured compounds in the assay. Outputs were screened as undiluted (lead isolation) or diluted (lead optimisation), crude scFv containing periplasmic extracts prepared in; 50 mM MOPS buffer pH7.4, 0.5 mM EDTA and 0.5 M Sorbitol. 3 nM biotinylated human IL-17A (6 nM monomeric) or 3 nM HIS FLAG tagged human IL-17A (6 nM monomeric) was pre-incubated for 1 h at room temperature in the dark, with 3.2 nM streptavidin cryptate (CIS Bio International 610SAKLB), or 1.6 nM anti-flag IgG labelled with cryptate (CIS Bio International 61GF2KL) respectively. All dilutions were done in 50 mM HEPES buffer containing 0.4 M potassium fluoride and 0.1° BSA (assay buffer). In parallel, 12 nM of IL-17RA Fc fusion protein was pre-incubated for 1 h at room temperature in the dark, with 40 nM anti-human Fc antibody labelled with XL665 (CIS Bio International 61HFCXLA) in assay buffer.

After pre-incubation of the reagents, 10 µl of crude scFv sample was added to a 384 well low volume assay plate (Costar 3676). This was followed by the addition of 5 µl of the pre-incubated receptor and anti-Fc XL665 mix, and then 5 µl of the human IL-17A and cryptate detection mix.

The final concentration of IL-17A used in the assays was 0.75 nM.

Assay plates were then centrifuged at 1000 rpm at room temperature for 1 min, and incubated for 5 h at room temperature, prior to reading time resolved fluorescence at 620 nm and 665 nm emission wavelengths using an EnVision plate reader (Perkin Elmer).

Data was analysed by calculating % Delta F values for each sample. Delta F was determined according to equation 1.

$$\% \text{ Delta } F = \frac{(\text{sample } 665 \text{ nM}/620 \text{ nM ratio value}) - (\text{non-specific control } 665 \text{ nM}/620 \text{ nM ratio value})}{(\text{non-specific control } 665 \text{ nM}/620 \text{ nM ratio value})} \times 100 \quad \text{Equation 1}$$

% Delta F values were subsequently used to calculate % specific binding as described in equation 2.

$$\% \text{ specific binding} = \frac{\% \text{ Delta } F \text{ of sample}}{\% \text{ Delta } F \text{ of total binding control}} \times 100 \quad \text{Equation 2}$$

Purified scFv from positive clones identified from screening were tested in both HTRF® assays for inhibition of binding of IL-17A to IL-17 receptor. A titration of scFv concentrations was used in order to establish the clone potency as measured by $IC_{50}$ values in the assay. $IC_{50}$ values were determined using GraphPad Prism software by curve fitting using a four-parameter logistic equation (Equation 3).

$$Y = \text{Bottom} + (\text{Top} - \text{Bottom})/(1 + 10^{\wedge}((\log EC50 - X) * \text{HillSlope})) \quad \text{Equation 3:}$$

X is the logarithm of concentration. Y is specific binding Y starts at Bottom and goes to Top with a sigmoid shape.

A reference anti-IL-17 mAb (Biosource) was included in all assays as a positive control.

Epitope Competition HTRF® Assay for Inhibition of his Flag Human IL-17A Binding Anti-human IL-17A Antibody This epitope competition assay may be used to determine competition between binding members for binding IL-17A. This assay may also be used to determine cross reactivity of binding members for binding IL-17A from different species, e.g. human and cynomolgus IL-17A, and/or cross reactivity of binding members to other IL-17 family members, e.g. IL-17 homologues A to F. Binding members tested in this assay are normally in scFv format, although the skilled person may adapt the assay for use with IgG or other binding member formats. In general, concentrations of reagents will vary depending on the affinity of the antibody for IL-17A.

2 nM human HIS FLAG IL-17A (4 nM monomeric) was pre-incubated for 1 h at room temperature in the dark, with 1.6 nM anti-flag IgG labelled with cryptate. All dilutions were done in assay buffer. In parallel, 0.6 nM anti-IL-17 IgG1 (against which competition of a test binding member was to be tested) was pre-incubated for 1 h at room temperature in the dark, with 20 nM anti-human Fc antibody labelled with XL665 in assay buffer.

After pre-incubation of the reagents, 10 µl of sample was added to a 384 well low volume assay plate in duplicate. This was followed by the addition of 5 µl of the pre-incubated HIS FLAG human IL-17A and anti-Flag cryptate mix, and then 5 µl of the anti-human IL-17 antibody and XL665 detection mix.

Assay plates were then centrifuged at 1000 rpm at room temperature for 1 min, and incubated for 2 h at room temperature, prior to reading time resolved fluorescence at 620 nm and 665 nm emission wavelengths using an EnVision plate reader (Perkin Elmer).

Data was analysed by calculating % Delta F values for each sample, which were then used to determine % specific binding. $IC_{50}$ values were determined using GraphPad Prism software.

For discussion of HTRF assays generally, see the method for Receptor-ligand binding HTRF® Assay.

HT1080 IL-17 Induced IL-6 Release Assay

HT1080 cells (European Collection of Cell Cultures, ECACC—available under ECACC No. 85111505) were seeded in 96-well flat-bottomed tissue culture assay plates (Costar) at $5 \times 10^4$ cells/well. Cells were then cultured overnight in 200 µl assay media (Minimum Essential Media (MEM) with Earles salts and L-glutamine (Invitrogen), 10% (v/v) heat inactivated foetal bovine serum (FBS) (Invitrogen), 1 (v/v) MEM-non-essential amino acids without L-glutamine (Invitrogen)) in a humidified atmosphere at 37° C. and 5% $CO_2$.

A titration of purified scFv/IgG were prepared in phosphate buffered saline (PBS) and pre-incubated with IL-17A (1 nM final concentration) in assay media for 30-60 min at 37° C. In parallel media was aspirated from cells and 100 µl/well of assay media added. To this 100 µl/well of samples were added and incubated overnight (18 h±4 h). Supernatants were harvested and either assayed immediately or stored at −20° C.

IL-6 levels in supernatants were determined using human IL-6 Duoset ELISA kits (R & D Systems). ELISA was performed on FluoroNunc Maxisorb plates coated overnight with 2 µg/ml IL-6 capture antibody (Ab) (diluted in PBS, 100 µl/well). ELISA plates were washed three times with PBS-Tween and 300 µl of reagent diluent added (1% bovine serum albumin (BSA) in PBS). After 1 h incubation at room temperature (RT) ELISA plates were washed as described previously. During the 1 h incubation period the conditioned media was centrifuged at 1200 rpm for 5 min to remove cell debris. Following plate washing and preparation of the conditioned media IL-6 standards (concentration range 1000 pg/ml-1 pg/ml) and 170 µl conditioned media were added to ELISA plates and incubated at RT for 90 min.

Following incubation, samples were removed and the plates washed as before. IL-6 detection Ab at 200 ng/ml in reagent diluent (100 µl/well) was then added to the plates and incubated at RT for 60 min. Plates were then washed as before and 100 µl of streptavidin europium diluted 1:1000 in DELFIA® assay buffer (Perkin Elmer) and incubated at RT for 60 min. ELISA plates were then washed seven times with DELFIA® wash buffer and 100 µl of DELFIA® enhancement (Perkin Elmer) added. Fluorescence was quantified at 615 nm using Victor plate reader (Perkin Elmer) as per manufacturers instructions.

Data was analysed in Excel (Microsoft) by generating standard curves from the IL-6 standards for each plate and using this to calculate the amount of IL-6 present in each well. Inhibitor data was also normalised to percentage of maximal IL-6 release using the values from the IL-6 in the absence of inhibitor control and no IL-6 control. Further analysis was performed in Prism (GraphPad) where the data was plotted as % of the control response against log concentration of scFv/IgG. Determination of $IC_{50}$ values was calculated using Prism curve fitting software (Graphpad).

HT1080 Cell Assay Measuring Synergised IL-6 Release

This assay is a modification of the previously described HT1080 IL-17 induced IL-6 release assay, in which IL-6 is produced synergistically in response to the addition of human IL-17A, and human TNFα (R&D Systems).

Titrations of purified scFv/IgG were prepared in phosphate buffered saline (PBS) and pre-incubated with IL-17A (125 pM IL-17 final concentration) in assay media for 30-60 min at 37° C. In parallel media was aspirated from cells and 100 µl/well of assay media containing human TNFα was added (final TNFα concentration of 25 pM). To this 100 µl/well of samples were added and incubated overnight (18 h±4 h). Supernatants were harvested and either assayed for IL-6 immediately or stored at −20° C.

IL-6 levels were measured by ELISA, and data analysed as previously described for the HT1080 IL-17 induced IL-6 release assay.

Generation of Native IL-17A and Effects of Antibodies on T Cell Conditioned Media Induced IL-6 Production from HT1080 Cells 200 ml human blood was collected in blood bags with heparin from 3 donors. Blood was layered onto lymphoprep (30 ml blood onto 15 ml lymphoprep in Greiner Leucosep tubes) and centrifuged (2000 rpm, 20 min, room temperature, no brake). The plasma was removed into a fresh tube, centrifuged, and used to make 5% autologous plasma in sterile 0.9% saline. The mononuclear cell (PBMC) layer at the interface was removed into four 50 ml centrifuge tubes, and the volume in each tube doubled with media (RPMI supplemented with 10% hiFCS, glutamine (2 mM), penicillin (100 U/ml) and streptomycin (0.1 mg/ml) and 1 non-essential amino acids).

The PBMCs were centrifuged (1800 rpm, 10 min, room temperature), and the cell pellets were each resuspended in ~15 ml 5% plasma and pooled for each donor. The PBMCs were washed three times (1000 rpm, 10 min) in 5% plasma in order to reduce the platelet number, and then resuspended in 2 ml medium.

The PBMCs were added to a nylon wool column (Polysciences #425A, before use, soaked in media and warmed to 37° C.) and incubated (1 h, 37° C.). 20 ml medium was then added drop-wise to the column, and the effluent, containing purified T-cells, was collected.

T cells were stimulated at $5 \times 10^6$ cells/ml final in the presence of anti-CD3/anti-CD28 (Sigma, both 1 µg/ml final) TGFβ (R & D Systems, 5 ng/ml), IL-23 (R & D Systems, 50 ng/ml), anti-IFNγ (R & D Systems, 10 µg/ml) and goat anti-mouse IgG cross-linker (Sigma, 4 µg/ml). 15 minutes was left after addition of the anti-CD3/anti-CD28 before addition of cross-linker. T cells were stimulated for 48 h at 37° C. Cells were centrifuged (1000 rpm, 5 min) and supernatants removed.

HT1080 cells were seeded in overnight at $1.5 \times 10^4$ cells/well in a 96 well plate (Costar) in media (DMEM supplemented with 10% hiFCS, glutamine (2 mM), penicillin (100 U/ml) and streptomycin (0.1 mg/ml) and 1 non-essential amino acids) in a humidified atmosphere at 37° C. and 5% $CO_2$.

Titrations of antibody were prepared in media as above. Equal volumes of antibody solution were mixed with conditioned T cell media and incubated (37° C., 1 h). Media was removed from the cells and replaced with antibody solutions and cells were incubated overnight. Supernatants were harvested stored at −20° C. until analysis using the IL-6 ELISA as described (Cytoset, Biosource). IL-6 values were plotted using Origin v7.5 (OriginLab Corporation) to calculate $IC_{50}$ values for inhibition of IL-6 release compared to responses in the absence of antibody.

Chondrocyte IL-6/IL-8/MMP13/$PGE_2$-release Assay

Cartilage was obtained after knee joint replacement from patients with osteoarthritis under the approval of local ethics committees. Samples were digested overnight in 2 mg/ml collagenase at 37° C. After digestion, chondrocytes were expanded in culture flasks containing Dulbecco's modified Eagle's medium supplement with 10% foetal calf serum, penicillin (100 units), streptomycin (0.1 mg/ml), L-glutamine (2 mM), amphoteracin B (2.5 µg/ml) and non-essential amino acids (1×). Four separate cell lines were cultured and used at passage 1. Chondrocytes were harvested, plated out into 96 well plates at a density of $1.5 \times 10^4$ cells/well in culture media and left to adhere overnight at 37° C., 5% CO2.

Anti-IL-17A antibodies were diluted into assay medium (Dulbecco's modified Eagle's medium supplement with 2% fetal calf serum, penicillin (100 units), streptomycin (0.1 mg/ml), L-glutamine (2 mM), and non-essential amino acids (1×)) at a range of concentrations (varying from 0.08 to 400 nM). Recombinant human IL-17A (in house or Peprotech *E. coli* derived) was diluted into assay medium and tested at final concentrations of 0.2 and 2 nM. Recombinant IL-17A was added to the anti-IL-17 antibody solutions and pre-incubated for 1 h. Medium was removed from the chondrocytes and 100 µl recombinant IL-17/anti-IL-17A antibody mix was added. Culture supernatants were collected after an incubation of 24 h. Human IL-6, IL-8, MMP13 and $PGE_2$ were measured by ELISA.

ELISA for detection of human IL-6 production:

IL-6 was measured by ELISA, Cytoset (Biosource, CHC1264) following the manufacturers instructions. Briefly, ELISA plates were coated with a monoclonal IL-6 antibody (1 µg/ml) overnight at 4° C. and blocked with 1% BSA/bicarbonate buffer. Plates were washed with 0.05° Tween 20/PBS and incubated with culture supernatants from human chondrocytes and a biotin-conjugated mouse anti-huIL-6 antibody (0.4 µg/ml) for 2 h at room temperature. After washing, IL-6 was detected by using horseradish peroxidase-conjugated streptavidin (1:2500). Plates were developed using 3,3′,5,5′-tetramethylbenzidine. The reaction was stopped with 2 M $H_2SO_4$, and optical densities were determined at 450 nm using a PHERAstar plate reader.

ELISA for detection of human IL-8 production:

IL-8 was measured by ELISA, Cytoset (Biosource, CHC1304) following the manufacturers instructions. Briefly, ELISA plates were coated with a monoclonal IL-8 antibody (1 µg/ml) overnight at 4° C. and blocked with 1 BSA/bicarbonate buffer. Plates were washed with 0.05° Tween 20/PBS and incubated with culture supernatants of human chondroctyes and a biotin-conjugated mouse anti-huIL-8 antibody (0.1 µg/ml) for 2 h at room temperature. After washing, IL-8 was detected by using horseradish peroxidase-conjugated streptavidin (1:5000). Plates were developed using 3,3′,5,5′-tetramethylbenzidine. The reaction was stopped with 2 M $H_2SO_4$, and optical densities were determined at 450 nm using a PHERAstar plate reader.

ELISA for detection of human MMP13 production:

ELISA plates were coated with mouse anti-huMMP13 monoclonal antibody (R & D Systems, MAB511: 1 µg/ml) in phosphate buffer overnight at 4° C. Plates were blocked with 2-BSA/phosphate buffer followed by washing with 0.05° Tween 20/PBS and incubated with culture supernatants from human chondroctyes plus rabbit anti-huMMP13 polyclonal antibody (Abcam 9128: 1:2500 dilution) for 2 h at 37° C. After washing, MMP13 was detected using a horseradish peroxidase-conjugated anti-rabbit IgG (Amersham Biosciences NA934: 1:2500).

Plates were developed using 3,3′,5,5′-tetramethylbenzidine. The reaction was stopped with 2M $H_2SO_4$, and optical densities were determined at 450 nm using a PHERAstar plate reader.

ELISA for detection of human $PGE_2$ production:

ELISA plates were coated with mouse anti-rabbit IgG (Sigma, R2004: 10 µg/ml) overnight at 4° C. Plates were washed with 0.05° Tween 20/PBS and incubated with culture supernatants from human chondrocytes, Prostaglandin AChE Tracer (Cayman Chemicals, 414010) and $PGE_2$ anti-sera (prepared in-house, 1:50,000) overnight at room temperature. After washing, plates were developed using Ellman's reagent (Cayman chemicals, 400050) and optical densities were determined at 405 nm using a PHERAstar plate reader.

IL-17 Synergy Assay in Post Mortem Cartilage Explants

Post-mortem knee samples were obtained in Dulbecco's Modified Eagle Medium (DMEM), from Kings Mill Hospital, Nottingham with full ethics approval. Each knee was dissected using #22 scalpel in sterile conditions. Cartilage was isolated as full depth pieces where possible. Explant discs were cut using cork borers (5 mm) and plated as 1 explant per well of a 96 well plate in 220 µl media (DMEM (phenol red-free) supplemented with penicillin (100 U/ml) streptomycin (0.1 mg/ml) glutamine (2 mM), 1 non-essential amino acids and gentamycin (1 µg/ml)). Explants were rested for 3 days prior to stimulation. Each condition had 12 replicate explants.

Stimuli used were media alone, IL-17A (Peprotech) at 10 ng/ml, TNFα (Peprotech) at 1 ng/ml alone or in combination all diluted in media containing polymyxin B sulphate (2 µg/ml). Anti IL-17A neutralising antibodies and their isotype controls (mouse $IgG_1$ (R & D Systems), human $IgG_1$ CAT002 (Cambridge Antibody Technology Limited)) were diluted in media containing 2 µg/ml polymyxin B to 50 nM for initial experiments and from 0.5 to 50 nM for $IC_{50}$ experiments. Antibodies were mixed with cytokines where indicated and all solutions were incubated prior to addition to the explants (37° C., 30 min).

Media was removed from the explants and replaced with 220 µl stimulation media. Plates were incubated for 72 h (37° C., humidified atmosphere) before removing the supernatants for storage at −20° C. IL-6 content was analysed by ELISA (Cytoset, Biosource) according to the manufacturers instructions and as described in example 3 (Affinity of antibodies for human IL-17A). Values were calculated using Origin v7.5 (OriginLab Corporation).

IL-17A Synergy Assay in OA Synovial Fibroblasts

Samples of osteoarthritis knees from total joint replacements were obtained in DMEM from Kings Mill Hospital, Nottingham with full ethics approval. Each knee was dissected using #22 scalpel in sterile conditions. Inflamed synovium was dissected from the joint and placed in sterile T75 cm2 flask. Pieces of synovium were incubated for 24 h in collagenase solution (2 mg/ml) in DMEM, supplemented with penicillin (100 U/ml) streptomycin (0.1 mg/ml) glutamine (2 mM), 1 non-essential amino acids and amphoteracin B (2.5 µg/ml) in a humidified incubator maintained at 37° C.

The digested synovium cell suspension was cell strained, washed and cells cultured in DMEM, supplemented with penicillin (100 U/ml) streptomycin (0.1 mg/ml) glutamine (2 mM), 1 non-essential amino acids and amphoteracin B (2.5 µg/ml) in a humidified incubator maintained at 37° C. Cells were passaged every 1-2 weeks and used at passage 2. Cells were detached from the flask using trypsin-EDTA and plated in a 96 well plate at $1.5 \times 10^4$ cells per well and used 1 day after plating.

Stimuli used were media alone, IL-17A (Peprotech), TNFα (Peprotech) either alone or in combination. Anti-IL-17A neutralising antibodies and their isotype control (mouse $IgG_1$ (R & D Systems), human $IgG_1$ CAT002 (Cambridge Antibody Technology Limited)) were diluted in media containing 1 µg/ml polymyxin B to 50 nM. Antibodies were mixed with cytokines where indicated and all solutions were incubated prior to addition to the explants (37° C., 30 min).

Media was removed from the cells and replaced with 100 µl stimulation media. The plates were the incubated for 24 h (37° C., humidified atmosphere) before removing the supernatants for storage at −20° C. IL-8 content was analysed by ELISA (Cytoset, Biosource) according to the manufacturers instructions and as described in example 3 (Affinity of antibodies for human IL-17A). Values were calculated using Origin v7.5 (OriginLab Corporation).

Inhibition of IL-17A and IL-17A/TNFα Induced IL-8 in RA Synovial Fibroblasts

Samples of rheumatoid arthritis knees from total joint replacements were obtained at AstraZeneca R&D Charnwood, with full ethics approval. RA synovial fibroblasts were given to AstraZeneca R&D Alderley Park at passage 2. Cells were cultured in T225 cm² flasks in DMEM, supplemented with 10% FCS (Hyclone), penicillin (100 U/ml) streptomycin (0.1 mg/ml) glutamine (2 mM), 1 non-essential amino acids and gentamycin (1 µg/ml) in a humidified incubator maintained at 37° C.

Cells were passaged every 1-2 weeks and used at passage 5. Cells were detached from the flask using trypsin-EDTA and plated in a 96 well plate at $5 \times 10^3$ cells per well and used 3 days after plating. Stimuli used were media alone, IL-17A (Peprotech), either alone or in combination with TNFα (R&D Systems). Anti-IL-17A neutralising antibodies and their isotype control (mouse IgG1 (R & D Systems), human IgG1 CAT002 (Cambridge Antibody Technology Limited)) were diluted in media containing 1 µg/ml polymyxin B to 50 nM. Antibodies were mixed with cytokines where indicated and all solutions were incubated prior to addition to the fibroblasts (37° C., 30 min).

Media was removed from the cells and replaced with 100 µl stimulation media. The plates were the incubated for 24 h (37° C., humidified atmosphere) before removing the supernatants for storage at −20° C. IL-8 content was analysed by ELISA (Cytoset, Biosource) according to the manufacturers instructions and as described in example 3 (Affinity of antibodies for human IL-17A). IL-8 values were plotted to generate $IC_{50}$ values were calculated using Origin v7.5 (OriginLab Corporation).

pA$_2$ Analysis

The main pharmacological tool to quantify the affinity of a competitive antagonist is Schild analysis. Using this approach a system-independent means of estimating the antagonist affinity in a functional assay maybe determined. The method is based on the concept that the antagonist concentration and its affinity determines the antagonism of the agonist response. Because the antagonism can be quantified and the concentration of the antagonist is known, the affinity of the antagonist can be determined. This antagonism is quantified by measuring the ratio of equiactive concentrations of agonists, measured in the presence and absence of the antagonist, referred to as dose ratios (DR).

Dose ratios may be calculated by taking the ratio of the $EC_{50}$ of agonist (typically IL-17A) in the absence of the binding member to the $EC_{50}$ of the agonist in the presence of a single concentration of binding member. The dose ratios, expressed as log(DR-1) may then be used in a linear regression on log [binding member] to produce a Schild regression. Thus, for every concentration of binding member there will be a corresponding DR value; these are plotted as the regression of log(DR-1) upon log [binding member]. If the antagonism is competitive, there will be a linear relationship between log(DR-1) and log [binding member] according to the Schild equation wherein the equation is as follows $$\mathrm{Log}(DR\text{-}1) = \log [B] - \log K_B$$

[B] is the molar concentration of the binding member.

Under these circumstances, a value of zero for the ordinate will give an intercept of the x-axis where $\log [B] = \log K_B$. Therefore the concentration of binding member that produces a log (DR−1)=0 will be equal to the log $K_B$, the equilibrium dissociation constant of the binding member—receptor complex. This is a system independent quantification for estimation of the binding member affinity. Traditionally, this approach is used for determining the affinity of receptor antagonists, however based on similar assumptions for ligand neutralisation, a calculation of the dose ratio should enable estimation of the binding member affinity to neutralise IL-17 activity on cells also. Because the $K_B$ values are obtained from a logarithmic plot, they are log normally distributed. The negative logarithm of this particular concentration is referred to empirically as $pA_2$, the concentration of antagonist that produces a two fold shift of the agonist dose response curve. The antagonist potency can be quantified by calculating $pA_2$ from a single concentration of antagonist producing a single value for the dose ratio from the equation, wherein $$pA_2 = \log(DR\text{-}1) - \log [B]$$

[B]=molar concentration of antagonist that makes it necessary to double the agonist concentration to elicit the original submaximal response.

DR=the dose ratio is quantified by measuring the ratio of equiactive concentrations of agonist measured in the presence and absence of the antagonist.

$pA_2$ may be calculated from dose-response assay data.

Assay Method Used for $pA_2$ Analysis to Calculate Affinity of Antibodies for Human IL-17A HT1080 cells (European Collection of Cell Cultures, ECACC) were seeded in 96-well flat-bottomed tissue culture assay plates (Costar) at $5 \times 10^4$ cells/well. Cells were then cultured overnight in 200 µl assay media (MEM with Earles salts and L-glutamine, 10% (v/v) heat inactivated Australian FBS, 1 (v/v) MEM-non-essential amino acids (without L-glutamine), Invitrogen))/well in a humidified atmosphere at 37° C. and 5% $CO_2$.

A titration of IL-17A (final concentration range 1 µM to 7 pM) was then prepared in phosphate buffered saline (PBS) and pre-incubated with purified IgG (Ab final concentration range used 270 nM to 270 pM) in assay media for 30-60 min at 37° C. In parallel media was aspirated from cells and 100 µl/well of assay media added. To this 100 µl/well of samples were added and incubated overnight (18 hr±4 h). Supernatants were harvested and either assayed immediately or stored at −20° C.

IL-6 levels in supernatants were determined using Hu IL-6 Duoset ELISA kits (R & D Systems). ELISA was performed on FluoroNunc Maxisorb plates coated overnight with 2 μg/ml IL-6 capture antibody (Ab) (diluted in PBS, 100 μl/well). ELISA plates were washed three times with PBS-Tween and 300 μl of reagent diluent added (1% bovine serum albumin (BSA) in PBS). After 1 h incubation at room temperature (RT) ELISA plates were washed as before. During the 1 h incubation period the conditioned media was centrifuged at 1200 rpm for 5 min to remove cell debris. Following plate washing and preparation of the conditioned media IL-6 standards (concentration range 1000 pg/ml-1 pg/ml) and 170 μl conditioned media were added to ELISA plates and incubated at RT for 90 min. Following incubation, samples were removed and the plates washed as before. IL-6 detection Ab at 200 ng/ml in reagent diluent (100 ml/well) was then added to the plates and incubated at RT for 60 min. Plates were then washed as before and 100 μl of streptavidin europium diluted 1:1000 in DELIA® assay buffer (Perkin Elmer) and incubated at RT for 60 min. ELISA plates were then washed seven times with DELFIA wash buffer and 100 μl of DELFIA enhancement (Perkin Elmer) added. Fluorescence was quantified at 615 nm using Victor plate reader (Perkin Elmer) as per manufacturers instructions.

Data was analysed in Excel (Microsoft) by generating standard curves for the IL-6 standards added for each plate and using this to calculate the amount of IL-6 present in each well. Concentration dependent curves were normalised to percentage of maximal IL-6 release using the values from the IL-6 in the absence of inhibitor control. Further analysis was performed in Prism (GraphPad Software) where the data was plotted as % of the control response against log concentration of IgG and $IC_{50}$ values were generated using Prism curve fitting software (Graphpad). The Hillslopes of the concentration dependant curve were averaged and fixed to calculate dose ratios. These were used to generate Schild plots (also in Prism) and estimate Kd values from $pA_2$ values.

Perturbation of H/D Exchange Rate of IL-17A by Binding Member

Tagged IL-17A was used at 0.5 mg/ml in 50 mM Tris.HCl pH 7.4, 150 mM NaCl. Antibody was used at 10.6 mg/ml in PBS (1.54 mM KH2PO4, 2.71 mM Na2HPO4, 155 mM NaCl pH7.2). Antibody was coupled to POROS AL resin (Applied Biosystems) according to the manufacturer's instructions to prepare a 100 μl column which was kept at 1° C.

The column was washed in 50 mM Tris.HCl pH 7.5, 150 mM NaCl prepared in 75% D2O. IL-17A was diluted in buffer prepared with 75%. D2O to 0.125 mg/ml and incubated for 150, 500, 1500 and 5000 s before injection onto the antibody column. The column was quickly washed with 0.2 ml buffer in H2O and then incubated for the same period of time i.e. the sample that was exchanged into D2O for 150 s was exchanged back to H2O for 150 s and similarly for the samples at 500, 1500 and 5000 s. The different time points were eluted by injecting first 80 μl and then 40 μl 0.8% formic acid. The latter 40 μl was collected and 20 μl of 2 M urea, 1 M TCEP pH3 at 1° C. added. The whole mixture was injected onto a 100 μl column containing pepsin to digest the protein into peptides that were separated by rpHPLC using a gradient of acetonitrile from 12-28.5% and the masses determined on both a Thermo Finnigan LCQ electrospray mass spectrometer and a Micromass Q-TOF mass spectrometer. The SEQUEST software program (Thermo Finnigan San Jose, Calif.) was used to identify sequences of the parent peptide ions.

The effect of the antibody on the rate of exchange of different parts of IL-17 was determined essentially as described above, with the following exceptions: the IL-17 was first diluted to 0.125 mg/ml in $H_2O$ containing buffer, then injected onto the column which had been pre-washed with 50 mM Tris.HCl pH7.5, 150 mM NaCl prepared in $H_2O$. After binding, the column was washed with 50 mM Tris.HCl pH7.5, 150 mM NaCl prepared in $H_2O$ and then incubated with 50 mM Tris.HCl pH7.5, 150 mM NaCl prepared in 75% $D_2O$ for 150, 500, 1500 and 5000 s before being exchanged back into $H_2O$ and treated as above.

Cloning, Expression and Purification of Mutant IL-17A Construct

Mutant IL-17A was cloned with a C-terminal Histidine tag using Gateway® technology (Invitrogen) and conventional mutagenesis methods (using Stratagene multisite mutagenesis kit) or polymerase chain reaction. The cloned gene was inserted into the expression vector pCEP4 using the LR Clonase reaction.

Wild type and mutant IL-17A with C-terminal His tags were expressed in HEK293/EBNA cells. The cells were transfected with 30 μg of DNA per T162 flasks when the cells were 60-70% confluent. PEI transfection reagent (from Sigma) was used and the cells were incubated overnight before the media was removed and replaced with fresh media without serum and incubated for a further 72 hours. The supernatants from these cells were collected and used for purification of each recombinant protein.

Supernatant from the transfected HEK293/EBNA cells were collected and the pH adjusted to 7.4 prior to purification by affinity chromatography on Ni-Sepharose Fast Flow (GE HealthCare). The purified protein was dialysed into PBS buffer and analysed by SDS-PAGE, Edman N-terminal sequencing and Western blotting using anti-histidine antibodies as detection tools. The identity of the proteins was confirmed prior to commencing the binding and functional studies. The concentration was determined by a combination of the absorbance at 280 nm and the intensity of staining by Coomassie blue on SDS-PAGE.

BIAcore Binding Experiments of Wild Type and Mutant IL-17a

Antibodies at 100 μg/ml were immobilised to the surface of a CM5 Sensor Chip (BIAcore Cat #BR-1033-99) using BIAcore 3000 and amine-coupling kit (BIAcore Cat# BR-1000-50) according to the manufacturers instructions. The baseline was regenerated by acid regeneration using 10 mM Glycine pH1.5. Prior to each experiment the baseline was established and the ligands (at 25 nM) were injected over the surface of the chip for 7 minutes at the rate of 10 μl/min. The amount of bound IL-17A was determined by measuring the signal (RU) 30 s before and 60 s after the injection and subtracting the former from the latter.

HT1080 IL-17 Induced IL-6 Release Assay (Epitope Mapping Studies)

HT1080 cells (European Collection of Cell Cultures, ECACC—ECACC No. 85111505) were seeded in 96-well flat-bottomed tissue culture assay plates (Costar) at $5 \times 10^4$ cells/well. Cells were then cultured overnight in 200 μl assay media (Dulbecco's Modified Eagle's Media (DMEM) with L-glutamine (Invitrogen), 1 penicillin and streptomycin, 10% (v/v) heat inactivated foetal bovine serum (FBS) (Hyclone), 1% (v/v) MEM-non-essential amino acids without L-glutamine (Invitrogen)) in a humidified atmosphere at 37° C. and 5% $CO_2$.

Titrations of antibody of interest or control IgG were prepared in assay media (final concentration range 50-0.03 nM) and pre-incubated with IL-17A or mutant forms of IL-17A (final concentrations as outlined in Table 20b, range 1-2 nM) for 30-60 min at 37° C. Additionally titration curves of IL-17A or mutant IL-17A alone were prepared to assess the responsiveness of the cells to the ligands. Media was aspirated from cells and 100 µl/well of incubated antibody and IL-17A (or mutant IL-17A), or IL-17A alone added and incubated overnight (18 h±4 h). Supernatants were harvested and either assayed immediately or stored at −20° C. Data points were in triplicate within the experiment.

IL-6 levels in supernatants were determined as outlined in 'Chondrocyte IL-6/IL-8/MMP13/PGE$_2$-release assay' materials and methods.

Unknown values were extrapolated from a standard curve using 'Standard Calibration and calculations of unknowns' and IC$_{50}$s were calculated using 'Dose Response-1-15 sets' within Origin v7.5 (OriginLab Corporation).

Production and Analysis of Antibody 7 Fab for X-ray Crystallography

Purified Antibody 7 was digested to generate Fab fragments as follows:

A digest buffer of 30 mM DL-cysteine hydrochloride dissolved in GIBCO PBS (Invitrogen) was prepared.

Papain from papaya latex (Sigma) was reconstituted in digest buffer to give a 10 mg/mL solution and kept at room temperature for a minimum of 30 minutes before use.

Cysteine was added to IgG to give a 30 mM solution.

Papain was added to the IgG at a ratio of 1 mg papain to 100 mg IgG

The digest was terminated after 4 hours by the addition of 0.5M iodoacetamide (Sigma) to give 50 mM iodoacetamide in the final digest mixture.

The Fab was then purified, buffer exchanged into PBS pH 7.2 and concentrated to approximately 10 mg/ml for use in x-ray crystallography, which is described below.

X-ray Crystal Structure Determination: Protein Preparation, Crystallisation and Crystallography Recombinant human IL-17A was expressed in *E. coli* and inclusion bodies isolated using well-described methods (Rudolph et al 1996). Inclusion body protein was solubilised by homogenisation into solubilisation buffer (50 mM Tris pH 8.5, 6 M Guanidine HCl, 10 mM DTT) at room temperature for 1 hr. Solubilised protein was refolded at 0.5 mg/ml final concentration by rapid dilution by dropwise addition to refold buffer with vigorous stirring (0.1 M CAPSO pH 9.5, 0.9 M Arginine and 0.3:0.03 mM reduced:oxidised glutathione) at room temperature and left to stand overnight. Refolded protein was concentrated 5 fold using a 10 KDa MWCO spiral cartridge (Amicon Proflux™ M12 Tangential flow system) Concentrated protein was purified on S75 (GE Healthcare Biosciences) size exclusion columns equilibrated with size exclusion buffer (50 mM Tris pH 7.4, 0.15 M NaCl).

Analytical gel filtration was performed using an Ettan LC (GE Healthcare) fitted with a Superdex 200 PC 3.2/30 column (GE Healthcare) in order to identify the mixing ratio that would result in the maximum yield of the IL-17A/Fab complex. The column was equilibrated with gel filtration buffer (BTP 25 mM, pH 7.0, NaCl 100 mM) before loading 35 µl samples at 50 µlmin-1. A ratio of 3.6:1 IL-17A:Fab produced the maximum yield of complex using the materials described. IL-17A and Fab were then mixed together in this ratio and concentrated using a 500 µl 30 kDa molecular weight cut-off centrifugal concentrator (Viva Spin) previously washed with 1 ml of gel filtration buffer. The protein was concentrated to OD280=7.6 whereupon a 50 µl aliquot was removed. The remainder was further concentrated until the OD280=16.6. Hanging drop vapour diffusion crystallisation was carried out at 20° C. using Nextal trays and 2 µl+2 µl drops at the two concentrations of protein.

Diffraction quality crystals grew after two to three weeks from the high-concentration hanging drops containing 90.9 mM PCTP buffer pH 4.0, 9.1 mM PCTP Buffer pH 9.5 (1), 100 mM ammonium sulphate, 14% w/v PEG3350. Crystals were harvested, cryo-protected using (−)(−) butane2,3diol (20% v/v in the corresponding well solution) and snap frozen on an Oxford Cryostream at 100K. The crystals were screened for diffraction quality using a Rigaku FRe rotation anode generator equipped with a Saturn 944 CCD detector and Xstream cryo head. Those crystals that showed ordered diffraction were stored in readiness for data collection on ID-29 at the ESRF.

Diffraction data were collected from single crystals cooled at 100K at the European Synchrotron Radiation Facility (ESRF), beamline ID29, employing a ADSC Quantum Q315r detector. Two data sets were recorded at wavelength of 0.9787 Å over an angular range of 225° and 155° in rotation frames of 0.75° and 0.2°, respectively. Image data from each dataset were integrated with MOSFLM (Leslie, 1991) and merged and scaled individually with programs from the CCP4 suite (CCP4, 1994). Images with an internal Rmerge >20% per batch were excluded from the final scaling. Data collection statistics are shown in Table 23.

All crystals belong to the monoclinic space group P2$_1$ with typical cell dimensions of a=98.5 Å, b=66.7 Å, and c=203.8 Å with β=91.7°. The crystallographic asymmetric unit contains four molecules of Fab and two molecules of IL-17A resulting in a Matthews coefficient of 2.68 Å3/Da (Matthews, 1968) corresponding to a solvent content of 54%. The complex structure of IL-17A/Fab was determined by the method of molecular replacement using the CCP4 program MOLREP (CCP4, 1994). In a first trial, 3 molecules of the variable domain (residues 2 to 110 of the light chain and residues 2 to 124 of the heavy chain) of Fab (generated from PDB entry 1AQK, Faber et al., 1998) could be positioned and oriented. Subsequently, the positions of these Fab variable domains were fixed and 3 molecules of the constant domain of Fab (residues 111 to 216 of the light chain and residues 125 to 226 of the heavy chain) were positioned and oriented. The correctly generated Fab molecules indicated a correct Molecular Replacement solution and allowed placement the fourth and last Fab molecule in the asymmetric unit of the crystal lattice. Restrained maximum-likelihood refinement using isotropic B factors using REFMAC (Murshudov et al., 1997) resulted in an initial R$_{work}$/R$_{free}$ of 33.6%/41.5%. Manual rebuilding to the Fab model and replacement of the correct amino acid sequence were performed using the molecular graphics program COOT (Emsley & Cowtan, 2004). The IL-17A molecules were identified by visual inspection of the residual FoFc electron density map. By manually placing strands of various lengths into unoccupied 2FoFc electron density, the conserved amino acid motif of IL-17A [50-RSTSPW-57] was recognised and could be modelled unambiguously. This allowed superposition of the model of IL-17F (PDB entry 1JPY, Hymowitz et al., 2001) which allowed rapid interpretation of the dimer molecule. The superposition also made clear that the part of the molecule that interacted with Fab and was well ordered, while the opposite end of the elongated dimer molecule was not visible in the electron density, i.e., it was disordered. The IL-17A model was built as much as electron density allowed. After a round of restrained maximum-likelihood refinement using REFMAC with R$_{work}$/R$_{free}$ of 27.2%/33.4% manual rebuilding and placement of the correct amino acid sequence was applied to the IL-17A homodimer. In a last MR round using MOLREP, the rebuilt IL-17A homodimer (residues visible in the electron density are 39 to 129 of chain A and 44 to 132 of chain B) has been used to orientate and locate the second IL-17A homodimer. The IL-17A Fab complex structure—containing 4 Fab molecules and 2 IL-17A molecules—has been refined to convergence using REFMAC before water molecules and sulphate ions have been manually added using COOT. The final R-factors, $R_{work}$ and $R_{free}$ are 22.7% and 28.4%, respectively.

TABLE 23

Crystal Parameters and X-ray Data-Processing and Refinement Statistics

| | |
|---|---|
| Space group | P2$_1$ |
| Wavelength (Å) | 0.9787 |
| Cell constants a (Å) | 98.5 |
| b (Å) | 66.7 |
| c (Å) | 203.8 |
| β (°) | 91.7 |
| Resolution range (Å) | 102.1-2.63 |
| Resolution highest shell (Å) | 2.77-2.63 |
| Completeness overall (%) | 100.0 |
| Completeness highest shell (%) | 100.0 |
| Reflections, unique | 79235 |
| Multiplicity | 7.0 |
| Multiplicity highest shell | 6.9 |
| Rmerge$_{overall}$ (%)$^1$ | 12.8 |
| Rmerge highest shell (%) | 46.0 |
| Rvalue$_{overall}$ (%)$^2$ | 22.7 |
| Rvalue$_{free}$ (%) | 28.4 |

$^1$R$_{merge}$ = Σ$_{hkl}$ [(Σ$_i$ |I$_i$ − <I>|)/Σ$_i$ I$_i$]
$^2$R$_{value}$ = Σ$_{hkl}$ ||F$_{obs}$| − |F$_{calc}$||/Σ$_{hkl}$ |F$_{obs}$|
R$_{free}$ is the cross-validation R factor computed for the test set of 5% of unique reflections Sequences VH domain, VL domain and CDR sequences of binding members are shown in the appended sequence listing, in which SEQ ID NOS correspond as follows:

| | |
|---|---|
| 1 | Antibody 01 VH DNA |
| 2 | Antibody 01 VH PTN |
| 3 | Antibody 01 VH CDR1 PTN |
| 4 | Antibody 01 VH CDR2 PTN |
| 5 | Antibody 01 VH CDR3 PTN |
| 6 | Antibody 01 VL DNA |
| 7 | Antibody 01 VL PTN |
| 8 | Antibody 01 VL CDR1 PTN |
| 9 | Antibody 01 VL CDR2 PTN |
| 10 | Antibody 01 VL CDR3 PTN |
| 11 | Antibody 02 VH DNA |
| 12 | Antibody 02 VH PTN |
| 13 | Antibody 02 VH CDR1 PTN |
| 14 | Antibody 02 VH CDR2 PTN |
| 15 | Antibody 02 VH CDR3 PTN |
| 16 | Antibody 02 VL DNA |
| 17 | Antibody 02 VL PTN |
| 18 | Antibody 02 VL CDR1 PTN |
| 19 | Antibody 02 VL CDR2 PTN |
| 20 | Antibody 02 VL CDR3 PTN |
| 21 | Antibody 03 VH DNA |
| 22 | Antibody 03 VH PTN |
| 23 | Antibody 03 VH CDR1 PTN |
| 24 | Antibody 03 VH CDR2 PTN |
| 25 | Antibody 03 VH CDR3 PTN |
| 26 | Antibody 03 VL DNA |
| 27 | Antibody 03 VL PTN |
| 28 | Antibody 03 VL CDR1 PTN |
| 29 | Antibody 03 VL CDR2 PTN |
| 30 | Antibody 03 VL CDR3 PTN |
| 31 | Antibody 04 VH DNA |
| 32 | Antibody 04 VH PTN |
| 33 | Antibody 04 VH CDR1 PTN |
| 34 | Antibody 04 VH CDR2 PTN |
| 35 | Antibody 04 VH CDR3 PTN |
| 36 | Antibody 04 VL DNA |
| 37 | Antibody 04 VL PTN |
| 38 | Antibody 04 VL CDR1 PTN |
| 39 | Antibody 04 VL CDR2 PTN |
| 40 | Antibody 04 VL CDR3 PTN |
| 41 | Antibody 05 VH DNA |
| 42 | Antibody 05 VH PTN |
| 43 | Antibody 05 VH CDR1 PTN |
| 44 | Antibody 05 VH CDR2 PTN |
| 45 | Antibody 05 VH CDR3 PTN |
| 46 | Antibody 05 VL DNA |
| 47 | Antibody 05 VL PTN |
| 48 | Antibody 05 VL CDR1 PTN |
| 49 | Antibody 05 VL CDR2 PTN |
| 50 | Antibody 05 VL CDR3 PTN |
| 51 | Antibody 06 VH DNA |
| 52 | Antibody 06 VH PTN |
| 53 | Antibody 06 VH CDR1 PTN |
| 54 | Antibody 06 VH CDR2 PTN |
| 55 | Antibody 06 VH CDR3 PTN |
| 56 | Antibody 06 VL DNA |
| 57 | Antibody 06 VL PTN |
| 58 | Antibody 06 VL CDR1 PTN |
| 59 | Antibody 06 VL CDR2 PTN |
| 60 | Antibody 06 VL CDR3 PTN |
| 61 | Antibody 07 VH DNA |
| 62 | Antibody 07 VH PTN |
| 63 | Antibody 07 VH CDR1 PTN |
| 64 | Antibody 07 VH CDR2 PTN |
| 65 | Antibody 07 VH CDR3 PTN |
| 66 | Antibody 07 VL DNA |
| 67 | Antibody 07 VL PTN |
| 68 | Antibody 07 VL CDR1 PTN |
| 69 | Antibody 07 VL CDR2 PTN |
| 70 | Antibody 07 VL CDR3 PTN |
| 71 | Antibody 08 VH DNA |
| 72 | Antibody 08 VH PTN |
| 73 | Antibody 08 VH CDR1 PTN |
| 74 | Antibody 08 VH CDR2 PTN |
| 75 | Antibody 08 VH CDR3 PTN |
| 76 | Antibody 08 VL DNA |
| 77 | Antibody 08 VL PTN |
| 78 | Antibody 08 VL CDR1 PTN |
| 79 | Antibody 08 VL CDR2 PTN |
| 80 | Antibody 08 VL CDR3 PTN |
| 81 | Antibody 09 VH DNA |
| 82 | Antibody 09 VH PTN |
| 83 | Antibody 09 VH CDR1 PTN |
| 84 | Antibody 09 VH CDR2 PTN |
| 85 | Antibody 09 VH CDR3 PTN |
| 86 | Antibody 09 VL DNA |
| 87 | Antibody 09 VL PTN |
| 88 | Antibody 09 VL CDR1 PTN |
| 89 | Antibody 09 VL CDR2 PTN |
| 90 | Antibody 09 VL CDR3 PTN |
| 91 | Antibody 10 VH DNA |
| 92 | Antibody 10 VH PTN |
| 93 | Antibody 10 VH CDR1 PTN |
| 94 | Antibody 10 VH CDR2 PTN |
| 95 | Antibody 10 VH CDR3 PTN |
| 96 | Antibody 10 VL DNA |
| 97 | Antibody 10 VL PTN |
| 98 | Antibody 10 VL CDR1 PTN |
| 99 | Antibody 10 VL CDR2 PTN |
| 100 | Antibody 10 VL CDR3 PTN |
| 101 | Antibody 11 VH DNA |
| 102 | Antibody 11 VH PTN |
| 103 | Antibody 11 VH CDR1 PTN |
| 104 | Antibody 11 VH CDR2 PTN |
| 105 | Antibody 11 VH CDR3 PTN |
| 106 | Antibody 11 VL DNA |
| 107 | Antibody 11 VL PTN |
| 108 | Antibody 11 VL CDR1 PTN |
| 109 | Antibody 11 VL CDR2 PTN |
| 110 | Antibody 11 VL CDR3 PTN |
| 111 | Antibody 12 VH DNA |

| | |
|---|---|
| 112 | Antibody 12 VH PTN |
| 113 | Antibody 12 VH CDR1 PTN |
| 114 | Antibody 12 VH CDR2 PTN |
| 115 | Antibody 12 VH CDR3 PTN |
| 116 | Antibody 12 VL DNA |
| 117 | Antibody 12 VL PTN |
| 118 | Antibody 12 VL CDR1 PTN |
| 119 | Antibody 12 VL CDR2 PTN |
| 120 | Antibody 12 VL CDR3 PTN |
| 121 | Antibody 13 VH DNA |
| 122 | Antibody 13 VH PTN |
| 123 | Antibody 13 VH CDR1 PTN |
| 124 | Antibody 13 VH CDR2 PTN |
| 125 | Antibody 13 VH CDR3 PTN |
| 126 | Antibody 13 VL DNA |
| 127 | Antibody 13 VL PTN |
| 128 | Antibody 13 VL CDR1 PTN |
| 129 | Antibody 13 VL CDR2 PTN |
| 130 | Antibody 13 VL CDR3 PTN |
| 131 | Antibody 14 VH DNA |
| 132 | Antibody 14 VH PTN |
| 133 | Antibody 14 VH CDR1 PTN |
| 134 | Antibody 14 VH CDR2 PTN |
| 135 | Antibody 14 VH CDR3 PTN |
| 136 | Antibody 14 VL DNA |
| 137 | Antibody 14 VL PTN |
| 138 | Antibody 14 VL CDR1 PTN |
| 139 | Antibody 14 VL CDR2 PTN |
| 140 | Antibody 14 VL CDR3 PTN |
| 141 | Antibody 15 VH DNA |
| 142 | Antibody 15 VH PTN |
| 143 | Antibody 15 VH CDR1 PTN |
| 144 | Antibody 15 VH CDR2 PTN |
| 145 | Antibody 15 VH CDR3 PTN |
| 146 | Antibody 15 VL DNA |
| 147 | Antibody 15 VL PTN |
| 148 | Antibody 15 VL CDR1 PTN |
| 149 | Antibody 15 VL CDR2 PTN |
| 150 | Antibody 15 VL CDR3 PTN |
| 151 | Antibody 16 VH DNA |
| 152 | Antibody 16 VH PTN |
| 153 | Antibody 16 VH CDR1 PTN |
| 154 | Antibody 16 VH CDR2 PTN |
| 155 | Antibody 16 VH CDR3 PTN |
| 156 | Antibody 16 VL DNA |
| 157 | Antibody 16 VL PTN |
| 158 | Antibody 16 VL CDR1 PTN |
| 159 | Antibody 16 VL CDR2 PTN |
| 160 | Antibody 16 VL CDR3 PTN |
| 161 | Cynomolgus IL-17 DNA |
| 162 | Cynomolgus IL-17 PTN |
| 163 | Antibody 1 VL DNA |
| 164 | Antibody 1 VL PTN |
| 165 | Antibody 2 VL DNA |
| 166 | Antibody 2 VL PTN |
| 167 | Antibody 3 and 9 VL DNA |
| 168 | Antibody 3 and 9 VL PTN |
| 169 | Antibody 4 VL DNA |
| 170 | Antibody 4 VL PTN |
| 171 | Antibody 5 and 8 VL DNA |
| 172 | Antibody 5 and 8 VL PTN |
| 173 | Antibody 6 VL DNA |
| 174 | Antibody 6 VL PTN |
| 175 | Antibody 7 VL DNA |
| 176 | Antibody 7 VL PTN |
| 177 | Antibody 10 VL DNA |
| 178 | Antibody 10 VL PTN |
| 179 | Antibody 11 VL DNA |
| 180 | Antibody 11 VL PTN |
| 181 | Antibody 12 and 16 VL DNA |
| 182 | Antibody 12 and 16 VL PTN |
| 183 | Antibody 13 VL DNA |
| 184 | Antibody 13 VL PTN |
| 185 | Antibody 14 VL DNA |
| 186 | Antibody 14 VL PTN |
| 187 | Antibody 15 VL DNA |
| 188 | Antibody 15 VL PTN |
| 189 | VH FR1 PTN |
| 190 | VH FR2 PTN |
| 191 | VH FR3 PTN |
| 192 | VH FR4 PTN |
| 193 | VL FR1 PTN |
| 194 | VL FR2 PTN |
| 195 | VL FR3 PTN |
| 196 | VL FR4 PTN |
| 197 | Tagged mature hIL-17A |
| 198 | Mature human IL-17A |
| 199 | Human IL-17A peptide |
| 200 | Tagged mutant precursor hIL-17A |
| 201 | Mutant mature human IL-17A |

PTN = amino acid sequence
Antibodies 3, 4 and 5 have the same VH domain.
Antibodies 9, 10 and 12 have the same VH domain.
Antibodies 2 and 10 have the same VL CDRs. The VL domain sequence shown for Antibody 2 is germlined and the VL domain sequence shown for Antibody 10 is non-germlined.
Antibodies 3, 9 and 11 have the same VL domain.
Antibodies 4 and 15 have the same VL domain.
Antibodies 5 and 8 have the same VL domain.
Antibodies 12 and 16 have the same VL domain.

The VL domain nucleotide sequences of antibodies 1 to 16 do not include the gag codon shown at the 3' end in SEQ ID NOS: 6, 16, 26, 36, 46, 56, 66, 76, 86, 96, 106, 116, 126, 136, 146 and 156. Correspondingly, the VL domain amino acid sequences do not include the C-terminal Glu residue (residue 112) in SEQ ID NOS: 7, 17, 27, 37, 47, 57, 67, 77, 87, 97, 107, 117, 127, 137, 147 and 157, respectively. The Glu112 residue and corresponding gag codon were not expressed in Antibodies 1 to 16. A comparison of the written sequences with germline gene segments indicates that the Glu residue and corresponding gag codon do not form part of the VL domain.

The Gly residue at position 111 (Kabat residue 108) was present in the expressed scFv and IgG sequences. However, this residue is not present in human germline j segment sequences that form the framework 4 region of the VL domain. The Gly residue is not considered a part of the VL domain.

To express the light chain of the IgG, a nucleotide sequence encoding the antibody light chain was provided, comprising a first exon encoding the VL domain, a second exon encoding the CL domain, and an intron separating the first exon and the second exon. Under normal circumstances, the intron is spliced out by cellular mRNA processing machinery, joining the 3' end of the first exon to the 5' end of the second exon. Thus, when DNA having the said nucleotide sequence was expressed as RNA, the first and second exons were spliced together. Translation of the spliced RNA produces a polypeptide comprising the VL and the CL domain. After splicing, the Gly at position 111 is encoded by the last base (g) of the VL domain framework 4 sequence and the first two bases (gt) of the CL domain.

The VL domain sequences of Antibodies 1 to 16 are SEQ ID NOS: 163 to 188 as indicated above. The VL domain nucleotide sequences end with cta as the final codon, and Leu is the final amino acid residue in the corresponding VL domain amino acid sequences.

References

All references cited anywhere in this specification, including those cited anywhere above, are incorporated herein by reference in their entirety for all purposes.

Al-Lazikani et al. Journal Molecular Biology 273(4):927-948, 1997

Altschul et al. (1990) J. Mol. Biol. 215: 405-410

Amit et al., Science, 233:747-753, 1986

Andersen, D C. & Krummen, L. Current Opinion in Biotechnology 13:117, 2002

Antonysamy, M A. et al. J. Immunol. 162(1):577-84, 1999

Ausubel et al. eds., Short Protocols in Molecular Biology: A Compendium of Methods from Current Protocols in Molecular Biology, John Wiley & Sons, 4$^{th}$ edition 1999
Bagshawe, K. D. et al. Antibody, Immunoconjugates and Radiopharmaceuticals 4:915-922, 1991
Bannister, D et al Biotechnol bioeng 94(5): 931-937, 2006
Barbas et al. Proc. Natl. Acad. Sci., 91:3809-3813, 1994
Betteli, E. et al. Nature 441 (7090), 166-168, (2006)
Bird et al. Science, 242, 423-426, 1988
Burchill, M A. et al. Infect Immun. 71(6):3437-42, 2003
Bush, K. et al. Arthritis Rheum. 46:802-805, 2002
Cai, L. et al. Cytokine 16(1) 10-21, 2001
Caton et al. J. Immunol., 144:1965-1968, 1990
CCP4 (Collaborative Computational Project, Number 4) (1994) The CCP4 suite: programs for protein crystallography. Acta Crystallogr D 50: 760-763
Chabaud, M. et al. J. Immunol. 161, 409-414, 1998
Chabaud, M. et al. Arthritis Rheum. 42, 963-970, 1999
Chabaud, M. and Miossec, P. Arthritis Rheum. 44(6) 1293-1303, 2001
Chadd, H E. and Chamow, S M. Current Opinion in Biotechnology 12:188-194, 2001
Cho, M L. et al. Arthritis Rheum. 50(3), 776-784, 2004
Chothia et al. Science, 223:755-758, 1986
Chothia et al. J. Mol. Biol., 196:901-917, 1987
Chothia et al. Nature, 342:877-883, 1989
Chothia, C. et al. Journal Molecular Biology 1992227, 799-817, 1992
Chung, D R. et al. J Exp Med. 195(11):1471-8, 2002
Clackson, T. and Lowman, H. B. Phage Display—A Practical Approach, 2004. Oxford University Press
Csiszar, A. FASEB J.; 17(9):1183-5, 2003
Csiszar, A. and Ungvari, Z. Med Hypotheses, 63(4):696-8, 2004
Denison DGT. (Editor), Holmes, C C. et al. Bayesian Methods for Nonlinear Classification and Regression (Wiley Series in Probability and Statistics). John Wiley & Sons; (July 2002), ISBN: 0471490369
Emsley, P. & Cowtan, K. (2004) Coot: model-building tools for molecular graphics Acta Crystallogr D60: 2126-2132
Englander, S. W. et al. Methods Enzymol. 232:26-42, 1994
Faber et al., Immunotechnology 3, 253-270, 1998
Faour, W H. et al. J. Biol. Chem. 278(29):26897-26907, 2003
Ferretti, S. et al. J. Immunol. 170:2106-2112, 2003
Fisman, E Z. Cardiovasc Diabetol. 12:2:11, 2003
Foote & Winter J Mol. Biol. 1992 Mar. 20; 224(2):487-99
Fort, M. et al. Immunity, 15:985-995, 2001
Fujino, S. et al. Gut 52:65-70, 2003
Ghose, A K. & Viswanadhan, V N. Combinatorial Library Design and Evaluation Principles, Software, Tools, and Applications in Drug Discovery. ISBN: 0-8247-0487-8
Glennie, M J. et al., 1987 J. Immunol. 139, 2367-2375
Gram et al., 1992, Proc. Natl. Acad. Sci., USA, 89:3576-3580
Guex, N. and Peitsch, M. C. Electrophoresis (1997) 18, 2714-2723
Haan & Maggos (2004) BioCentury, 12(5): A1-A6
Hamzaoui, K. et al. Scand J Rheumatol. 31(4):205-10, 2002
Harlow and Lane, Antibodies: A Laboratory Manual, Cold Spring Harbor Laboratory, Cold Spring Harbor N.Y., pp. 726, 1988
Haudenschild, D. et al. J Biol. Chem., 277:4309-16, 2002
Haudenschild, D. et al. Prostate, ahead of print, 2006
Haznedaroglu, S. et al. Clin Exp Rheumatol. 23(4 Suppl 38):S77-80, 2005
Hellings, P W. et al. Am J Respir Cell Mol. Biol. 28(1):42-50, 2003
Holliger, P. et al, PNAS USA 90:6444-6448, 1993a
Holliger, P. & Winter, G. 1999 Cancer and metastasis rev. 18:411-419, 1999
Holt et al. Trends in Biotechnology 21, 484-490, 2003
Honorati, M C. et al. Osteoarthritis & Cartilage 10:799-807, 2002
Hsieh, H G. et al. Transpl. Int. 14:287-298, 2001
Hu, S. et al, Cancer Res., 56, 3055-3061, 1996
Hunter W M. and Greenwood F C. Nature, 194:495, 1962
Hurst, S D. et al. J Immunol, 169:443-453, 2002
Huston. PNAS USA, 85, 5879-5883, 1988
Hutchings, C. Generation of Naïve Human Antibody Libraries, in Antibody Engineering, R. Kontermann and S. Dubel, Editors. 2001, Springer Laboratory Manuals, Berlin. p. 93
Hymowitz, S G. et al. EMBO J, 50:53321-5341, 2001
Kabat, E A. et al. Sequences of Proteins of Immunological Interest. 4$^{th}$ Edition. US Department of Health and Human Services, 1987
Kabat, E A. I. (1991a) Sequences of Proteins of Immunological Interest, 5th Edition. US Department of Health and Human Services, Public Service, NIH, Washington
Kabat et al., J. Immunol., 147:1709-1719, 1991 (b)
Kandel, Abraham & Backer, Eric. Computer-Assisted Reasoning in Cluster Analysis. Prentice Hall PTR, (May 11, 1995), ISBN: 0133418847
Karpusas et el., *Structure* 9, 321, 2001
Katz, Y. et al. Arthritis Rheum. 44(9):2176-2184, 2001
Kay, B K., Winter, J., and McCafferty, J. Phage Display of Peptides and Proteins: A Laboratory Manual, San Diego: Academic Press, 1996
Knappik et al. J. Mol. Biol. 296, 57-86, 2000
Koenders, M I. et al. Am J Pathol. 167(1):141-9, 2005 (a)
Koenders, M I. et al. Arthritis Rheum. 52(3):975-983, 2005 (b)
Kohler and Milstein, Nature, 256:495-497, 1975
Koide et al. Journal of Molecular Biology, 284:1141-1151, 1998
Kontermann, R & Dubel, S, Antibody Engineering, Springer-Verlag New York, LLC; 2001, ISBN: 3540413545.
Kotake, S. et al. J. Clin. Invest. 103:1345-1352, 1999
Kramer, G. and Marberger, M. Curr Opin Urol. January; 16(1):25-9, 2006
Krebs et al. Journal of Immunological Methods, 254:67-84, 2001
Krzanowski, W. Principles of Multivariate Analysis: A User's Perspective (Oxford Statistical Science Series, No 22 (Paper)). Oxford University Press; (December 2000), ISBN: 0198507089
Kuestner R. et al. Abstract 206, Keystone Symposia 'Cytokine, Disease and Therapeutic Intervention', 2005
Kurasawa, K. et al. Arthritis Rheum, 43(11):2455-63, 2000
Larrick, J W. and Thomas, D W. Current Opinion in Biotechnology 12:411-418, 2001
Le Grand, A. et al. Arthritis Rheum. 44(9):2078-2083, 2001
Ledermann J A. et al. Int. J. Cancer 47:659-664, 1991
Lee, J. et al. J Biol. Chem. 2769:1660-1664, 2001
Leslie A. (1991) Macromolecular data processing. In Moras, D., Podjarny, A. D. and Thierry, J. C. (eds), *Crystallographic Computing* V. Oxford University Press, Oxford, UK, pp. 27-38
Li, H. et al. Proc. Natl. Acad. Sci. USA, 97:773-778, 2000
Linden, A. Pulm Pharmacol Ther., 19(1):47-50, 2006
Lock, C. et al. Nat. Med. 8:500-508, 2002
Lubberts, E. et al. Arthritis Rheum. 43:1300-1306, 2000
Lubberts, E. et al. J. Immunol. 167(2):1004-1013, 2001
Lubberts, E. et al. J. Immunol. 170(5):2655-6, 2003
Lubberts, E. et al. Arthritis Rheum. 50(2):650-659, 2004

Mach et al Anal. Biochem. 200(1): 20-26, 1992
Maertzdorf, J. et al. J Immunol, 169(10):5897-903, 2002
Maggio, E. et al. Ann Oncol., 13 Suppl 1:52-6, 2002
Malemud, C J. et al. Biodrugs 18(1):23-35, 2004
Marks et al. Bio/Technology, 10:779-783, 1992
Matthews, *J. Mol. Biol.* 33, 491-497 (1968)
McCafferty et al. Nature, 348:552-554, 1990
Mendez, M. et al. Nature Genet, 15(2):146-156, 1997
Merchand et al. Nature Biotech., 16:677-681, 1998
Molet, S. M. et al. J. Allergy Clin. Immunol. 108:430-438, 2001
Moore, E E. et al. Neuromusc Disord., 12:141-150, 2002
Moseley, T A. et al. Cyto Growth Factor Rev., 14:155-174, 2003
Murshudov, G. N., Vagin, A. A., and Dodson, E. J. (1997) Acta Crystallogr D53: 240-255
Nakae, S. et al. J. Immunol. 171(11):6173-6177, 2003
Nielsen, O H. et al. Scand J Gastroenterol, 38(2):180-5, 2003
Norman et al. Applied Regression Analysis. Wiley-Interscience; 3$^{rd}$ edition (April 1998) ISBN: 0471170828
Numasaki, M. et al. J. Immunol., 175(9):6177-89, 2005
Nygren et al. Current Opinion in Structural Biology, 7:463-469, 1997
Oda, N. et al. Am J Respir Crit. Care Med., 171(1):12-8, 2005
Osbourn, J K. et al. Immunotechnology, 2(3):181-96, 1996
Padavattan et al., *J. Mol. Biol.* 368, 742, 2007
Pantazatos, D. et al. Proc. Natl. Acad. Sci. 101(3):751-756, 2004
Pearson and Lipman (1988) PNAS USA 85: 2444-2448
Persic, L. et al. Gene. 187(1):9-18, 1997
Plückthun, A. Bio/Technology 9:545-551, 1991
Reiter, Y. et al, Nature Biotech, 14:1239-1245, 1996
Repp, R. et al., J. Hemat. 377-382, 1995
Ridgeway, J B B. et al, Protein Eng., 9:616-621, 1996
Robinson, J R. ed., Sustained and Controlled Release Drug Delivery Systems, Marcel Dekker, Inc., New York, 1978
Ruddy, M J. et al. J. Biol. Chem. 279(4):2559-2567, 2004
Rudolf, R. et al. *FASEB J.* 10, 49-56, 1996
Sambrook and Russell, Molecular Cloning: a Laboratory Manual: 3rd edition, 2001, Cold Spring Harbor Laboratory Press
Schier et al., J. Mol. Biol. 263:551-567, 1996
Segal et al. PNAS, 71:4298-4302, 1974
Sharon et al. PNAS, 87:4814-4817, 1990 (a)
Sharon et al. J. Immunol., 144:4863-4869, 1990 (b)
Shen, F. et al. Zhonghua Jie He He Hu Xi Za Zhi, 27(10): 654-8 2004(a)
Shen, F. et al. Zhonghua Nei Ke Za Zhi, 43(12):888-90, 2004 (b)
Shi, Y. et al. J. Biol Chem, 275:19167-19176, 2000
Smith and Waterman (1981) J. Mol. Biol. 147: 195-197
Sohn, M H. et al. Scand J Rheumatol. 32(6)346-6, 2003
Staerz U. D. and Bevan M. J. PNAS 83, 1986
Stamp, L. K. et al. J. Rheumatol. 31(7):1246-1254, 2004
Starnes, T. et al. J. Immunol, 169:642-646, 2002
Stemmer, Nature, 370:389-391, 1994
Suresh M R. et al., Method Enzymol. 121:210-228, 1986
Sylvester, J. et al. Cell Signal 16(4):469-476, 2004
Takahashi, K. J Clin Periodontol. 32(4):369-74, 2005
Tang, J L. et al. Transplantation, 72(2):348-50, 2001
Teunissen, M. B. M. et al. J. Invest. Dermatol. 111:645-649, 1998
Thompson, J. et al. J Mol. Biol. 256(1):77-88, 1996
Toda, M. et al. J Allergy Clin Immunol. 111(4):875-81, 2003
Tomlinson, I., VBASE. MRC Centre of Protein Engineering, Cambridge, UK, 1997
Touil, T. et al. Drug News Perspect., 19(2):77-83, 2006
Toy, D., et al Journal of Immunology., 177(1):36-39, 2006
Vanaudenaerde, B M. et al. J Heart Lung Transplant. 22(11): 1280-3, 2003
Van Bezooijen, R L. et al. J Bone Miner Res. 14(9):1513-21, 1999
Vaughan, T J. et al. Nature Biotechnology 14(3):309-14, 1996
Vernal, R. et al. J Clin Periodontol. 32(4):383-9, 2005
Voet & Voet, Biochemistry, 2nd Edition, (Wiley) 1995
Ward, E S. et al., Nature 341:544-546, 1989
Wess, L. In: BioCentury, The Bernstein Report on BioBusiness, 12(42), A1-A7, 2004
Whitelegg, N R U. and Rees, A R. Prot. Eng., 12:815-824, 2000
Witten, Ian H. & Frank, Eibe. Data Mining: Practical Machine Learning Tools and Techniques with Java Implementations. Morgan Kaufmann; (Oct. 11, 1999), ISBN: 1558605525
Wold, et al. Multivariate data analysis in chemistry. Chemometrics—Mathematics and Statistics in Chemistry (Ed.: B. Kowalski), D. Reidel Publishing Company, Dordrecht, Holland, 1984 (ISBN 90-277-1846-6)
Wong, C K. et al. Lupus, 9(8):589-93, 2000
Wong, C K. et al. Clin Exp Immunol. 125(2):177-83, 2001
Yen, D. et al. J Clin Invest. 116(5):1310-6, 2006
Yoshida, S. et al. Am J Transplant. 6(4):724-35, 2006
Zhang, Z. et al. Inflamm Bowel Dis. 12(5):382-8, 2006

The invention claimed is:

1. An isolated antibody or antibody fragment thereof for human IL-17A, wherein the antibody or antibody fragment thereof comprises a set of CDRs comprising HCDR1, HCDR2 and HCDR3, which amino acid sequences are identical to SEQ ID NOs:63, 64 and 65, respectively; and LCDR1, LCDR2 and LCDR3, which amino acid sequences are identical to SEQ ID NOs:68, 69 and 70, respectively.

2. The antibody or antibody fragment thereof according to claim 1, wherein the antibody or antibody fragment thereof has an IC50 of not more than 1 nM as determined in an HT1080 cell assay of IL-6 release in response to 1 nM human IL-17A.

3. The antibody or antibody fragment thereof according to claim 2, wherein the antibody or antibody fragment thereof has an IC50 of not more than 0.5 nM as determined in an HT1080 cell assay of synergised release of IL-6 in response to 125 pM human IL-17A and 25 pM TNFα.

4. An isolated antibody or antibody fragment thereof for human IL-17A, comprising a VH domain with the VH domain amino acid sequence shown in SEQ ID NO: 62 and a VL domain with the VL domain amino acid sequence shown in SEQ ID NO: 176.

5. The antibody or antibody fragment thereof according to claim 4, which is an IgG1.

6. The antibody or antibody fragment thereof according to claim 4, which is an scFv.

7. A composition comprising the antibody or antibody fragment thereof of claim 4 and a pharmaceutically acceptable excipient.

8. An isolated antibody or antibody fragment thereof for human IL-17A, wherein the antibody or antibody fragment thereof comprises a set of CDRs comprising HCDR1, HCDR2, HCDR3, LCDR1, LCDR2 and LCDR3, which amino acid sequences are selected from the group consisting of:

(a) SEQ ID NO:3, SEQ ID NO:4, SEQ ID NO:5; SEQ ID NO:8, SEQ ID NO:9 and SEQ ID NO:10;

(b) SEQ IDNO:13, SEQ IDNO:14, SEQ IDNO:15; SEQ IDNO:18, SEQ IDNO:19 and SEQ ID NO:20; and (c) SEQ ID NO:23, SEQ ID NO:24, SEQ ID NO:25; SEQ ID NO:28, SEQ ID NO:29 and SEQ ID NO:30.

* * * * *